(12) United States Patent
Watterson et al.

(10) Patent No.: US 7,981,000 B2
(45) Date of Patent: *Jul. 19, 2011

(54) SYSTEMS FOR INTERACTION WITH EXERCISE DEVICE

(75) Inventors: Scott R. Watterson, Logan, UT (US);
William T. Dalebout, Logan, UT (US);
Darren C. Ashby, Richmond, UT (US)

(73) Assignee: Icon IP, Inc., Logan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/684,605

(22) Filed: Jan. 8, 2010

(65) Prior Publication Data

US 2010/0179028 A1   Jul. 15, 2010

Related U.S. Application Data

(60) Continuation of application No. 12/276,900, filed on Nov. 24, 2008, now Pat. No. 7,645,213, which is a continuation of application No. 11/429,858, filed on May 8, 2006, now Pat. No. 7,455,622, which is a division of application No. 09/641,627, filed on Aug. 18, 2000, now Pat. No. 7,166,062, which is a continuation-in-part of application No. 09/349,608, filed on Jul. 8, 1999, now Pat. No. 6,312,363, and a continuation-in-part of application No. 09/496,560, filed on Feb. 2, 2000, now Pat. No. 6,447,424.

(51) Int. Cl.
*A63B 71/00* (2006.01)
(52) U.S. Cl. ............... 482/8; 482/1; 482/9; 482/901
(58) Field of Classification Search .............. 482/1–9, 482/51, 54, 900–902; 434/247
See application file for complete search history.

(56) References Cited

U.S. PATENT DOCUMENTS

| 3,518,985 A | 7/1970 | Quinton |
| 3,602,502 A | 8/1971 | Hampl |
| 3,802,698 A | 4/1974 | Burian et al. |
| 3,845,756 A | 11/1974 | Olsson |
| 3,903,613 A | 9/1975 | Bisberg |

(Continued)

FOREIGN PATENT DOCUMENTS

CN    1162495    10/1997

(Continued)

OTHER PUBLICATIONS

Supplemental Notice of Allowability dated Jul. 29, 2010, 2 pages, U.S. Appl. No. 11/314,133.

(Continued)

*Primary Examiner* — Glenn Richman
(74) *Attorney, Agent, or Firm* — Workman Nydegger

(57) ABSTRACT

An exercise device is configured to enable a user to interact with a trainer in real-time communication. The exercise device includes an exercise mechanism having a movable element for movement in performance of exercise by a user. Communicating with the exercise mechanism is an interface adapted for gathering a first real-time signal from the user. The interface communicates with a communication system for receiving a packetized second real-time signal including a synchronized control signal from the trainer. The exercise device includes an output device configured to reproduce the second real-time signal. The control signals carried by the second signal are used to control the operating parameters of the exercise mechanism in real-time.

8 Claims, 20 Drawing Sheets

U.S. PATENT DOCUMENTS

| | | |
|---|---|---|
| 4,020,795 A | 5/1977 | Marks |
| 4,112,928 A | 9/1978 | Putsch |
| 4,151,988 A | 5/1979 | Nabinger |
| 4,220,996 A | 9/1980 | Searcy |
| 4,278,095 A | 7/1981 | Lapeyre |
| 4,358,105 A | 11/1982 | Sweeney |
| 4,408,613 A | 10/1983 | Relyea |
| 4,504,055 A | 3/1985 | Wells |
| 4,542,897 A | 9/1985 | Meldon et al. |
| 4,544,152 A | 10/1985 | Taitel |
| 4,549,044 A | 10/1985 | Durham |
| 4,556,216 A | 12/1985 | Pitkanen |
| 4,571,682 A | 2/1986 | Silverman et al. |
| 4,642,769 A | 2/1987 | Petrofsky |
| 4,659,074 A | 4/1987 | Taitel et al. |
| 4,687,195 A | 8/1987 | Potts |
| 4,702,475 A | 10/1987 | Elstein et al. |
| 4,708,337 A | 11/1987 | Shyu |
| 4,708,837 A | 11/1987 | Baxter et al. |
| 4,709,917 A | 12/1987 | Yang |
| 4,757,495 A | 7/1988 | Decker et al. |
| 4,763,284 A | 8/1988 | Carlin |
| 4,765,613 A | 8/1988 | Voris |
| 4,786,049 A | 11/1988 | Lautenschlager |
| 4,818,234 A | 4/1989 | Redington et al. |
| 4,828,257 A | 5/1989 | Dyer et al. |
| 4,837,157 A | 6/1989 | Turnell et al. |
| 4,842,266 A | 6/1989 | Sweeney, Sr. et al. |
| 4,842,274 A | 6/1989 | Oosthuizen et al. |
| 4,848,737 A | 7/1989 | Ehrenfield |
| 4,860,763 A | 8/1989 | Schminke |
| 4,866,704 A | 9/1989 | Bergman |
| 4,889,108 A | 12/1989 | Bond et al. |
| 4,919,418 A | 4/1990 | Miller |
| 4,925,183 A | 5/1990 | Kim |
| 4,925,189 A | 5/1990 | Braeunig |
| 4,927,136 A | 5/1990 | Leask |
| 4,934,694 A | 6/1990 | McIntosh |
| 4,938,474 A | 7/1990 | Sweeney et al. |
| 4,949,993 A | 8/1990 | Stark et al. |
| 4,959,713 A | 9/1990 | Morotomi et al. |
| 4,998,725 A | 3/1991 | Watterson et al. |
| 5,020,795 A | 6/1991 | Airy et al. |
| 5,054,774 A | 10/1991 | Belsito |
| 5,062,632 A | 11/1991 | Dalebout et al. |
| 5,067,710 A | 11/1991 | Watterson et al. |
| 5,078,152 A | 1/1992 | Bond et al. |
| 5,086,385 A | 2/1992 | Launey et al. |
| 5,089,960 A | 2/1992 | Sweeney, Jr. |
| 5,104,120 A | 4/1992 | Watterson et al. |
| 5,113,427 A | 5/1992 | Ryoichi et al. |
| 5,137,501 A | 8/1992 | Mertesdorf |
| 5,145,475 A | 9/1992 | Cares |
| 5,149,084 A | 9/1992 | Dalebout et al. |
| 5,180,347 A | 1/1993 | Chen |
| 5,195,935 A | 3/1993 | Fencel |
| 5,201,772 A | 4/1993 | Maxwell |
| 5,213,555 A | 5/1993 | Hood et al. |
| 5,230,673 A | 7/1993 | Maeyama et al. |
| 5,240,417 A | 8/1993 | Smithson et al. |
| 5,243,998 A | 9/1993 | Silverman et al. |
| 5,254,066 A | 10/1993 | Brown et al. |
| 5,256,115 A | 10/1993 | Scholder et al. |
| 5,277,678 A | 1/1994 | Friedebach et al. |
| 5,290,205 A | 3/1994 | Densmore et al. |
| 5,292,293 A | 3/1994 | Schumacher |
| 5,299,810 A | 4/1994 | Pierce et al. |
| 5,308,296 A | 5/1994 | Eckstein |
| 5,308,300 A | 5/1994 | Chino et al. |
| 5,313,942 A | 5/1994 | Platzker |
| 5,314,391 A | 5/1994 | Potash et al. |
| 5,318,487 A | 6/1994 | Golen et al. |
| 5,318,491 A | 6/1994 | Houston |
| D348,493 S | 7/1994 | Ashby |
| 5,328,420 A | 7/1994 | Allen |
| 5,328,422 A | 7/1994 | Nichols |
| 5,335,188 A | 8/1994 | Brisson |
| 5,352,166 A | 10/1994 | Chang |
| 5,361,091 A | 11/1994 | Hoarty et al. |
| 5,375,068 A | 12/1994 | Palmer et al. |
| 5,382,209 A | 1/1995 | Pasier et al. |
| 5,385,519 A | 1/1995 | Hsu et al. |
| 5,385,520 A | 1/1995 | Lepine et al. |
| 5,387,164 A | 2/1995 | Brown, Jr. |
| 5,403,252 A | 4/1995 | Leon et al. |
| 5,407,402 A | 4/1995 | Brown et al. |
| 5,410,471 A | 4/1995 | Alyfuku et al. |
| 5,410,472 A | 4/1995 | Anderson |
| 5,433,679 A | 7/1995 | Szymczak et al. |
| 5,435,799 A | 7/1995 | Lundin |
| 5,451,922 A | 9/1995 | Hamilton |
| 5,462,051 A | 10/1995 | Oka et al. |
| 5,462,503 A | 10/1995 | Benjamin et al. |
| 5,462,504 A | 10/1995 | Trulaske et al. |
| 5,466,200 A | 11/1995 | Ulrich et al. |
| 5,474,090 A | 12/1995 | Begun et al. |
| 5,484,389 A | 1/1996 | Stark et al. |
| 5,489,249 A | 2/1996 | Brewer et al. |
| 5,512,025 A | 4/1996 | Dalebout et al. |
| 5,527,239 A | 6/1996 | Abbondanza |
| 5,535,664 A | 7/1996 | Rokowski |
| 5,538,486 A | 7/1996 | France et al. |
| 5,546,324 A | 8/1996 | Palmer et al. |
| 5,547,439 A | 8/1996 | Rawls et al. |
| 5,572,643 A | 11/1996 | Judson |
| 5,577,981 A | 11/1996 | Jarvik |
| 5,584,779 A | 12/1996 | Knecht et al. |
| 5,590,128 A | 12/1996 | Maloney et al. |
| 5,591,104 A | 1/1997 | Andrus et al. |
| 5,598,849 A | 2/1997 | Browne |
| 5,600,310 A | 2/1997 | Whipple, III et al. |
| 5,605,336 A | 2/1997 | Gaoiran et al. |
| 5,619,412 A | 4/1997 | Hapka |
| 5,619,991 A | 4/1997 | Sloane |
| 5,626,539 A | 5/1997 | Piaget et al. |
| 5,645,509 A | 7/1997 | Brewer et al. |
| 5,645,513 A | 7/1997 | Haydocy et al. |
| 5,655,997 A | 8/1997 | Greenberg et al. |
| 5,663,951 A | 9/1997 | Danneels et al. |
| 5,667,459 A | 9/1997 | Su |
| 5,690,582 A | 11/1997 | Ulrich et al. |
| 5,690,852 A | 11/1997 | Saito et al. |
| 5,695,400 A | 12/1997 | Fennell, Jr. et al. |
| 5,697,834 A | 12/1997 | Heumann et al. |
| 5,702,323 A | 12/1997 | Poulton |
| 5,704,875 A | 1/1998 | Tanabe |
| 5,713,794 A | 2/1998 | Shimojima et al. |
| 5,720,771 A | 2/1998 | Snell |
| 5,722,418 A | 3/1998 | Bro |
| 5,738,612 A | 4/1998 | Tsuda |
| 5,743,833 A | 4/1998 | Watterson et al. |
| 5,749,372 A | 5/1998 | Allen et al. |
| 5,752,883 A | 5/1998 | Butcher et al. |
| 5,752,897 A | 5/1998 | Skowronski et al. |
| 5,754,765 A | 5/1998 | Danneels et al. |
| 5,759,199 A | 6/1998 | Snell et al. |
| 5,771,354 A | 6/1998 | Crawford |
| 5,777,678 A | 7/1998 | Ogata et al. |
| 5,779,596 A | 7/1998 | Weber |
| 5,785,630 A | 7/1998 | Bobick et al. |
| 5,785,631 A | 7/1998 | Heidecke |
| 5,810,696 A | 9/1998 | Webb |
| 5,813,864 A | 9/1998 | Ikuta |
| 5,836,770 A | 11/1998 | Powers |
| 5,838,906 A | 11/1998 | Doyle et al. |
| 5,845,230 A | 12/1998 | Lamberson |
| 5,854,833 A | 12/1998 | Hogan et al. |
| 5,857,939 A | 1/1999 | Kaufman |
| 5,865,733 A | 2/1999 | Malinouskas et al. |
| 5,873,369 A | 2/1999 | Laniado et al. |
| 5,880,677 A | 3/1999 | Lestician |
| 5,888,172 A | 3/1999 | Andrus et al. |
| 5,890,906 A | 4/1999 | Macri et al. |
| 5,890,995 A | 4/1999 | Bobick et al. |
| 5,905,442 A | 5/1999 | Mosebrook et al. |
| 5,909,544 A | 6/1999 | Anderson, II et al. |
| 5,910,070 A | 6/1999 | Henry et al. |

| | | |
|---|---|---|
| 5,911,132 A | 6/1999 | Sloane |
| 5,911,687 A | 6/1999 | Sato et al. |
| 5,916,063 A | 6/1999 | Alessandri |
| 5,917,405 A | 6/1999 | Joao |
| 5,929,748 A | 7/1999 | Odinak |
| 5,929,782 A | 7/1999 | Stark |
| 5,931,763 A | 8/1999 | Alessandri |
| 5,947,869 A * | 9/1999 | Shea .................. 482/8 |
| 5,956,509 A | 9/1999 | Kevner |
| 5,961,561 A | 10/1999 | Wakefield, II |
| 5,964,701 A | 10/1999 | Asada et al. |
| 5,967,975 A | 10/1999 | Ridgeway |
| 5,993,356 A | 11/1999 | Houston et al. |
| 5,995,868 A | 11/1999 | Dorfmeister et al. |
| 5,997,476 A | 12/1999 | Brown |
| 6,004,243 A | 12/1999 | Ewert |
| 6,010,451 A | 1/2000 | Clawson |
| 6,013,007 A | 1/2000 | Root et al. |
| 6,014,432 A | 1/2000 | Modney |
| 6,022,272 A | 2/2000 | Sano |
| 6,033,344 A | 3/2000 | Trulaske et al. |
| 6,042,519 A | 3/2000 | Shea |
| 6,050,822 A | 4/2000 | Faughn |
| 6,050,924 A | 4/2000 | Shea |
| 6,050,942 A | 4/2000 | Rust et al. |
| 6,053,737 A | 4/2000 | Babbitt et al. |
| 6,053,844 A | 4/2000 | Clem |
| 6,059,692 A | 5/2000 | Hickman |
| 6,066,075 A | 5/2000 | Poulton |
| 6,066,705 A | 5/2000 | Calderon et al. |
| 6,106,297 A | 8/2000 | Pollak et al. |
| 6,110,076 A | 8/2000 | Hurt |
| 6,132,337 A | 10/2000 | Krupka et al. |
| 6,132,340 A | 10/2000 | Wang et al. |
| 6,142,913 A | 11/2000 | Ewert |
| 6,148,262 A | 11/2000 | Fry |
| 6,152,854 A | 11/2000 | Carmein |
| 6,152,856 A | 11/2000 | Studor et al. |
| 6,162,151 A | 12/2000 | Tani et al. |
| 6,162,189 A | 12/2000 | Girone et al. |
| 6,171,186 B1 | 1/2001 | Kurosawa et al. |
| 6,171,218 B1 | 1/2001 | Shea |
| 6,193,631 B1 | 2/2001 | Hickman |
| 6,211,451 B1 | 4/2001 | Tohgi et al. |
| 6,231,481 B1 | 5/2001 | Brock |
| 6,231,482 B1 | 5/2001 | Thompson |
| 6,241,524 B1 | 6/2001 | Aoshima et al. |
| 6,244,987 B1 | 6/2001 | Ohsuga et al. |
| 6,244,988 B1 | 6/2001 | Delman |
| 6,251,048 B1 | 6/2001 | Kaufman |
| 6,283,896 B1 | 9/2001 | Grunfeld et al. |
| 6,312,363 B1 | 11/2001 | Watterson et al. |
| 6,322,451 B1 | 11/2001 | Miura |
| 6,356,856 B1 | 3/2002 | Damen et al. |
| 6,358,187 B1 | 3/2002 | Smith |
| 6,371,850 B1 | 4/2002 | Sonoda |
| 6,402,558 B1 | 6/2002 | Hung-Ju et al. |
| 6,450,922 B1 | 9/2002 | Henderson et al. |
| 6,458,060 B1 | 10/2002 | Watterson et al. |
| 6,463,385 B1 | 10/2002 | Fry |
| 6,464,618 B1 | 10/2002 | Shea |
| 6,475,115 B1 | 11/2002 | Candito et al. |
| 6,497,638 B1 | 12/2002 | Shea |
| 6,503,173 B2 | 1/2003 | Clem |
| 6,582,342 B2 | 6/2003 | Kaufman et al. |
| 6,585,622 B1 | 7/2003 | Shum et al. |
| 6,601,016 B1 | 7/2003 | Brown et al. |
| 6,605,020 B1 | 8/2003 | Huang |
| 6,605,038 B1 | 8/2003 | Teller et al. |
| 6,612,492 B1 | 9/2003 | Yen |
| 6,616,578 B2 | 9/2003 | Alessandri |
| 6,626,799 B2 | 9/2003 | Watterson et al. |
| 6,634,992 B1 | 10/2003 | Ogawa |
| 6,638,198 B1 | 10/2003 | Shea |
| 6,645,124 B1 | 11/2003 | Clem |
| 6,648,798 B2 | 11/2003 | Yoo |
| 6,648,802 B2 | 11/2003 | Ware |
| 6,659,916 B1 | 12/2003 | Shea |
| 6,659,946 B1 | 12/2003 | Batchelor et al. |
| 6,669,600 B2 * | 12/2003 | Warner .................. 482/8 |
| 6,687,535 B2 | 2/2004 | Hautala et al. |
| 6,689,057 B1 | 2/2004 | Shinsel et al. |
| 6,700,788 B2 | 3/2004 | Matsushita et al. |
| 6,702,719 B1 | 3/2004 | Brown et al. |
| 6,712,737 B1 | 3/2004 | Nusbaum |
| 6,736,759 B1 | 5/2004 | Stubbs et al. |
| 6,740,007 B2 | 5/2004 | Gordon et al. |
| 6,749,537 B1 | 6/2004 | Hickman |
| 6,783,482 B2 | 8/2004 | Oglesby et al. |
| 6,786,848 B2 | 9/2004 | Yamashita et al. |
| 6,790,178 B1 | 9/2004 | Mault et al. |
| 6,793,607 B2 | 9/2004 | Neil |
| 6,808,472 B1 * | 10/2004 | Hickman .................. 482/8 |
| 6,808,473 B2 | 10/2004 | Hisano et al. |
| 6,824,502 B1 | 11/2004 | Huang |
| 6,825,876 B1 | 11/2004 | Easwar et al. |
| 6,863,641 B1 | 3/2005 | Brown et al. |
| 6,866,613 B1 | 3/2005 | Brown et al. |
| 6,918,858 B2 | 7/2005 | Watterson et al. |
| 6,921,351 B1 | 7/2005 | Hickman |
| 6,976,624 B2 | 12/2005 | Hsiao |
| 6,991,586 B2 | 1/2006 | Lapcevic |
| 6,997,852 B2 | 2/2006 | Watterson et al. |
| 7,022,047 B2 | 4/2006 | Cohen et al. |
| 7,044,891 B1 | 5/2006 | Rivera |
| 7,056,265 B1 | 6/2006 | Shea |
| 7,060,006 B1 | 6/2006 | Watterson |
| 7,060,008 B2 | 6/2006 | Watterson et al. |
| 7,070,539 B2 | 7/2006 | Brown et al. |
| 7,072,789 B2 | 7/2006 | Vock et al. |
| 7,115,076 B2 | 10/2006 | Oglesby et al. |
| 7,128,693 B2 | 10/2006 | Brown et al. |
| 7,166,062 B1 | 1/2007 | Watterson et al. |
| 7,166,064 B2 | 1/2007 | Watterson et al. |
| 7,254,516 B2 | 8/2007 | Case, Jr. et al. |
| 7,350,787 B2 | 4/2008 | Voss |
| 7,354,380 B2 | 4/2008 | Volpe, Jr. |
| 7,455,622 B2 | 11/2008 | Watterson et al. |
| 7,510,509 B2 | 3/2009 | Hickman |
| 7,537,546 B2 | 5/2009 | Watterson et al. |
| 7,549,947 B2 | 6/2009 | Hickman et al. |
| 7,556,590 B2 | 7/2009 | Watterson et al. |
| 7,575,536 B1 | 8/2009 | Hickman |
| 7,625,315 B2 | 12/2009 | Hickman |
| 7,628,730 B1 | 12/2009 | Watterson et al. |
| 7,637,847 B1 | 12/2009 | Hickman |
| 7,645,212 B2 | 1/2010 | Ashby et al. |
| 7,645,213 B2 | 1/2010 | Watterson et al. |
| 7,713,171 B1 | 5/2010 | Hickman |
| 7,789,800 B1 | 9/2010 | Watterson et al. |
| 2002/0042328 A1 | 4/2002 | Yoo |
| 2002/0055422 A1 | 5/2002 | Airmet et al. |
| 2004/0012335 A1 | 1/2004 | Shon et al. |
| 2004/0127335 A1 | 7/2004 | Watterson et al. |
| 2004/0162189 A1 | 8/2004 | Hickman |
| 2005/0233859 A1 | 10/2005 | Takai et al. |
| 2005/0233861 A1 | 10/2005 | Hickman |
| 2005/0261609 A1 | 11/2005 | Collings et al. |
| 2005/0272564 A1 | 12/2005 | Pyles et al. |
| 2006/0063645 A1 | 3/2006 | Chiang |
| 2006/0205566 A1 | 9/2006 | Watterson et al. |
| 2006/0205569 A1 | 9/2006 | Watterson et al. |
| 2006/0281603 A1 | 12/2006 | Hickman |
| 2007/0265138 A1 | 11/2007 | Ashby |
| 2008/0051256 A1 | 2/2008 | Dalebout et al. |
| 2008/0300110 A1 | 12/2008 | Smith |
| 2009/0209393 A1 | 8/2009 | Crater et al. |
| 2009/0258758 A1 | 10/2009 | Hickman |
| 2009/0270226 A1 | 10/2009 | Watterson et al. |
| 2009/0270227 A1 | 10/2009 | Ashby et al. |
| 2010/0248900 A1 | 9/2010 | Ashby et al. |

FOREIGN PATENT DOCUMENTS

| | | |
|---|---|---|
| CN | 2449755 | 9/2001 |
| DE | 4100559 | 7/1991 |
| EP | 0199442 | 10/1986 |
| JP | H10-243979 | 9/1998 |
| WO | WO8101507 | 6/1991 |

| | | |
|---|---|---|
| WO | WO9417860 | 8/1994 |
| WO | WO9638205 | 12/1996 |
| WO | WO9800204 | 1/1998 |
| WO | WO9832496 | 7/1998 |
| WO | WO 2007/081607 | 7/2007 |

OTHER PUBLICATIONS

Notice of Allowance and Fee(s) Due dated Jun. 25, 2010, 4 pages, U.S. Appl. No. 11/315,682.
Supplemental Notice of Allowability dated Jul. 16, 2010, 2 pages, U.S. Appl. No. 11/315,682.
Notice of Allowance and Fee(s) Due, date mailed Jul. 12, 2010, 4 pages, U.S. Appl. No. 12/467,776.
Notice of Allowance and Fee(s) Due, date mailed Sep. 21, 2010, 4 pages, U.S. Appl. No. 12/467,776.
Notice of Allowance and Fee(s) Due, date mailed Sep. 30, 2010, 6 pages, U.S. Appl. No. 12/489,031.
Restriction Requirement dated May 13, 2010, 6 pages, U.S. Appl. No. 12/413,362.
Non-Final Office Action dated Aug. 26, 2010, 11 pages, U.S. Appl. No. 12/413,362.
Non-Final Office Action dated Sep. 2, 2010, 13 pages, U.S. Appl. No. 12/413,330.
Notice of Allowance and Fee(s) Due dated Feb. 19, 2010, 27 pages, U.S. Appl. No. 11/314,133.
Notice of Allowance and Fee(s) Due dated Feb. 19, 2010, 4 pages, U.S. Appl. No. 11/315,682.
Supplemental Notice of Allowability, dated Apr. 21, 2010, 2 pages, U.S. Appl. No. 11/315,682.
Non-Final Office Action dated Feb. 22, 2010, 5 pages, U.S. Appl. No. 12/467,776.
Notice of Allowance and Fee(s) Due dated Feb. 12, 2010, 8 pages, U.S. Appl. No. 11/657,701.
Non-Final Office Action dated Apr. 20, 2010, 6 pages, U.S. Appl. No. 12/489,031.
Final Office Action dated Mar. 12, 2010, 7 pages, U.S. Appl. No. 11/849,068.
Notification of the First Office Action issued on Jun. 12, 2009 by the State Intellectual Property Office of the People's Republic of China for Chinese Patent Application No. 200680048743.X, which was nationalized from and claims priority to PCT Publication No. WO 2007/081607, 19 pages (including original Chinese version and English translation.
Text of the Response to First Office Action and Amended Claims for the first Office Action, submitted Oct. 26, 2009 to the State Intellectual Property Office of the People's Republic of China for Chinese Patent Application No. 200680048743.X, which was nationalized from and claims priority to PCT Publication No. WO 2007/081607, 17 pages (including original Chinese version and English translation).
Notification of the Second Office Action issued on Dec. 25, 2009 by the State Intellectual Property Office of the People's Republic of China for Chinese Patent Application No. 200680048743.X, which was nationalized from and claims priority to PCT Publication No. WO 2007/081607, 10 pages (including original Chinese version and English translation).
Notice of Allowance and Fees Due, 4 pages, U.S. Appl. No. 11/314,133, mailed May 10, 2010.
Notice of Allowance and Fees Due, 4 pages, U.S. Appl. No. 11/315,682, mailed May 13, 2010.
Notice of Allowance and Fees Due, 4 pages, U.S. Appl. No. 12/467,776, mailed Jun. 7, 2010.
The Fitlinxx Interactive Fitness Network™, Integrated Fitness Corp., brochure, 1998.
The Fitlinxx Interactive Fitness Network™, The Difference Between Surviving and Thriving May Be As Simple as Fitlinxx™, Integrated Fitness Corp., brochure, 1998.
Forbes Digital Tool: Startups, Sweat.equity, www.forbes.com, Feb. 1998.
Netpulse, Networkingout—Coming Distractions: Netpulse Helps Exercisers Surf the Net at the Gym, Accomplish Several Goals at Once, www.netpulse.com, Apr. 1998.

Netpulse, Instead of having an equipment repair technician traveling oer hill and dale, you may soon have equipment repaired via the internet, www.netpulse.com, Jul. 1998.
Netpulse, Infotech is supposed to make life easier-remember? Here's how to be sure it does., www.netpulse.com, Aug. 1998.
Netpulse, Exercise station connects to the Net, Now you can sweat to the Net, www.netpulse.com, Sep. 1998.
Netpulse, New Fitness Equipment Combines Internet, Sweat, Now you can surf and sweat, www.netpulse.com, Jan. 1999.
Netpulse, Hop In, Log On and Sweat, Netpulse exercise machines are the latest Web feat, www.netpulse.com, Feb. 1999.
Netpulse Club Watch™, Internet Powered Service, brochure, Apr. 1999.
Netpulse, State of the Art, www.netpulse.com, Feb. 2000.
Netpulse, Netpulse Files for Patents on its Pioneering Technology Inventions and Groundbreaking Business Methods in the Media and Fitness Markets, www.netpulse.com, May 2000.
Little Tony, One on One Video Trainer (for Model No. T1T123040), Jun. 1995 (25 pages).
Men's Journal, Squat.com The Home Gym Goes Online, May 2000 (2 pages).
MSNBC.com, Smart Fitness Section, On A Quest for Fitness—The Latest Workout Gear and Gadgets, Feb. 29, 2000 (6 pages).
Options Manual: Video Track/Track Five/Personal Trainer Plus (Part No. 109917) cited as "Options"), Sep. 1992 (2 pages).
PR Newswire, Turn Your Treadmill Into a Internet Appliance with www.iFIT.com, Oct. 19, 1999 (3 pages).
Pro-Form 8.0 TXP Manual (for Model No. PF080010) (cited as "8.0 TXP") Nov. 1991 (16 pages).
The Boston Globe, Living Section, p. F1, Wired Workout Local Gyms, Mar. 11, 2000 (2 pages).
The Herald Journal, People in Business, ICON winds Awards, vol. 91, No. 128, May 7, 2000 (1 page).
US Weekly, p. 71, Work Out Online, Mar. 27, 2000 (2 pages).
Communications of the ACM, vol. 35, No. 6, cited as "Comm of the ACM", Jun. 1992 (10 pages).
Ebsco Publishing, New Home Exercise Equipment: Your Computer?, Jun. 2000 (3 pages).
Fortune Magazine, p. 84, Virtual Workouts—Treadmills Possessed, Apr. 17, 2000 (2 pages).
Good Housekeeping, p. 53, A Run for the Money, Feb. 2000 (2 pages).
IEEE Publication, A Telerobotics Construction Set with Integrated Performance Analysis, 0-8186-7108-4/95 (IEEE) (cited as "Telerobotic Con."), Apr. 1995 (7 pages).
IEEE Publication, Intelligent Monitoring System for Limited System for Limited Communication Path: Telerobotic Task Execution over Internet, 0-8186-7108-4/95 (IEEE) (cited as "Intelligent"), Apr. 1995 (6 pages).
Lifestyler 10.0 ESP Manual (for Model No. 297052) (cited as "10.0 ESP"), Nov. 1992 (16 pages).
1994 Pro-Form First in Fitness, (1994 Copyright ProForm Products, Inc.), (16 pages).
Consumer Reports, Out of the Rat Race, Onto a Treadmill, Feb. 2000 (5 pages).
Consumer Reports, Out of the Rat Race, Onto a Treadmill at http://www.accessmylibrary.com/coms2/summaryU0286-28004514_ITM, Mar. 5, 2007, 8 pages.
Exergaming, en.wikipedia.org, printed Oct. 1, 2007.
Wired, www.wired.com, issue 2.09, Sep. 1994.
"Defendant's Amended Invalidity Contentions," Case No. 2:05-cv-527, signed by Kirk Harris on Mar. 16, 2007.
"Icon Health & Fitness Inc.'s Supplemental Preliminary Invalidity Contentions," Case No. 2-05-cv-527, signed by Brent A. Hansen on Jun. 23, 2006.
"Icon Health & Fitness Inc.'s Preliminary Invalidity Contentions," Case No. 2-05-cv-527, signed by Brent A. Hansen on Jun. 26, 2006.
"Expert Report of Dr. Brent Nelson Pursuant to Federal Rule of Civil Procedure 26(a)(2)(B)," Mar. 13, 2007.
"Netpulse Brings Free Internet Access to Fitness Centers." Newsbytes.com, http://www.newsbytes.com, Jan. 17, 2000.
"Precor and Netpulse Partner to Create the World's First Internet Powered Elliptical." Netpulse press release, Oct. 1, 2999.

Surf While you Sweat.: ABCNEWS.com, Oct. 27, 1998.
"The Best Products of 1999- Business Week's Top Picks of the Most Innovative Products on the Market." Business Week, Dec. 6, 1999.
Netpulse brocure. "Catch the wwwave," available on information and belief at least as early as Feb. 10, 2000.
Winkler, William J., "Pumping Iron With a Digital Friend," Business Week, Dec. 18, 1995, pp. 78a.
Internet Archive Wayback Machine, archive for www.ifit.com, at http://web.archive,org/web/*/www.ifit.com, Sep. 1, 2003.
iFIT.com "Internet Workouts Control Your Treadmill, Bike, or Elliptical," at http://www.ifit.com, Sep. 1, 2003.
Icon Health and Fitness, Nordictrack C2420 (Model No. NTL 14950), 2004.
ICON Health and Fitness, Nordictrack C2420 (Model No. NTL 14951), 2004.
ICON Health and Fitness, Nordictrack C2420 (Model No. NTL 1495.2), 2004.
ICON Health and Fitness, Nordictrack CX 990 (Model No. NEL 09940), 2003.
ICON Health and Fitness, Nordictrack SL 760 (Model No. NTC 89021), 2004.
ICON Health and Fitness, Nordictrack SL 760 (Model No. NTC 89020), 2004.
ICON Health and Fitness, Nordictrack SL 710 (Model No. NTC 07942), 2004.
ICON Health and Fitness, Nordictrack SL 710 (Model No. NTC 07941), 2004.
ICON Health and Fitness, Nordictrack SL 710 (Model No. NTC 07940), 2003.
ICON Health and Fitness, Nordictrack SL 705 (Model No. NTC 05941), 2004.
ICON Health and Fitness, Nordictrack SL 705 (Model No. NTC 05940), 2004.
ICON Health and Fitness, Nordictrack C2420 Manual preceding Specs, 2004.
ICON Health and Fitness, Pro-Form Personal Trainer Plus, available on information and belief at least as early as Jul. 2006.
ICON Health and Fitness, Screenshots of iFit.com, available on information and belief at least as early as Jul. 2006.
ICON Health and Fitness, iFit.com "Log on. Work out." Brochure, 2000.
ICON Health and Fitness, Website printouts (archived docs), 2000.
ICON Health and Fitness, Pro-Form 600 (Model No. PETL60000), 2000.
ICON Health and Fitness, Reebok ACD1 (Model No. RETL11900), 2000.
ICON Health and Fitness, Reebok RT1000 (Model No. RETL16001), 2001.
ICON Health and Fitness, One-on-One Video Trainer (Model No TLTL21040), 1995.
IEEE Computer Graphics and Applications- EVAC: A Virtual Environment for Control of Remote Imaging Instrumentation, 1996.
IEEE: Performance Analysis of a Gateway Connecting the Cebus to the ISDN, 1993.
Fitness Equipment: Cardio, 1997.
ICON-CYB 034253-034286 and 034323-034328, containing photographs of various fitness equipment systems, 1989-1996, 40 pages.
Mademoiselle, www.iFIT.com, Mademoiselle, Mar. 2000.
Wired, ICON Health and Fitness Image 10.4Qi, Wired, Apr. 2000.
Cooking Light, Cybertrainers are Watching Your Workout, Cooking Light, Aug. 2000.
Villarosa, A Fitness Industry, With Gadgets Galore, the New York Times, Apr. 25, 2000.
Little, Web Creates Workouts With Virtual Trainers, The Birmingham News, Apr. 10, 2000.
San Francisco Chronicle, Let the Web Help You Get Physical, Mar. 16, 2000.
"Workouts that Work," Consumer Reports, pp. 31-39, available on information and belief at least as early as Jan. 1999, 9 pages.
New Balance Fitness Equipment advertisement, Runners World, Feb. 2006, 1 page.
New Balance Fitness Equipment advertisement (with sport block dumbbell advertisement), Runners World, Mar. 2006, 1 page.

T Series T3/T5 Treadmill Operation Manual, copyright 2001, Life Fitness, 30 pages.
Advertisement, "We Just Made Buying a Trackmaster 100% Easier," Athletic Business, Oct. 1991, 2 pages.
Advertisement, "Trackmaster TM500E Treadmill Features Interactive Controller," Athletic Business, Oct. 1991, 1 page.
Advertisement, "Survival Equipment for the New Age," Athletic Business, Oct. 1991, p. 60.
Advertisement, "Introducing the LifeStep Model 9500-We've Made the Best Even Better," Athletic Business, Sep. 1991, 1 page.
Advertisement, "We Just Made Buying a Trackmaster 100% Easier," Athletic Business, Sep. 1991, 2 pages.
Trackmaster Online: Treadmill Controllers: http://web.archive.org/web/20010124093300/www.trackmastertreadmills.com/contrlr.html, available on information and belief at least as early as Jan. 2001, 1 page.
Transcript of Deposition of Michael Benjamin, taken Apr. 11, 2007, from *Cybergym Research, LLC* v. *ICON Health & Fitness*, et al., in the Eastern District of Texas, Marshal Division, Case No. 2:05-cv-527 DF, 33 pages.
Michael Benjamin Computation Book, dated Nov. 2, 1991, 14 pages.
TECTRIX Fitness Equipment, VR Bike Owners Manual, Jan. 1995, 19 pages.
TECTRIX Fitness Equipment, VR Bike Maintenance and Repair manual, Mar. 1997, 55 pages.
TECTRIX Fitness Equipment, Photographs of VR Bike, available on information and belief at least as early as 1994, 13 pages.
Tectrix, Tectrix Fitness Equipment History, Jim Sweeney, Jun. 20, 1996, 4 pages.
TECTRIX Fitness Equipment, Are We Having Fun Yet? brochure, 1995, 4 pages.
First For Women, No More Bicycle Boredom, Oct. 3, 1994, 2 pages.
Sports Illustrated, Software for Hardbodies, Sep. 19, 1994, 2 pages.
Cybergear, Inc., CyberGear 1000 brochure, which was available, on information and belief, at least as early as 1994, 2 pages.
National Fitness Trade Journal cover, Fall 1995, 1 page.
TECTRIX Fitness Equipment, The Body The Brain The Passion The Will product brochure, circa 1998, 24 pages.
Leisure Management, Going Downhill, Virtually, vol. 14, No. 8, Aug. 1994, 2 pages.
TECTRIX Fitness Equipment, Sweeney Town from CyberGear for the Tectrix VRBike brochure, which was available, on information and belief, at least as early as 1994, 2 pages.
"Virtual Treadmill Takes Users Anywhere They Want to Go," http://www.ksl.com/?nid=148&sid=6920538, Jun. 24, 2009, 2 pages.
DVD labeled "iFIT.com Media Coverage News Clips Ver. 3.0," dated Mar. 30, 2000.
DVD Labeled "ICON-CYB001" 881 PDF Files Jun. 12, 2006.
CD-ROM Labeled "Supershow 2000," ICON-CYB 034309 Highlight Video Apr. 20, 2006.
CD-ROM Labeled "Supershow 1998," ICON-CYB 034310 Live Video Streaming from Logan, Utah to Atlanta, Georgia, Feb. 10, 1998.
DVD Labeled "1998 Supershow Web Cast," ICON-CYB 034311 Raw video footage, Jun. 2006.
CD-ROM Labeled "Steve Young Webcast," ICON-CYB 034312, Sales Meeting 2000, Jun. 2006.
DVD labeled "Tectrix VR Bike videos, including: 1) Media Coverage News Clips of Tectrix VR Bike, dated Jun. 15, 1994, 11 minutes, 19 seconds; 2) Video demonstrating use of CyberGEAR exercise bike, which was available, on information and belief, at least as early as 1994, 5 minutes, 39 seconds; and 3) Video demonstrating use of Tectrix VR Bike, which was available, on information and belief, at least as early as 1994, 4 minutes, 43 seconds".
Office Action dated Sep. 11, 2000, 3 pages, U.S. Appl. No. 09/349,608.
Notice of Allowance and Issue Fee Due, date mailed Jul. 25, 2001, 2 pages, U.S. Appl. No. 09/349,608.
Notice of Allowance and Fee(s) Due, date mailed Sep. 20, 2004, 7 pages, U.S. Appl. No. 09/641,627.
Restriction Requirement dated Apr. 29, 2005, 4 pages, U.S. Appl. No. 09/641,627.

Office Action dated Jul. 26, 2005, 4 pages, U.S. Appl. No. 09/641,627.
Notice of Allowance and Fee(s) Due, date mailed Feb. 3, 2006, 4 pages, U.S. Appl. No. 09/641,627.
Notice of Allowance and Fee(s) Due, dated Sep. 1, 2006, 4 pages, U.S. Appl. No. 09/641,627.
Notice of Allowance and Fee(s) Due, dated Aug. 8, 2008, 4 pages, U.S. Appl. No. 11/429,858.
Notice of Allowance and Fee(s) Due, dated Jun. 4, 2008, 8 pages, U.S. Appl. No. 11/429,858.
Restriction Requirement dated Apr. 17, 2007, 5 pages, U.S. Appl. No. 11/429,858.
Office Action dated Aug. 22, 2007, 5 pages, U.S. Appl. No. 11/429,858.
Restriction Requirement dated Feb. 5, 2008, 8 pages, U.S. Appl. No. 11/429,858.
Notice of Allowance and Fees(s) Due dated Jun. 18, 2009, 7, pages, U.S. Appl. No. 12/276,900.
Notice of Allowance and Fee(s) Due dated Nov. 2, 2009, 4 pages, U.S. Appl. No. 12/276,900.
Restriction Requirement dated Sep. 23, 2003, 4 pages, U.S. Appl. No. 09/641,600.
Office Action dated Feb. 11, 2004, 4 pages, U.S. Appl. No. 09/641,600.
Notice of Allowance and Fee(s) Due, date mailed Jun. 2, 2004, 4 pages, U.S. Appl. No. 09/641,600.
Office Action dated Feb. 15, 2005, 7 pages, U.S. Appl. No. 09/641,600.
Notice of Allowance and Fee(s) Due, date mailed Sep. 14, 2005, 4 pages, U.S. Appl. No. 09/641,600.
Office Action dated Dec. 18, 2001, 3 pages, U.S. Appl. No. 09/641,220.
Notice of Allowance and Fee(s) Due, date mailed Jul. 1, 2002, 5 pages, U.S. Appl. No. 09/641,220.
Office Action dated Jun. 29, 2004, 3 pages. U.S. Appl. No. 09/776,410.
Notice of Allowance and Fee(s) Due, date mailed Nov. 12, 2004, 4 pages, U.S. Appl. No. 09/776,410.
Notice of Allowance and Fee(s) Due, date mailed Apr. 18, 2005, 5 pages, U.S. Appl. No. 09/776,410.
Notice of Allowance and Fee(s) Due dated Oct. 30, 2009, 4 pages, U.S. Appl. No. 10/856,676.
Notice of Allowance and Fee(s) Due dated Jul. 10, 2009, 4 pages. U.S. Appl. No. 10/856,676.
Notice of Allowance dated Feb. 12, 2009, 4 pages, U.S. Appl. No. 10/856,676.
Notice of Allowance and Fee(s) Due dated Dec. 30, 2008, 8 pages, U.S. Appl. No. 10/856,676.
Notice of Allowance and Fee(s) Due dated Oct. 2, 2008, 8 pages, U.S. Appl. No. 10/856,676.
Office Action dated May 6, 2008, 7 pages, U.S. Appl. No. 10/856,676.
Restriction Requirement dated Oct. 9, 2007, 5 pages, U.S. Appl. No. 10/856,676.
Office Action dated Jan. 24, 2008, 5 pages, U.S. Appl. No. 10/856,676.
Restriction Requirement dated Aug. 14, 2009, 6 pages, U.S. Appl. No. 11/314,133.
Office Action dated Jul. 16, 2009, 8 pages, U.S. Appl. No. 11/315,682.
Office Action dated Sep. 29, 2009 6 pages, U.S. Appl. No. 11/315,682.
Restriction Requirement dated Jul. 1, 2003, 4 pages, U.S. Appl. No. 09/947,193.
Office Action dated Oct. 23, 2003, 4 pages, U.S. Appl. No. 09/947,193.
Notice of Allowance and Fee(s) Due, date mailed May 14, 2004, 4 pages, U.S. Appl. No. 09/947,193.
Office Action dated Sep. 15, 2005, 5 pages, U.S. Appl. No. 09/947,193.
Notice of Allowance and Fee(s) Due, date mailed Jan. 26, 2006, 5 pages, U.S. Appl. No. 09/947,193.
Notice of Allowance and Fee(s) Due, date mailed Aug. 16, 2006, 4 pages, U.S. Appl. No. 09/947,193.
Restriction Requirement dated Mar. 26, 2007, 5 pages, U.S. Appl. No. 11/429,725.
Office Action dated Jun. 6, 2007, 5 pages, U.S. Appl. No. 11/429,725.
Restriction Requirement dated Nov. 14, 2007, 5 pages, U.S. Appl. No. 11/429,725.
Final Office Action dated Feb. 28, 2008, 8 pages, U.S. Appl. No. 11/429,725.
Notice of Allowance and Fee(s) Due dated Jun. 4, 2008, 9 pages, U.S. Appl. No. 11/429,725.
Notice of Allowance and Fee(s) Due dated Sep. 8, 2008, 4 pages, U.S. Appl. No. 11/429,725.
Supplemental Notice of Allowance dated Jan. 30, 2009, 2 pages, U.S. Appl. No. 11/429,725.
Supplemental Notice of Allowance dated May 5, 2009, 2 pages, U.S. Appl. No. 11/429,725.
Restriction Requirement dated Sep. 21, 2004, 4 pages, U.S. Appl. No. 10/106,842.
Office Action dated Nov. 12, 2004, 4 pages, U.S. Appl. No. 10/106,842.
Notice of Allowance and Fee(s) Due, date mailed Mar. 14, 2005, 6 pages, U.S. Appl. No. 10/106,842.
Notice of Allowance and Fee(s) Due, date mailed Mar. 29, 2006, 6 pages, U.S. Appl. No. 11/132,740.
Notice of Allowance and Fee(s) Due, date mailed Jun. 30, 2003, 5 pages, U.S. Appl. No. 09/933,701.
Restriction Requirement dated Aug. 22, 2006, 5 pages, U.S. Appl. No. 10/674,911.
Office Action dated Dec. 12, 2006, 7 pages, U.S. Appl. No. 10/674,911.
Restriction Requirement dated Jul. 2, 2007, 5 pages, U.S. Appl. No. 10/674,911.
Office Action dated Nov. 28, 2007, 8 pages, U.S. Appl. No. 10/674,911.
Office Action dated Apr. 22, 2008, 10 pages, U.S. Appl. No. 10/674,911.
Office Action dated Aug. 18, 2008, 9 pages, U.S. Appl. No. 10/674,911.
Notice of Allowance and Fee(s) Due, date mailed Jan. 28, 2009, 15 pages, U.S. Appl. No. 10/674,911.
Office Action dated Jun. 27, 2008, 13 pages, U.S. Appl. No. 11/833,070.
Office Action dated Oct. 31, 2008, 23 pages, U.S. Appl. No. 11/833,070.
Office Action dated Jun. 16, 1997, 4 pages, U.S. Appl. No. 08/766,513.
Office Action dated Feb. 17, 1998, 5 pages, U.S. Appl. No. 08/766,513.
Notice of Allowance and Issue Fee Due, date mailed Sep. 22, 1998, 3 pages, U.S. Appl. No. 08/766,513.
Response to Rule 312 Communication, dated Jun. 2, 1999, 2 pages, U.S. Appl. No. 08/766,513.
Office Action dated Dec. 10, 1999, 3 pages, U.S. Appl. No. 09/273,591.
Notice of Allowance and Fee(s) Due, date mailed Jul. 14, 2000, 2 pages, U.S. Appl. No. 09/273,591.
Office Action dated Dec. 18, 2001, 3 pages, U.S. Appl. No. 09/690,701.
Office Action dated Sep. 25, 2002, 4 pages, U.S. Appl. No. 09/690,701.
Final Office Action dated Mar. 26, 2003, 4 pages, U.S. Appl. No. 09/690,701.
Advisory Action dated Jun. 16, 2003, 2 pages, U.S. Appl. No. 09/690,701.
Notice of Allowance and Fee(s) Due, date mailed Nov. 24, 2003, 5 pages, U.S. Appl. No. 09/690,701.
Restriction Requirement dated Dec. 29, 2004, 4 pages, U.S. Appl. No. 10/729,356.
Office Action dated Feb. 16, 2005, 5 pages, U.S. Appl. No. 10/729,356.
Restriction Requirement dated Feb. 21, 2006, 5 pages, U.S. Appl. No. 10/729,356.

Notice of Allowance and Fee(s) Due, date mailed Jun. 13, 2006, 6 pages, U.S. Appl. No. 10/729,356.
Response to Rule 312 Communication, dated Jul. 30, 2007, 2 pages, U.S. Appl. No. 10/729,356.
Office Action dated Jan. 14, 2008, 7 pages, U.S. Appl. No. 10/729,356.
Office Action dated Jul. 1, 2008, 9 pages, U.S. Appl. No. 10/729,356.
Notice of Allowance and Fee(s) Due, date mailed Mar. 19, 2009, 7 pages, U.S. Appl. No. 10/729,356.
Office Action dated Jan. 24, 2005, 4 pages, U.S. Appl. No. 10/773,617.
Notice of Allowance and Fee(s) Due, date mailed Apr. 17, 2006, 4 pages, U.S. Appl. No. 10/773,617.
Notice of Allowance and Fee(s) Due, date mailed Jul. 6, 2006, 4 pages, U.S. Appl. No. 10/773,617.
Office Action dated May 16, 2007, 4 pages, U.S. Appl. No. 10/773,617.
Office Action dated Jan. 24, 2008, 8 pages, U.S. Appl. No. 10/773,617.
Final Office Action dated Apr. 24, 2008, 10 pages, U.S. Appl. No. 10/773,617.
Office Action dated Oct. 16, 2008, 9 pages, U.S. Appl. No. 10/773,617.
Notice of Allowance and Fee(s) Due dated May 29, 2009, 4 pages, U.S. Appl. No. 10/773,617.
Office Action dated Jun. 26, 2008, 4 pages, U.S. Appl. No. 11/440,703.
Notice of Allowance and Fee(s) Due dated Dec. 17, 2008, 8 pages, U.S. Appl. No. 11/440,703.
Office Action dated Jun. 13, 2008, 6 pages, U.S. Appl. No. 11/657,701.
Office Action dated Jan. 6, 2009, 8 pages, U.S. Appl. No. 11/657,701.
Office Action dated Apr. 16, 2009, 7 pages, U.S. Appl. No. 11/657,701.
Final Office Action dated Sep. 24, 2009, 11 pages, U.S. Appl. No. 11/657,701.
Office Action dated Dec. 18, 2001, 3 pages, U.S. Appl. No. 09/690,178.
Notice of Allowance and Fee(s) Due, date mailed Sep. 23, 2002, 5 pages, U.S. Appl. No. 09/690,178.
Office Action dated Mar. 7, 2003, 4 pages, U.S. Appl. No. 09/690,178.
Notice of Allowance and Fee(s) Due, date mailed Nov. 24, 2003, 4 pages, U.S. Appl. No. 09/690,178.
Response to Rule 312 Communication, dated Jan. 21, 2004, 2 pages, U.S. Appl. No. 09/690,178.
Office Action dated Jan. 27, 2005, 6 pages, U.S. Appl. No. 10/751,334.
Final Office Action dated Aug. 25, 2005, 6 pages, U.S. Appl. No. 10/751,334.
Notice of Allowance and Fee(s) Due, date mailed Jun. 12, 2006, 4 pages, U.S. Appl. No. 10/751,334.
Restriction Requirement dated Apr. 17, 2007, 5 pages, U.S. Appl. No. 10/751,334.
Restriction Requirement dated Aug. 9, 2007, 5 pages, U.S. Appl. No. 10/751,334.
Office Action dated Jan. 25, 2008, 7 pages, U.S. Appl. No. 10/751,334.
Office Action dated Jun. 2, 2008, 7 pages U.S. Appl. No. 10/751,334.
Office Action dated Nov. 25, 2008, 6 pages U.S. Appl. No. 10/751,334.
Notice of Allowance and Fee(s) Due dated Jun. 1, 2009, 7 pages, Office Action dated Jun. 1, 2008, 7 pages U.S. Appl. No. 10/751,334.
Office Action dated Jun. 15, 2004, 4 pages, U.S. Appl. No. 10/045,619.
Notice of Allowance and Fee(s) Due, date mailed Mar. 14, 2005, 4 pages, U.S. Appl. No. 10/045,619.
Restriction Requirement dated Jul. 27, 2006, 5 pages, U.S. Appl. No. 11/150,914.
Restriction Requirement dated Oct. 18, 2006, 5 pages, U.S. Appl. No. 11/150,914.
Office Action dated Feb. 22, 2007, 6 pages, U.S. Appl. No. 11/150,914.
Final Office Action dated Dec. 12, 2007, 8 pages, U.S. Appl. No. 11/150,914.
Advisory Action dated Feb. 7, 2008, 3 pages, U.S. Appl. No. 11/150,914.
Restriction Requirement dated Apr. 28, 2008, 6 pages, U.S. Appl. No. 11/150,914.
Office Action dated Dec. 31, 2008, 7 pages, U.S. Appl. No. 11/150,914.
Notice of Allowance and Fee(s) Due, date mailed Apr. 15, 2009, 5 pages, U.S. Appl. No. 11/150,914.
Office Action dated Aug. 18, 2008, 6 pages, U.S. Appl. No. 11/150,914.
Office Action dated May 1, 2008, 4 pages, U.S. Appl. No. 11/849,068.
Office Action dated Aug. 21, 2008, 6 pages, U.S. Appl. No. 11/849,068.
Office Action dated Apr. 16, 2009, 7 pages, U.S. Appl. No. 11/849,068.
Restriction Requirement dated Dec. 10, 2008, 6 pages, U.S. Appl. No. 11/849,068.

* cited by examiner

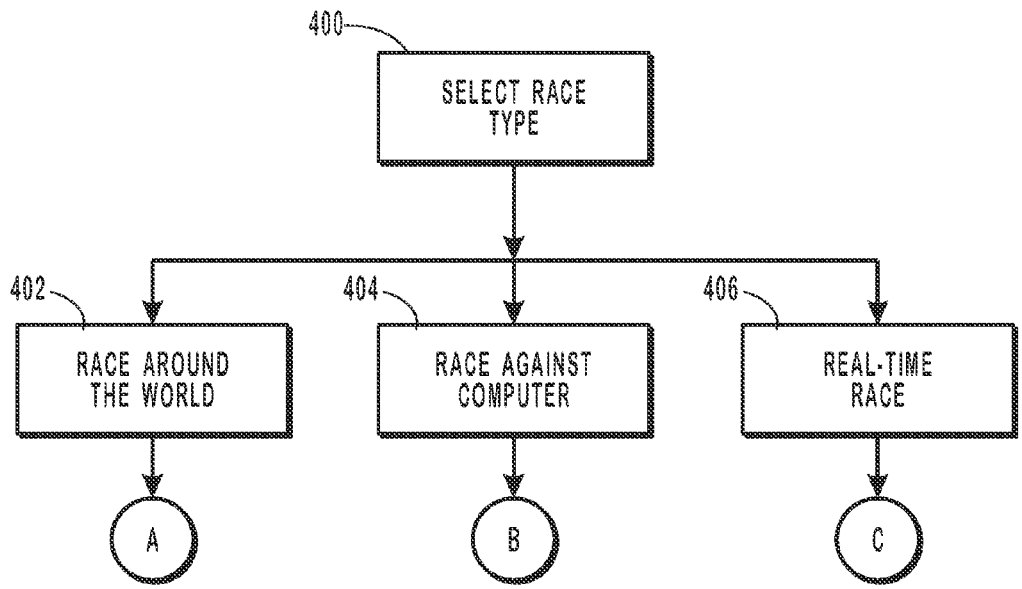
FIG. 17A
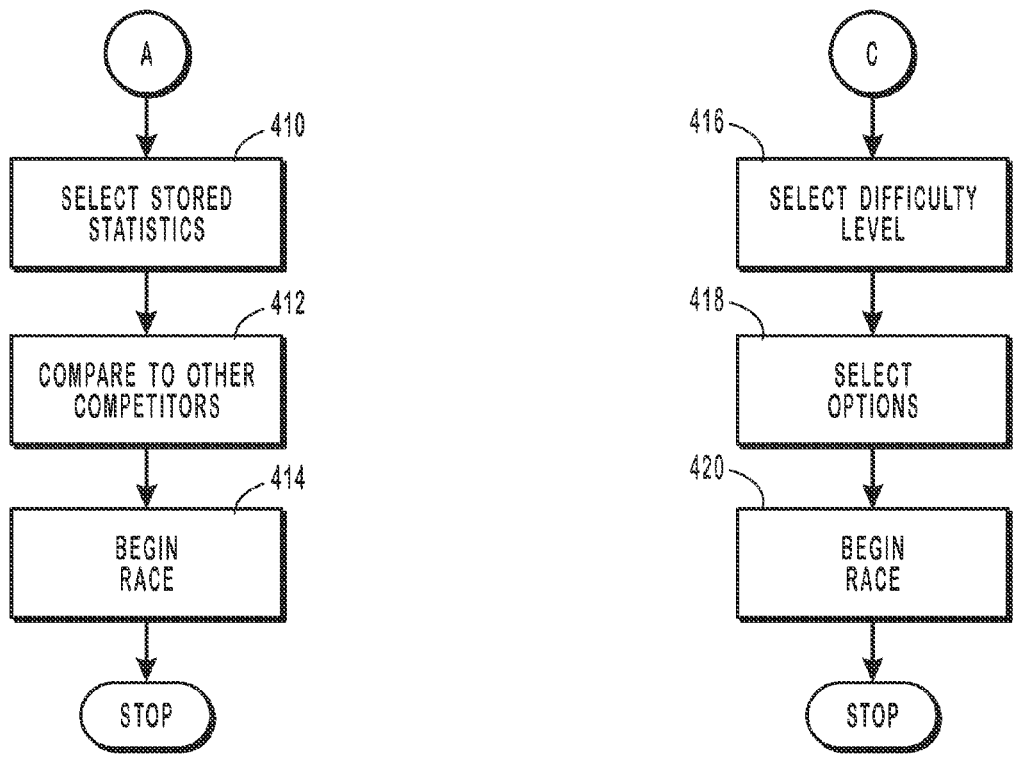
FIG. 17B
FIG. 17C

SYSTEMS FOR INTERACTION WITH EXERCISE DEVICE

RELATED PATENT APPLICATIONS

This application is a Continuation application of U.S. patent application Ser. No. 12/276,900, filed Nov. 24, 2008 now U.S. Pat. No. 7,645,213, entitled "Systems for Interaction with Exercise Device," which is incorporated herein by reference in its entirety and which is a Continuation application of U.S. patent application Ser. No. 11/429,858, filed May 8, 2006, entitled "Systems for Interaction with Exercise Device," now U.S. Pat. No. 7,455,622, which is incorporated herein by reference in its entirety and which is a Divisional application of U.S. patent application Ser. No. 09/641,627, filed Aug. 18, 2000, entitled "Systems for Interaction with Exercise Device," now U.S. Pat. No. 7,166,062, which is incorporated herein by reference in its entirety and which is a Continuation-in-Part application of each of: i) U.S. patent application Ser. No. 09/349,608, filed Jul. 8, 1999, entitled "Systems and Methods for Providing an Improved Exercise Device with Motivational Programming," now U.S. Pat. No. 6,312,363, which is incorporated herein by reference in its entirety; and ii) U.S. patent application Ser. No. 09/496,560, filed Feb. 2, 2000, entitled "System and Method for Selective Adjustment of Exercise Apparatus," now U.S. Pat. No. 6,447,424, which is incorporated herein by reference in its entirety.

BACKGROUND OF THE INVENTION

1. The Field of the Invention

This invention relates to exercise equipment and, more specifically, to systems and methods for providing improved exercise devices in combination with other users and/or a live or stored trainer via a communications network.

2. The Relevant Technology

In an attempt to improve their health and physical conditioning, consumers are purchasing home exercise devices in record quantities. One common challenge with home exercise equipment is motivating the purchaser to use the device on a consistent and ongoing basis, while providing access to experienced trainers and individually developed exercise programs from the comfort of a user's own home. In addition, many exercise devices involve repetitive actions, which can quickly become tedious to a person exercising alone.

Health clubs, on the other hand, have organized various exercise classes and routines involving a group setting. In the proper setting, a group approach to exercise creates a synergy, whereby individual members of the class derive encouragement and motivation from other members of the group.

Furthermore, while individuals exercise at a health club they are taught the correct techniques for exercising, thereby reducing the possibility of being injured during an exercise program. In addition, group settings promote a healthy sense of competition among group members. Initially, such group fitness and exercise classes typically involved aerobics, traditionally performed without the use of any ancillary exercise equipment or devices. In recent years, however, the group work out approach has been extended to classes that utilize various exercise devices. Take, for example, the recent rise in popularity of "Spinning Classes," in which each participant operates his or her own stationery exercise cycle in a group setting, with a coach or instructor leading the group through a prescribed program or routine. Similarly, with recent advances in the design of treadmills, it is possible to have "Treadmill Classes" wherein an instructor not only leads the group, but the instructor is also able to control the operation of the treadmills of all of the class participants from a single control panel.

One of the primary disadvantages with group training, however, is that it is typically available only at health clubs and, therefore, is not as convenient as exercising in the privacy and comfort of one's own home. It would, therefore, be a definite advancement in the art of home exercise equipment to provide the desirable benefits of group exercise in a home setting. Some efforts have been made in the prior art to introduce a level of "interactivity" into exercise machines. For example, U.S. Pat. No. 5,489,249 discloses a video exercise control system in which a videocassette recorder (VCR) or similar device is coupled, via a hard wired connection, to an exercise machine, such as a treadmill. As an individual exercises on the treadmill, the VCR in synchronization with pre-recorded audio/video presentations controls the speed and incline of the treadmill. U.S. Pat. No. 5,645,509, entitled "Remote Exercise Control System" that is incorporated herein by reference, discloses a remote exercise control system in which an exercise machine, such as a treadmill, may remotely communicate via a communications module with an evaluation module located at a remote location. Signals indicative of the operating parameters of the treadmill are transmitted from the treadmill to the evaluation module, and control signals are transmitted from the remote evaluation module for controlling the operating parameters of the treadmill. U.S. Pat. No. 5,888,172 is representative of another, in which an exercise device is coupled, via hard wired connection, to a video game device, such that the operating parameters of the exercise device are used as inputs to the video game controller, which then produces a video display based on the inputs received. However, these approaches nevertheless fail to provide many desirable benefits of group exercise.

OBJECTS AND SUMMARY OF THE INVENTION

It is an object of the present invention is to improve home exercise equipment by providing home exercise devices that are capable of simulating a group or class workout environment and synchronizing operation of the exercise devices with exercise programming.

It is an object of the present invention to provide an exercise device that is capable of being controlled by packetized signals received from a trainer.

It is another object of the present invention to provide an exercise device that is capable of enabling a user to communicate with a distantly located trainer.

It is yet another object of the present invention to provide an exercise device that communicates with a communication system that enables real-time communication with a trainer or alternatively access to one or more stored exercise programs.

Yet another object of the present invention is to provide an exercise system that enables one or more users to receive real-time signals from one or more trainers via a network.

Still yet another object of the present invention is to provide an exercise system that enables a third party to control one or more user exercise devices and one or more trainer exercise devices in real-time.

Another object of the present invention is to provide an exercise system that enables a user to access various exercise equipment and information from a variety of locations.

Still a further object of the present invention is to provide a system where one device is capable of controlling one or more operating parameters of one or more other devices.

Yet another object of the present invention is to provide a system where the various modules of the system may be incorporated within a variety of devices.

Another object of the invention is to provide exercise devices that incorporate modules for receiving and decoding control signals embedded in multimedia (i.e., audio and/or video) programming for controlling various operating parameters of the exercise device in synchronization with the multimedia programming.

It is another object of the invention to provide exercise devices that are responsive to control signals that are encoded in programming external to the exercise device and containing audio and/or video and that can be transmitted and received by the exercise device.

Yet another object of the invention is to provide enhanced exercise devices, the operation of which can be controlled using interchangeable, multimedia programming containing control signals that is received via the Internet.

Yet another object of the invention is to provide an improved exercise machine that facilitates live, interactive communications between a treadmill user at home and a trainer or coach in a remote location, and which enables the trainer or coach to control the operating parameters of the user's treadmill on a live, real time basis.

The present invention is directed to devices, systems, methods, programs, computer products, computer readable media, and modules for controlling the operating parameters of one or more devices by one or more distantly located, or optionally closely located, devices through the use of packetized data technology. The present invention is particularly well suited to devices that utilize one or more motors and/or other electrically driven actuators that control one or more operating parameters of a device, such as an exercise device.

In one embodiment, the exercise device is configured to enable a user to interact with a trainer in real-time communication and includes an exercise mechanism having a movable element for movement in performance of exercise by a user. One example of such an exercise device is a treadmill, although a variety of different exercise devices may be employed. By employing real-time communication and interaction with a trainer, an exerciser can interact with the trainer, thereby achieving many of the benefits of a group exercise session in a home environment.

The exercise device of the present invention may have a variety of different forms. However, in one exemplary embodiment, an exercise device configured to enable a user to interact with a trainer in real-time communication, comprises: (i) an exercise mechanism comprising a movable element; (ii) one or more user interface devices, that communicates with the exercise mechanism and gathers a first real-time signal from the user; (iii) a communicating mechanism that communicates with the interface device and enables real-time transmission of the first signal to the trainer and receives a packetized second real-time signal. The second real-time signal may comprise a variety of signals, such as control signal and/or audio and visual signals. A processor, responsive to a control signal is configured to control the operating parameters of the exercise mechanism in real-time.

Thus, according the present invention, it is possible for a user to exercise on a device, such as a treadmill, while a trainer receives data regarding the operating parameters of the treadmill (and optionally of the user of the treadmill, e.g., heart rate), such as speed, inclination, etc. Upon receiving this data, the trainer can modify the operating parameters of the user's treadmill such that the user achieves an exercise program designed by the trainer. The trainer can also communicate in real-time with the user without interrupting any control signals that control the treadmill or other exercise device. The user can also communicate with the trainer without affecting any of these controls during such communication.

A variety of different options are available for achieving the desired real-time communication. According to one such option, a user can receive a broadcast from a live trainer (human being) or a stored trainer (e.g., a website, video, disk, or dynamic or interactive software program) upon activating the exercise device. As another option, the user can receive programming in response to a signal sent by the user. As yet another option, the trainer can analyze information about the exercise device (e.g., speed) and/or user (e.g., heart rate) and control the operating parameters of the exercise device and/or provide recommendations to the user through audio or video communication.

Thus, the present invention relates to an exercise device capable of achieving real-time communication with either: (i) a live or (ii) stored trainer. The present invention also relates to an exercise system comprising: (i) one or more user devices, such as an exercise device; (ii) one or more trainer devices, such as another similar exercise device connected to each other in a master/slave relationship. Optionally, in addition to the master and slave devices, a third party can control the master and/or slave. Examples of such third parties include an individual located at a master control console that controls the master and/or slave, such as in the setting of a spinning class.

The trainer and user may be linked in direct communication (e.g., master/slave) or indirect communication, such as by linking both the trainer and the user to a communication system that controls the operating parameters of an exercise device used by the user and/or trainer. For example, if both the trainer and the user devices are connected to a communication system, such as a website, the website may control the user device and/or the trainer device. Alternatively, the communication system may track changes of the operating parameters of the trainer device and modify the operating parameters of the user device based upon the changing parameters of the trainer device.

Optionally, a stored trainer (e.g., a website) controls a user device without requiring the services of a live trainer. The present invention also enables first and second users to compete against each other by connecting their corresponding exercise devices to a communication system, such as a website.

The present invention also relates to programming, computer products and computer readable medium including instructions designed to facilitate the above-described systems, inventions and exercises and other systems, devices, and exercises. As will be discussed in greater detail, the present invention is not limited to any particular device, although treadmills and other exercises are employed as examples to illustrate the operation and function of the present invention.

These advantages in addition to other objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above recited and other advantages and features of the invention are obtained, a more particular description of the invention briefly described above will be rendered by reference to specific embodiments thereof that are illustrated in the appended drawings. Understanding that these drawing depict only typical embodiments of the invention and are not therefore to be considered to be limiting of its scope, the invention will be described and explained with additional specificity and detail through the use of the accompanying drawings in which:

FIGS. 17A-D are flow diagrams representative of the processes a user performs using the competition module of FIG. 12;

DETAILED DESCRIPTION OF THE INVENTION

The present invention is directed to devices that include one or more motors or other electrically driven actuators used to control one or more operating parameters of the device. While the invention will be described in the context of a motorized treadmill, it should be understood that the invention is not limited to any particular type of exercise device. To the contrary, the present invention can be readily adapted to any motorized device or any other device that utilizes motors, solenoids, or any other electrically driven actuators to control any operating parameter of the device, such as speed, resistance, incline, time, temperature, or other similar operating parameters. The term "device" or "devices" shall refer broadly to any type of apparatus that includes one or more stepper motors, solenoids, or other electrically driven actuators or controllers. Additionally, the term "exercise devices" shall refer broadly to any type of device that takes the form of an exercise machine, including, but not limited to, treadmills, exercise cycles, Nordic style ski exercise devices, rowers, steppers, hikers, climbers, and elliptical or striding exercise devices.

Figure 1:
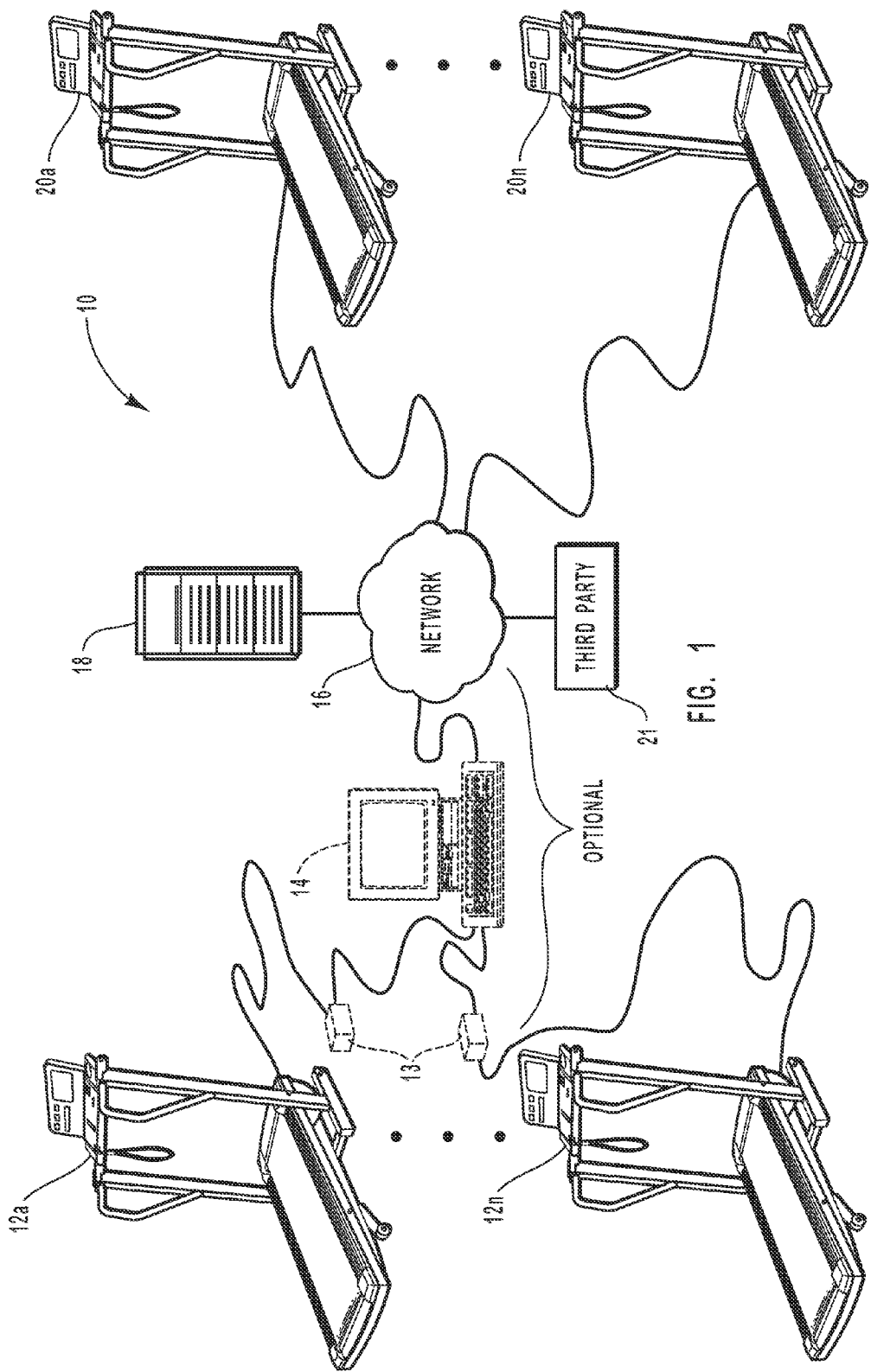
FIG. 1 is an exercise system according to the teaching of the present invention.

Depicted in FIG. 1 is a representation of one illustrative system, designated by reference numeral 10, that may incorporate the novel features of the present invention, including various novel devices, hardware and software modules, and the like that may be remotely accessed and controlled in a real-time manner. As shown, one or more exercise mechanisms, such as a treadmill 12a-12n is in communication with one or more trainers at treadmill 20a-20n via a translator device 13 and a personal computer 14. The translator device 13 and personal computer 14 communicate with a network 16 that is a communication network that enables various hardware and software modules and devices to communicate one with another. Network 16, therefore, may be a local area network (LAN), wide area network (WAN), wireless network, packetized network, real-time network, and the like. Network 16 facilitates communication of treadmill 12 with a live trainer on treadmill 20 and/or communication system 18 (e.g. a website). Communication system 18 assists communication between a user on treadmill 12 and either a live trainer on treadmill 20, or some other third party 21, as will be described in more detail hereinafter. Optionally, communication system 18 acts as a stored trainer or connects to a stored trainer.

The following discussion will be directed to only a single treadmill 12 and a single treadmill 20, however, it may be appreciated that a similar discussion may be had for multiple treadmills 12a-12n, 20a-20n. In addition, although only one of each element of system 10 is depicted, it may be appreciated by one skilled in the art that system 10 may have a mixture of both single and multiple elements, for example, at least one treadmill 12, 20, translator device 13, personal computer 14, network 16, and communication system 18. Alternatively, one or more of the elements of system 10 may be eliminated or the functionality thereof incorporated within the structure and function of one or more of the other elements of system 10.

Similarly, although each of the elements of system 10 are shown separated one from another, it may be appreciated by one skilled in the art that the hardware and/or software elements of the present invention may be incorporated within two or more elements. For example, translator device 13 and personal computer 14 may be incorporated within treadmill 12. Similarly, the hardware and/or software elements of the communication system 18 may be incorporated within treadmill 20.

As defined herein, the term "trainer" or "third party" 21 may include: (i) a live human being; or (ii) a stored trainer, such as a website, computer, optical media (e.g., compact disk or digital video disk), visual media, or magnetic media (e.g., videotape, readable disk), an electronic monitoring system, dynamic computer readable instructions, interactive and/or dynamic software programs, computer readable instructions, and other media and hardware and/or software modules and components, whether or not the trainer is located at treadmill 20 or at some other location. In one embodiment, the third party is another trainer.

Generally, system 10 enables exercise programming with control signals to be transmitted from a trainer at treadmill 20, or alternatively from communication system 18, to a user at treadmill 12. As disclosed in U.S. patent Ser. No. 09/349,608 entitled "Systems and Methods for Providing an Improved Exercise Device with Motivational Programming," which is incorporated herein by reference, the programming may include motivational content and/or one or more control signals that may be used to control the operating parameters of treadmill 12 in real-time in an uninterrupted manner. The control signals may be synchronized with the motivational content and designed to control one or more operating parameters of the exercise device, such as the speed, incline, difficulty of exercise program, time, distance, and the like of an exercise program performed on treadmill 12.

As used herein, the term "motivational content" is used to broadly refer to any audio material, including dialog, narration, sound effects, and/or music, either alone or in combination with video material. In one embodiment of the present invention, the motivational content is stored in communication system 18 and includes an audio/video presentation of a personal trainer and others engaged in a series of exercises of varying difficulty. In another embodiment of the present invention, the motivational content is a live-on-live, real-time exercise program presented by one or more personal trainers that is either specific to one particular user or alternatively broadcast or optionally "webcast" to any user that may access communication system 18. In still yet another embodiment, the programming includes an exercise profile of the intensity of various exercise criteria, such as, but not limited to, speed, incline, or resistance of the exercise device, that is displayed continually or periodically to the user during the performance of the programming. In still yet another embodiment of the present invention, the user controls the period of when the exercise profile appears. One skilled in the art may appreciate that various other configurations of programming are applicable.

Generally, the second real-time signal may include both the motivational content and the control signals, whether or not such control signals are synchronized with the motivational content. Alternatively, the second real-time signal may include only the motivational content, other signals representative of measurable parameters of the exercise device (e.g. speed, inclination, resistance, etc) and/or a user of the exercise device (e.g. heart rate, blood pressure, etc), and the like. For example, treadmill 12 may transmit one or more signals to communication system 18. The signal may include parameters such as the status of the exercise device, e.g., active status (i.e., on), deactivated status (i.e., off), standby status (i.e., waiting), and the like, and/or parameters such as speed, inclination, resistance. Additionally, the signal may include parameters regarding the user, such as heart rate, blood pressure, and the like. Alternatively, treadmill 12 may receive programming "broadcast" by communication system 18 and/or a trainer at treadmill 20, such that any treadmill with the capabilities to receive the programming may access such, without the need to transmit one or more signals.

As mentioned above, the control signals control the operating parameters of treadmill 12, such as speed, inclination, resistance, and the like. Such control may be achieved by a trainer at treadmill 20, a combination of a trainer at treadmill 20 and communication system 18, or a third party 21 interacting with treadmill 20 and/or communication system 18. Generally, the present invention allows control of a device, such as an exercise device, without the need to interrupt the other portions of the programming, such as the real-time audio and/or video.

FIGS. 2 through 5 generally depict a typical motorized, reorienting treadmill 12. Although the discussion herein will be directed to treadmill 12, it may be appreciated by one skilled in the art that treadmill 20 may include all or a portion of the elements, modules, and means discussed herein Treadmill 12, in one embodiment, includes a control panel 22 supported on a generally upright support structure 24 and a tread base 26. Upright support structure 24, in this illustrative embodiment, includes two side members 28, 30 coupled together by way of one or more cross members 32. Side members 28, 30 and cross members 32 may have various configurations and may be fabricated from various materials so long as they are capable of supporting control panel 22 and tread base 26. For example, the elements of upright support structure 24 may be fabricated from, but not limited to metals, plastics, composites, combinations thereof, and the like. Additionally, one skilled in the art may appreciate that various other exercise devices may have different upright support structures, side members, and cross members, or be devoid of one or more of such structures and members.

Figure 4:
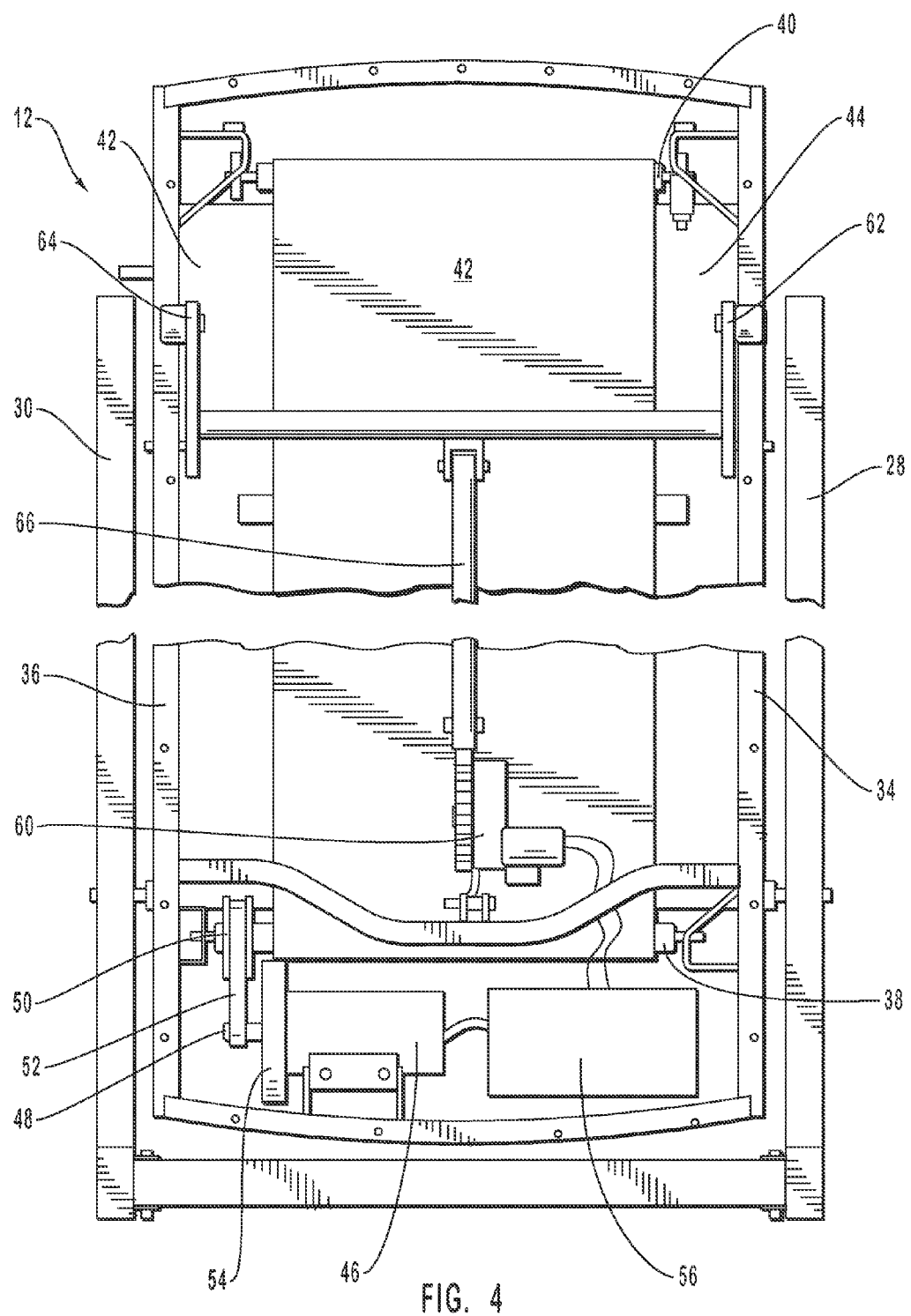
FIG. 4 is a partial plan view of portions of the reorienting treadmill illustrated in FIGS. 2 and 3 with the treadmill oriented in the second or storage position and with the bottom cover removed, revealing some of the internal components of the treadmill.

The tread base 26 typically includes a pair of side rails 34, 36 each having a front portion proximal to and a rear portion distal from upright support structure 24 when tread base 26 is in a downward exercisable position. As shown in FIG. 4, a front pulley 38 and a rear pulley 40 are disposed between and supported by side rails 34, 36, while a continuous belt 42 extends between and around front and rear pulleys 38 and 40, respectively. Pulleys 38, 40 and belt 42 may have various configurations and be fabricated from various materials, as known by one skilled in the art and commonly known within the exercise industry.

A deck 44, commonly fabricated from wood, typically supports the upper run of belt 42 and supports an exercising individual resting upon belt 42. Although deck 44 is preferably of a cellulose material such as wood, various other types of material may be used so long as deck 44 is capable of supporting belt 42 and a user exercising thereupon.

As best seen in FIG. 4, in one embodiment, front pulley 38 is mechanically coupled to an electric tread drive motor 46 by way of pulleys 48 and 50 and a drive belt 52. In this illustrative embodiment, motor 46 further incorporates an inertial flywheel 54 that controls fluctuations in the rotational motion of a shaft of motor 46 during operation of treadmill 12. Motor 46 is optionally electrically coupled to a treadmill controller 56 that controls the operation of motor 46, and thus the speed of belt 42, in response to various user inputs or other control signals. As shown, treadmill controller 56 is incorporated within tread base 26; however, it may be appreciated by one skilled in the art that treadmill controller 56 may be incorporated within control panel 22 or alternatively within personal computer 14.

Figure 5:
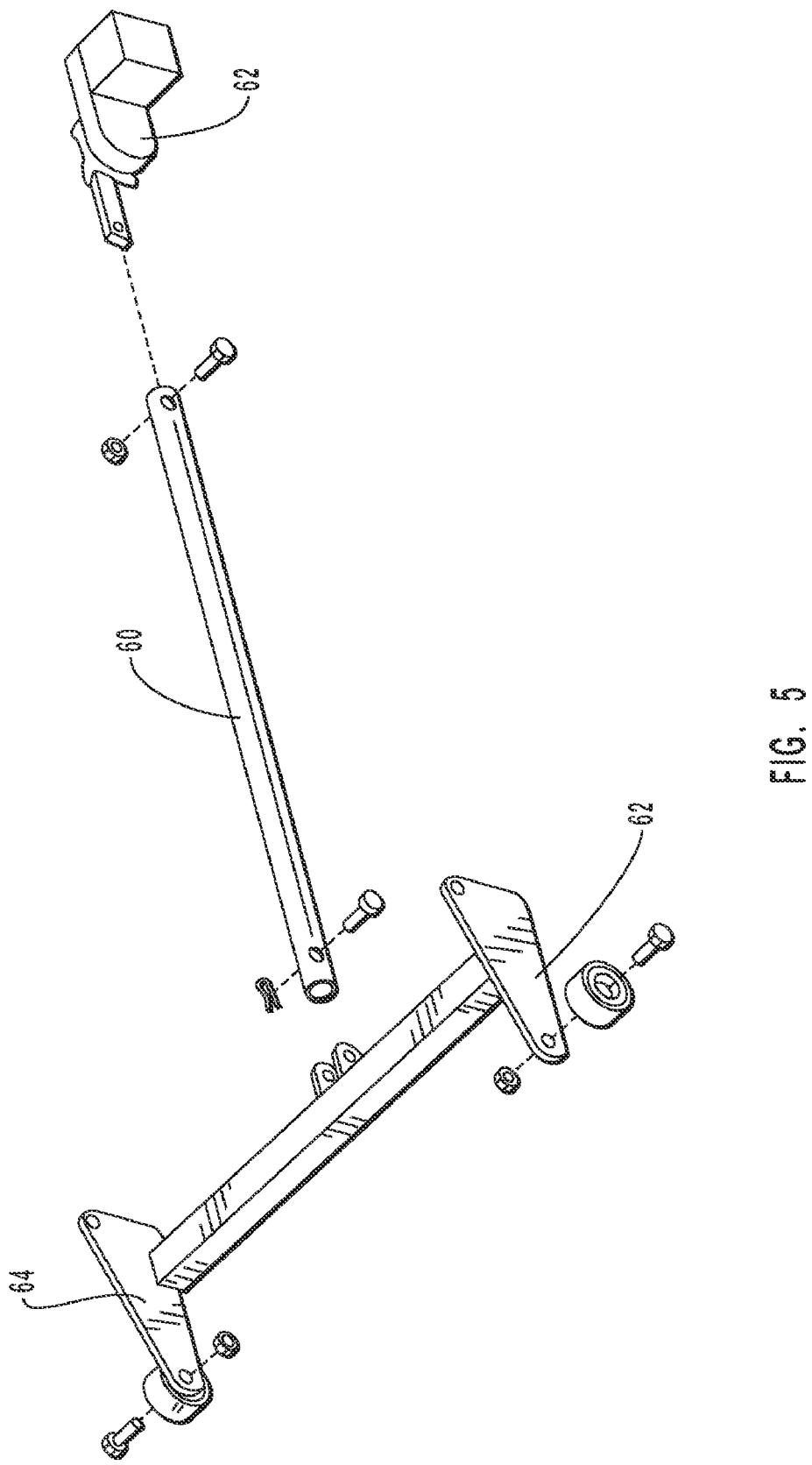
FIG. 5 is a partial exploded perspective view of the incline mechanism incorporated into the treadmill illustrated in FIGS. 2 through 4.

In addition to the ability to control and vary the speed of belt 42, treadmill 12 also permits the degree of incline of tread base 26 relative to the floor, or other surface upon which tread base 26 rests, to be varied. Typically, this is accomplished through the use of an incline drive motor 60 that rises or lowers one end of tread base 26 relative to the other end. In the embodiment illustrated in FIGS. 2 through 5, tread base 26 includes a pair of rear feet 62 and 64 that are rotatably attached to the rear of portion of side rails 34, 36. As best seen in FIGS. 4 and 5, feet 62 and 64 are mechanically coupled through a shaft 66 to incline drive motor 60, which causes feet 62 and 64 to pivot about their points of pivotal attachment to side rails 34, 36, thereby selectively raising or lowering the rear end of tread base 26 relative to the front end thereof. Motor 60 is also optionally electrically coupled to, and controlled by the treadmill controller 56.

Figure 2:
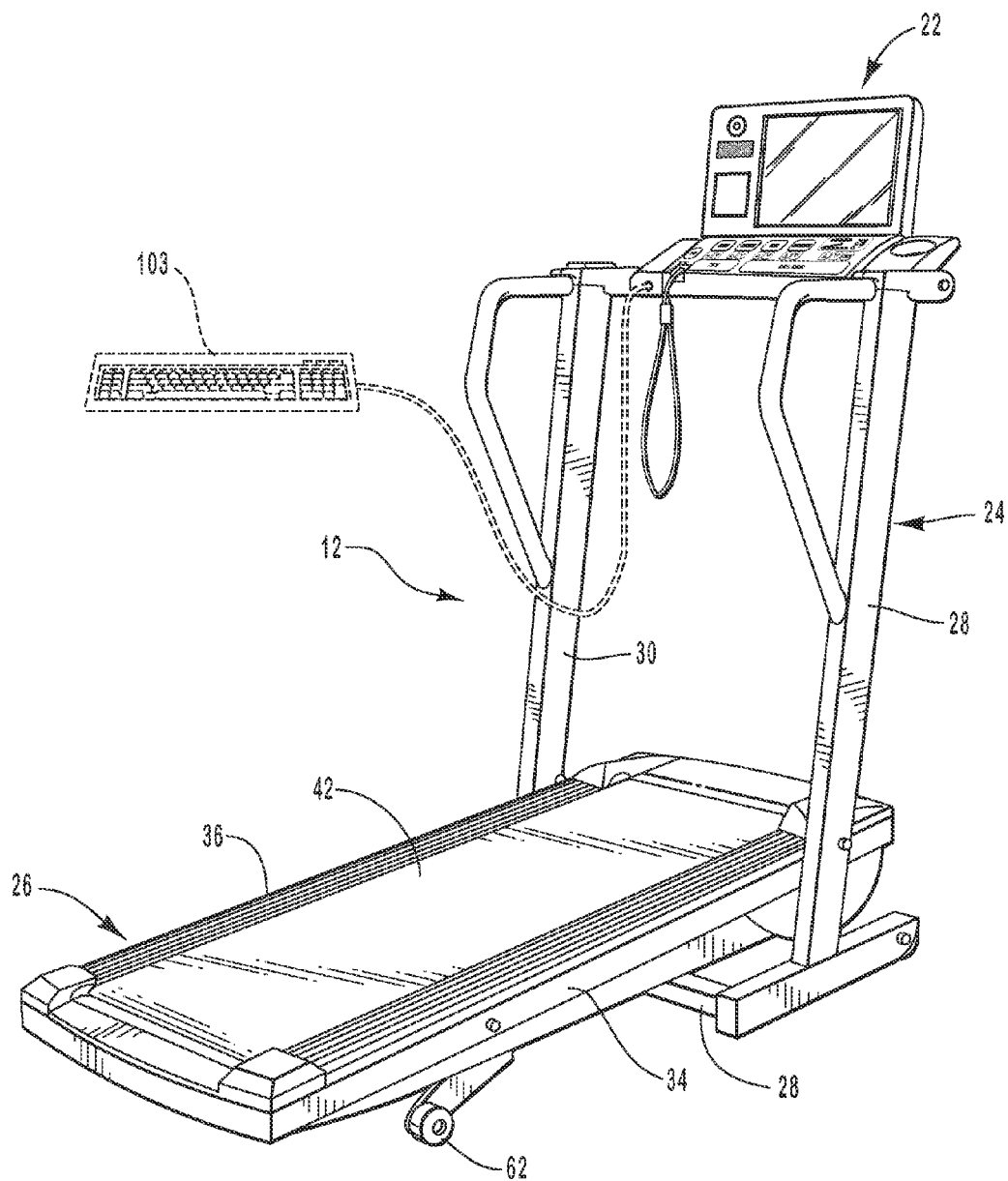
FIG. 2 is a perspective illustration of a reorienting treadmill with the tread base positioned in a first position for a user to perform exercises to be used in the exercise system of FIG. 1.
Figure 3:
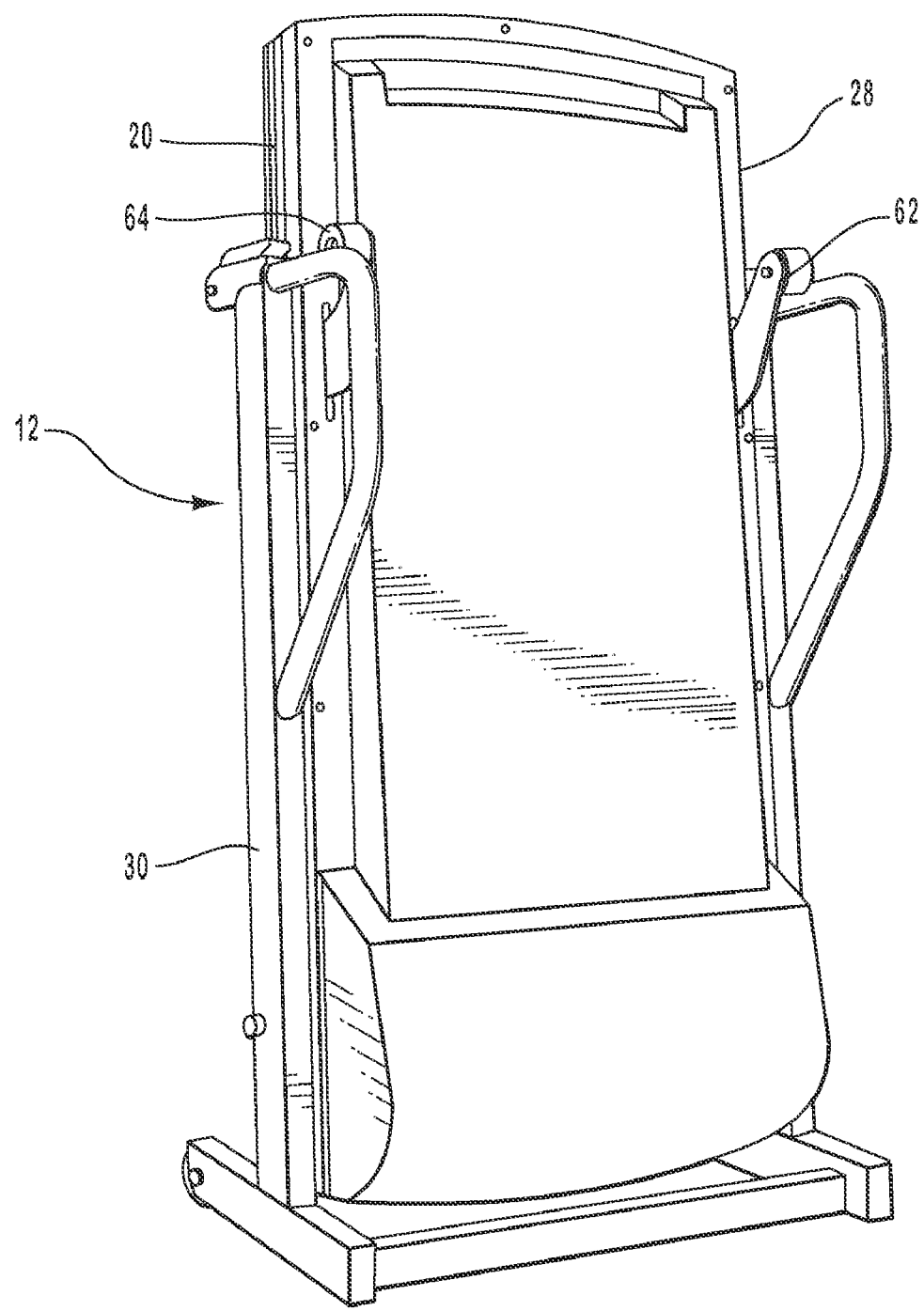
FIG. 3 is a perspective illustration of a reorienting treadmill of FIG. 2 with the tread base positioned in a second or storage position.
Figure 6:
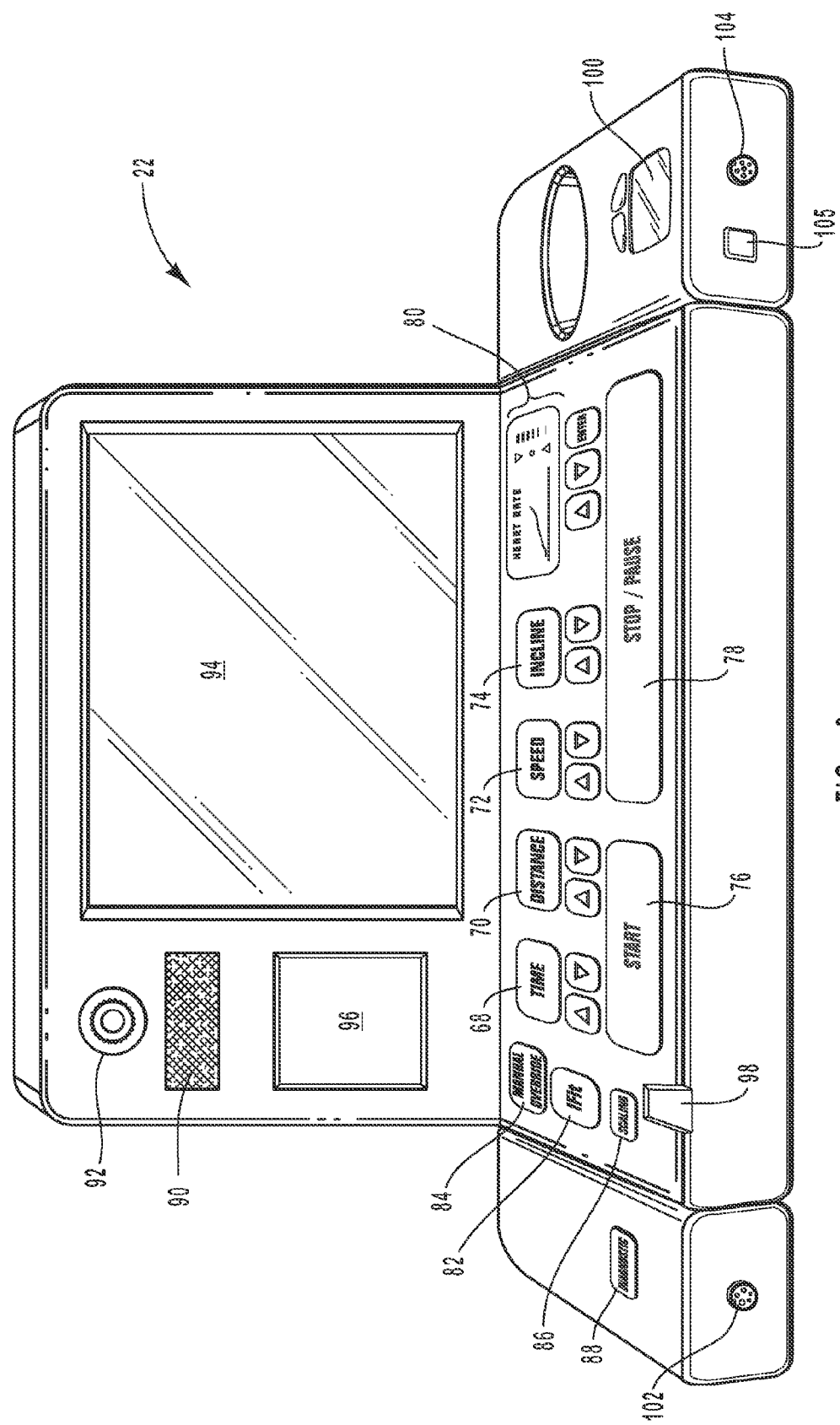
FIG. 6 is a perspective illustration of a control panel of the reorienting treadmill of FIG. 2.

As shown in FIG. 2, treadmill 12 (and optionally treadmill 20) includes control panel 22 attached to side members 28, 30 of upright support structure 24. Control panel 22, in one embodiment, as shown in FIG. 6, includes one or more interface devices. Such interface devices may be either input devices or output devices. Input devices enable a user to input and vary the operating parameters of treadmill 12. As examples of such input devices, control panel 22 includes many typical controllers for use on an exercise device, such as a treadmill. A number of illustrative input devices include but are not limited to speed controls 68, incline controls 70, time controls 72, distance controls 74, a start button 76, a stop or pause button 78, and heart rate controls 80. In addition to these input devices, such as one or more controllers, control panel 22 further optionally includes an iFit.com button 82, a manual override button 84, and a scaling control 86, each of which are also examples of input devices. It may be appreciated that each of the above-recited controllers or buttons may be embodied in a variety of different manners to perform their commonly utilized function. In addition, each controller, button, and the like may take the form of one or more switches, rheostats, potentiometers, touch sensitive controls, voice activated controllers, and the like. The input devices described herein are examples of structures capable of performing the function of interface means for gathering a first signal (such as a real time signal) from the user. One skilled in the art may identify various other configurations of interface means that are capable of performing the desired function. Additionally, it may be appreciated that treadmill 20 may also include such interface means.

As shown in FIG. 6, iFit.com button 82, in one embodiment, acts as both a selector and an indicator of connectivity of treadmill 12 to communication system 18, and optionally treadmill 20, whether such connectivity is via translator device 13, computer 14, or directly from treadmill 12. The iFit.com button 82 optionally includes an indicator light (not shown) that demonstrates when a connection has been established between treadmill 12 and communication system 18, such as when iFit.com button 82 is depressed. Alternatively, a light emitting diode (LED) positioned in close proximity to iFit.com button 82 may be activated when iFit.com button 82 is activated.

The connection achieved by activating iFit.com button 82 may be via a variety of communication line connections. For example, as shown, control panel 22 includes a wireless port 105 that enables treadmill 12 to wirelessly communicate with network 16 (FIG. 1), either directly or via computer 14 and/or translator device 13. Alternatively, wireless port 105 may be located on tread base 26. Various other types of port or interface may be included within treadmill 12 to enable communication via one or more communication line connections. For example, treadmill 12 may include one or more ports and interfaces to enable communication line connection through existing broadcast technology, including television broadcast over the airwaves, cable or cable modems, satellite, telephone lines, whether analog or digitally based, the internet, DSL, G-Lite, wireless technology, infra-red (IR) technology, other high-speed data connections, or any other suitable transmission technology or medium. Optionally, a communication port on a user treadmill may enable communication directly with another treadmill (such as in a master/slave scenario), whether or not such communication utilizes a network.

In one embodiment, by activating iFit.com button 82, a user of treadmill 12, or other exercise device, connects to communication system 18, such as a website. Such connection may be via an independently located computer, such as computer 14, through translator device 13 or directly through a local area network (LAN) or wide area network (WAN) by way of the described communication line connections for example, or other connections known to one skilled in the art.

More specifically, by activating the iFit.com button 82 a signal is transmitted to communication system 18 to create a connection therebetween. In this manner, treadmill 12 may receive signals representative of exercise programming from communication system 18. Additionally, the connection with communication system 18 enables the user to obtain the services of a stored trainer or a personal trainer to perform programming, ask questions, download or access programming materials, surf the web, gather and send electronic mail messages ("e-mail"), listen to audio programming, view video programming, review and update user information and statistics, load user statistics, purchase exercise programming, equipment, and materials, update exercise device software and operating parameters, research exercise materials, and the like.

Furthermore, activation of the connection with communication system 18 enables treadmill 12, or other exercise device, to have the potential of being controlled during an exercise program by a third party, whether that third party is another personal trainer using another treadmill 20, a stored communication system 18, or some other individual, hardware, or software modules or components. For example, a third party individual or a stored third party trainer may operate a console controlling the operation of one or more exercise devices in a group class setting, including devices operated by a live or stored trainer and by trainee users. This may be useful in a spinning class or other class in which a trainer trains trainee users. In one embodiment, as the third party controls the operation of the exercise devices, the trainer can communicate motivational messages to the trainee users.

Similarly, activation of the connection with network 16 and/or communication system 18 enables one or more users to interact one with another, and optionally compete one against another as shall be described in detail hereinafter. For example, a first user on treadmill 12a may receive information regarding the workout performed by a second user on treadmill 12n via network 16 and/or communication system 18, then compete against the second user and vice versa. This competition may be live on live or time adjusted, e.g., a workout recorded previously by the second user which the first user competes against. Greater information about communication system 18, with its associated modules and components will be discussed in detail hereinafter.

As mentioned above, control panel 22 may include manual override button 84. Manual override button 84 enables a user to override an action initiated by (i) a live trainer or (ii) a stored trainer, such as communication system 18, stored programming that is located within the memory of computer 14, or alternatively in memory stored in treadmill 12. For example, if the exercise program accessed through communication system 18 is too difficult for the user, the user may activate manual override button 84 thereby interrupting the program delivered to treadmill 12 by communication system 18. Furthermore, in the event that the exercise program is too easy, the user may increase the difficulty level of the exercise device. Consequently, manual override button 84 provides the user with a safety switch during operation of treadmill 12. In an alternate configuration of treadmill 12, the functionality of manual override button 84 is activated upon manual activation of one of the other input devices, such as but not limited to, incline controls 74, speed controls 76, stop/pause button 78, and the like.

Similar to the operation of manual override button 84, scaling control 86 enables a user to vary the operating parameters of treadmill 12 during an exercise program initiated externally to treadmill 12. A user may activate scaling control 86 and vary the intensity of an exercise program. The scaling control 86, therefore, enables a user to select a value representative of the proportional change to be made to the control signal received by the communicating mechanism of treadmill 12 from communication system 18. For example, if an exercise program requires a maximum speed of 6 miles per hour (mph) with a maximum incline of 15 degrees for a period of 30 minutes, an individual may activate scaling control 86 to require only 66% intensity of the exercise program; stated otherwise, reduce the intensity by one third. Therefore, the exercise program is varied to a maximum speed of 4 mph, with a maximum incline of 10 degrees, for a period of 20 minutes. Optionally, scaling control 86 may enable the user to set maximum values for each operating parameter of treadmill 12. In another configuration, scaling control 86 may enable the user to scale only one operating parameter of treadmill 12 while leaving other parameters unchanged. Hence, the user may vary the exercise program to their particular abilities, while obtaining the beneficial effects of exercising.

As another example of an input device of the present invention, control panel 22 may include a diagnostic control 88. Upon activation of diagnostic control 88, whether be depressing a button or by some other manner known to one skilled in the art, treadmill 12 communicates with communication system 18 to check the operating status of the exercise device. Communication system 18, thereby sends signals to the internal hardware and software modules of treadmill 12 to verify that the modules are operating within the desired specifications or to determine whether treadmill 12 may include software for which an update is available. In one embodiment, in the event that one or more of the hardware and/or software modules are damaged or not performing as required, communication system 18 may download one or more software updates from communication system 18 if possible. Alternatively, communication system 18 may inform the user that an error has occurred and advise that the user obtain maintenance of the hardware components of treadmill 12.

As additional examples of input devices, according to another aspect of the present invention, control panel 22 may include an audio input device 90 and a video input device 92. Audio and video input devices 90, 92 enable a user to perform communication, such as real-time communication, with other users of exercise devices, via communication system 18 (FIG. 1). The audio and video input devices 90, 92 also enable the user to hear and/or watch (i) a live trainer or (ii) a stored trainer, such as recorded programs, educational programming, entertainment programming, and the like. The diagnostic control 88, audio input device 90 and video input device 92, therefore, are structures capable of performing the function of interface means, communicating with the exercise mechanism, for gathering a first signal from the user. Various other configurations of such interface means are known to one skilled in the art in view of the teachings contained herein.

In one embodiment, audio input device 90 may take the form of a microphone, while video input device 92 may take the form of a video camera. Audio input device 90 and video input device 92 may alternatively take various other configurations as known by one skilled in the art. For example, audio input device 90 may be a microphone detachably connected to control panel 22 or another part of treadmill 12. In another configuration, audio input device 90 may be located distant from treadmill 12, while being capable of gathering the audio inputs from the user. In still another configuration, audio input device 90 may be eliminated from treadmill 12, while treadmill 12 includes an audio jack, such as an RCA-type audio jack, RJ-type jacks, digital audio jack, and the like. In still another configuration, audio input device 90 may be a radio frequency (RF), infra red (IR), or wireless type microphone. Similarly, video input device 92 may have the configuration of a digital video camera integrally formed within control panel 22. Alternatively, video input device 92 may be detachably connected to control panel 22 or another part of treadmill 12, such as wireless digital cameras. Still in another configuration, video input device 92 may be located distant from treadmill 12, while being capable of gathering the requisite video signals to be transmitted to communication system 18 (FIG. 1).

In addition to the above-described audio and video input devices 90, 92 respectively, control panel 22 may include a variety of other input devices. For example, control panel 22 may include an integrally formed mouse 100. Additionally, control panel 22 may include a keyboard jack 102 for an external keyboard 103, a controller port 104 for receiving one of a variety of game controller, an integrally formed mouse 100, a touch-sensitive video display, and various other ports, jacks, or the like to receive various other external components. Each input device is adapted to allow a user operating treadmill 12 to more fully operate one or more operating parameters of treadmill 12. Furthermore, the input devices enable the user to access communication system 18 and/or obtain educational, entertainment, or other information via network 16, whether such information is from communication system 18 or from one of a variety of other hardware and/or software modules that are accessible via network 16. For example, the input devices may allow the user to surf the Internet to find educational materials or entertainment. These additional input devices are further examples of structures capable of performing the function of interface means, communicating with the exercise mechanism, for gathering a first signal from the user.

Control panel 22, in one embodiment includes one or more output devices that provide a visual and optionally an audio indication of the operational status of treadmill 12 to the user. As with the input devices, the output devices may have various configurations and perform numerous functions. Generally, the output devices described herein are each structures capable of performing the function of means for reproducing a signal. The output devices and hence the means for reproducing a signal may have various configurations as known to one skilled in the art in view of the teaching contained herein. In one embodiment, one video output device 94 may be a video display. Generally, video output device 94 presents the user of treadmill 12 with information and data transmitted from communication system 18, whether such data is live transmission from treadmill 20, or alternatively stored programming accessible by communication system 18. Additionally, video output device 94 may optionally show information and data from: (1) various other sources selected by the user, third parties, or system 10; (2) statistical information representative of the operational parameters of treadmill 12, such as the speed, incline, duration of user's workout, etc.; (3) electronic mail messages (e-mail), and the like. Video output device 94, in one embodiment is a liquid crystal display (LCD) or cathode ray tube (CRT) display.

One skilled in the art may appreciate that various other devices may be used to perform the functions of video output device 94. For example, video output device 94 maybe an electroluminescent display (ELD), a gas-plasma display, a thin film transistor (TFT) display, a virtual reality (VR) display, and the like. In another embodiment of the present invention, control panel 22 includes multiple video output devices 94. In still another embodiment, video output device 94 is adapted to permit split screen or layered images that are associated with picture-in-picture viewing of various images and information. For example, video output device 94 may allow a user to watch various types of entertainment and/or surf the Internet, while receiving images representative of the exercise profile that they are following whether continuously, periodically, upon activation of a user control, or the like.

As shown in FIG. 6, in one embodiment of the present invention, control panel 22 includes an audio output device 96, such as a speaker. Audio output device 96 performs a similar function to that of video output device 94, in that audio output device 96 provides the user with audible signals representative of the operational parameters of treadmill 12. Additionally, audio output device 96 may deliver audio, visual, or control signals to the user from communication system 18 and treadmill 20. Such signals may be audible and/or inaudible signals transmitted from the trainer on treadmill 20. Various speakers are applicable and may operate as audio output device 96, for example, hardwired and wireless speakers, such as computer speakers, audio system speakers, and the like. Control panel 22 may optionally include one or more amplifiers in cooperation with audio output device 96. Furthermore, audio output device 96 may be circumvented through use of one of a variety of audio jacks that enable a user to listen to the audio output through headphones or similar audio transmitting device.

In addition to the output devices described above, the present invention may include various other output devices to provide information and data to the user of treadmill 12. In one embodiment of treadmill 12, control panel 22 includes one or more operating parameter displays. The one or more operating parameter displays give a visual display of some of the more important exercise device operating parameters, such as, but not limited to, speed, incline, distance traveled, calories used, elevation climbed, wheel resistance, and the like. The one or more operating parameter displays may use a numerical display, a graphical display, combinations thereof, or such other displays known to one skilled in that art. For example, the operating parameter display may be incorporated within video output device 94.

As shown in FIG. 1, communicating with treadmill 12 via personal computer 14 is communication system 18 and treadmill 20. Those skilled in the art will appreciate that computer 14 may take various configurations, including personal computers, hand-held devices, multi-processor systems, microprocessor-based or programmable consumer electronics, telephones, network PCs, minicomputers, mainframe computers, and the like. Additionally, computer 14 may be part of a distributed computer environment where tasks are performed by local and remote processing devices that are linked (either by hardwired links, wireless links, or by a combination of hardwired or wireless links) through a communications network, such as network 16. Furthermore, as suggested earlier, treadmill 12 may optionally incorporate the functionality of personal computer 14 therein or include one or more modules or components of computer 14 while not incorporating all the modules and components of computer 14.

The following discussion will focus on certain examples of alternate structures that may be used as computer 14; however it is understood that a similar discussion may be made for the hardware and/or software modules and components associated with communication system 18, treadmill 20, and/or a third party 21. Furthermore, it may be appreciated that treadmill 12, treadmill 20, communication system 18 and third party 21 may incorporate portions of computer 14 as described herein and appreciated by one skilled in the art in light of the teaching contained herein. Similarly, one skilled in the art will recognize that treadmill 12 and/or communication system 18 may includes some or all of the modules and components of computer 14.

Generally, computer 14 is configured to receive data from various portions of treadmill 12 and deliver manipulated data to the hardware and/or software modules or components associated with communication system 18 and/or treadmill 20 or other treadmills 12a-n. In addition, computer 14 communicates with communication system 18 and retrieves audio, video, and control signals therefrom and provides these signals to treadmill 12, whether or not the signals are initiated solely by communication system 18, treadmill 20, a third party 21, or another treadmill 12a-12n. Computer 14 may, therefore, use various types of interfaces to communicate with treadmill 12 and network 16. For example, the interface may be a wireless interface thereby utilizing IR, RF, satellite, blue tooth transmission and associated protocols. Alternatively, the interface may be a modem, cable modem, ADSL connection, ISDN, Ethernet, or similar other connections, voice activated, and the like.

Following herein after is a general discussion of possible modules and components of computer 14. The following discussion is merely illustrative of modules and components that may form computer 14. It is appreciated that some of the referenced modules may be eliminated while other modules and components may be included within computer 14, as known by those skilled in the art.

Figure 7:
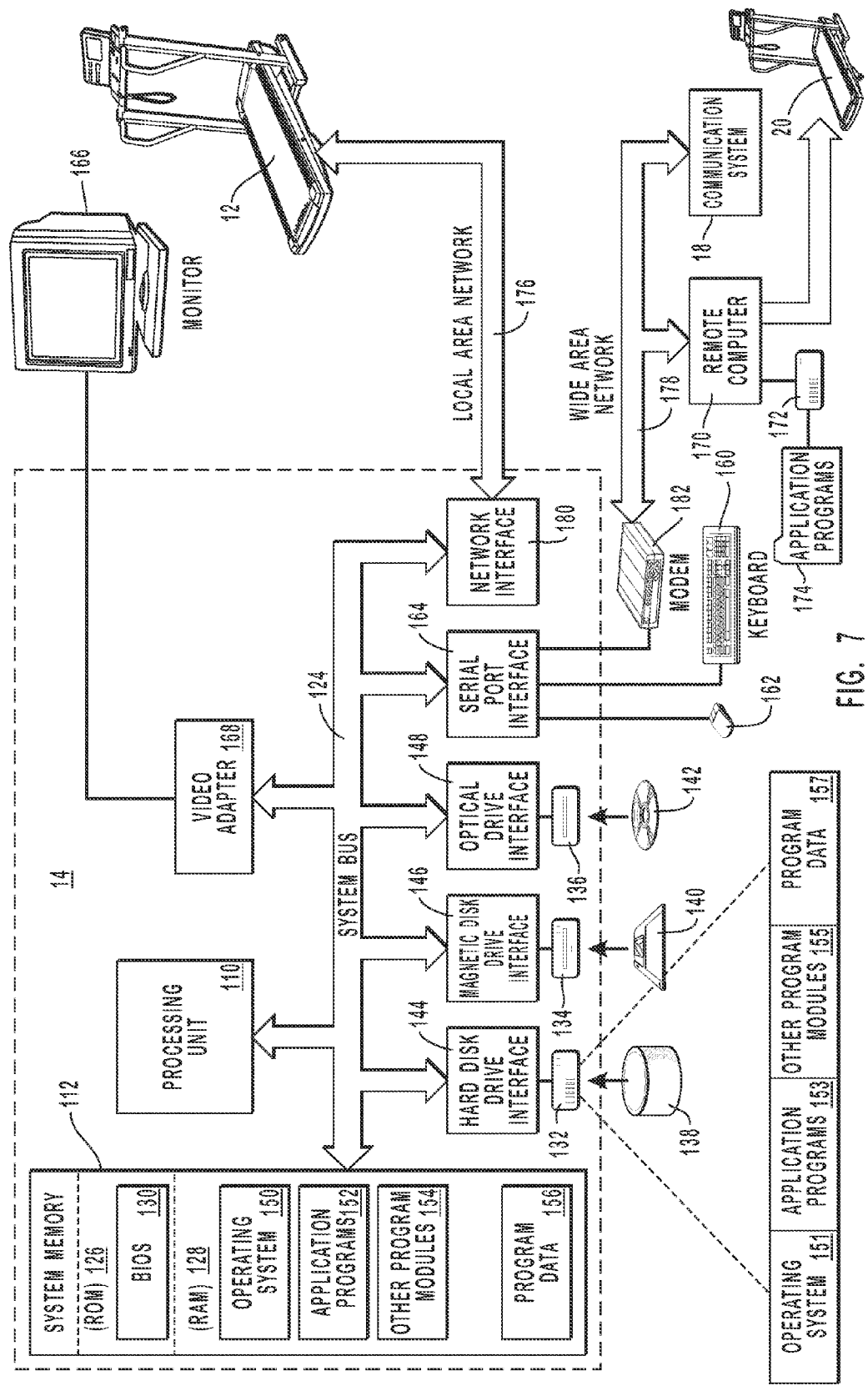
FIG. 7 illustrates an exemplary computer and associated system that provides a suitable operating environment for the exercise system of FIG. 1.

With reference now to FIG. 7, in one embodiment of the present invention computer 14 is a general-purpose-computing device, including a processing unit 110, a computer memory 112, and a computer bus 124 that couples various computer components including the computer memory 112 to the processing unit 110. The computer bus 124 may be any of several types of bus structures including a memory bus or memory controller, a peripheral bus, and a local bus using any of a variety of bus architectures. Additionally, when treadmill 12 includes computer 14 and/or translator 13 computer bus 124 may be an $I^2C$ bus, a SPI bus, a microwire bus, a microbus, and the like. Also, computer bus 124 may use the CAN protocol, CSAFE 1 protocol, or some other protocol known to one skilled in the art to allow communication between treadmill 12 and communication system 18 and/or treadmill 20 either directly or through network 16.

The computer memory, in this particular embodiment, includes read only memory (ROM) 126 and random access memory (RAM) 128. A basic input/output system (BIOS) 130, containing the basic routines that help transfer information between elements within computer 14, such as during start-up, may be stored in ROM 126.

The computer 14 may also include a magnetic hard disk drive 132 for reading from and writing to a magnetic hard disk 138, a magnetic disk drive 134 for reading from or writing to a removable magnetic disk 140, and an optical disk drive 136 for reading from or writing to removable optical disk 142 such as a CD-ROM or other optical media. The magnetic hard disk drive 132, magnetic disk drive 134, and optical disk drive 136 are connected to computer bus 124 by a hard disk drive interface 144, a magnetic disk drive-interface 146, and an optical drive interface 148, respectively. The drives and their associated computer-readable media provide nonvolatile storage of computer-executable instructions, data structures, program modules, and other data for computer 14 as will be discussed in detail hereinafter. Although the exemplary environment described herein may employ a magnetic hard disk 138, a removable magnetic disk 140, and a removable optical disk 142, other types of computer readable media for storing data can be used, including magnetic cassettes, flash memory cards, digital video disks, Bernoulli cartridges, RAMs, ROMs, and the like.

Computer 14, in one embodiment, further includes program code means comprising one or more program modules that may be stored on hard disk 138, magnetic disk 140, optical disk 142, ROM 126 or RAM 128, including an operating system 150, one or more application programs 152, other program modules 154, and program data 156. A user may enter commands and information into computer 14, in one embodiment, through a keyboard 160, pointing device 162, or other input devices (not shown), such as, but not limited to microphones, joy sticks, game pads, satellite dishes, scanners, video cameras, potentiometers, buttons, switches, rheostats, or the like, whether such devices are incorporated within treadmill 12 or in communication with translator device 13 and/or computer 14. These and other input devices are often connected to processing unit 110 through a serial port interface 164 coupled to computer bus 124. Alternatively, the input devices may be connected by other interfaces, such as a parallel port, a game port, or a universal serial bus (USB), and the like. A monitor 166 or another video display device, such as those described herein is optionally connected to computer bus 124 via an interface, such as video adapter 168. In addition to the monitor, personal computer 14 may include other peripheral output devices (not shown), such as one or more speakers, and printers for obtaining recent statistical information regarding the user's workouts.

The computer 14, as depicted in this illustrative embodiment, may operate in a networked environment using logical connections to one or more remote computers, such as remote computer 170. The computer 14 may also communicate with treadmill 12 via a LAN and optionally communicate with communication system 18 and treadmill 20 via a WAN and optionally remote computer 170. Generally, each remote computer 170, communication system 18, and treadmill 12, 20 may be or include the structure and perform the function of another personal computer, a server, a router, a network PC, a peer device, or other common network node, and typically includes many or all of the elements described above relative to computer 14, although only one memory storage device 172 and its associated application program 174 has been illustrated in FIG. 7. The logical connections depicted in FIG. 7 include local area network (LAN) 176 and a wide area network (WAN) 178 that are presented here by way of example and not limitation. Such networking environments are commonplace in office-wide or enterprise-wide computer networks, intranets and the Internet.

When used in a LAN networking environment, typically computer 14 is connected to the local network 176 through a network interface or adapter 180 that communicates via one of a variety of communication line connections, such as those described previously. When used in a WAN networking environment such that computer 14 may communicate with communication system 18, computer 14 may include a modem 182, a wireless link, or other means for establishing communications over the wide area network 178, such as the Internet. The modem 182, which may be internal or external, is connected to computer bus 124 via serial port interface 164. In a networked environment, program modules depicted relative to computer 14, or portions thereof, may be stored in the remote memory storage device. It will be appreciated that the network connections shown are exemplary and other means for establishing communications over wide area network 178 may be used.

Various transmission or communication protocols may be used to enable computer 14 to receive and transmit data through network 16. In one embodiment of the present invention, computer 14, and more specifically, network interface 180 or serial port interface 164, may use TCP/IP communication protocol. Alternatively, computer 14 may use connection orientated or connectionless networks via asynchronous transfer mode (ATM) technology, X.25 protocol, Frame Relay protocol, packet switching protocols, circuit switching protocols, dynamic packet switching protocols, 802.11RF protocol, home network protocols, CSAFE 1, CAN protocols, and the like to transmit and receive data through network 16.

The term "transceiving" as used herein will mean transmitting, receiving, or a combination of both transmitting and receiving data. The term "packetized", "packetizing", and the like, as used herein will mean data that has been manipulated into one or more packets according to a packet switching protocol for transmission via network 16, such as may be understood in light of the following teaching and knowledge within the art.

Generally, the packet contains the destination address in addition to the data. Each packet may be transmitted individually or may be combined or pooled with other packets of data going to similar destinations, such as audio data, video data and/or control signals. The packets of data or pooled data are optionally compressed and encapsulated for transceiving across network 16, where each packet may follow different routes to its destination. Once all the packets of a specific data message arrive at the destination, they are decompiled and deencapsulated into the original data. The packets may be prioritized according to content so that certain packets of data are delivered to computer 14, and hence treadmill 12, through network 16 faster than the other packets of data. For example, in a live-on-live exercise program situation audio and video data or signals are transceived faster than the control signals. Therefore, according to one embodiment, an individual may communicate with a trainer in real time without the need to interrupt the real-time communication between the trainer and the user so that one or more control signals may be delivered to the exercise device. An advantage of packetizing data, therefore, is that computer 14, translator device 13, and/or treadmill 12 may optimize its performance according to the available bandwidth of the communication connection line with network 16 without the need to interrupt the real-time communication between a user and a trainer.

The discussion above describes a computer detached from treadmill 12; however, as appreciated and stated earlier, all or portions of computer 14 may be optionally incorporated within treadmill 12. As such, some or all of the various elements of computer 14 may be incorporated within control panel 22, or alternatively within tread base 26. In various other configurations of the present invention, therefore, control panel 22 may include one or more magnetic hard disk drives, magnetic disk drives, optical disk drives, and associated interfaces. Control 22, therefore, may be capable of accessing programming that is stored on computer diskettes, CD ROMs, DVDs, and the like. Additionally, control panel 22 may optionally include a keypad integrally formed therein, or optionally include a standard keyboard interface that may enable a user to communicate with treadmill 12. The keypads and keyboard enable the user to control the operation of treadmill 12, and optionally communicate with communication system 18 and other hardware and/or software modules that may be accessible via network 16.

As depicted in FIG. 1, computer 14 may optionally communicate with translator device 13 that is configured to manipulate signals transmitted and received between computer 14 and treadmill 12. Specifically, translator device 13 may be used when computer 14 and treadmill 12 are incapable of directly communicating one with another. Translator device 13 includes one or more processors that convert the signals passed therethrough to a form that the device to receive such signals might understand. For example, computer 14 may communicate with translator device 13 via a serial connection, while treadmill 12 may only communicate with devices that deliver data via a serial I²C connection or protocol. As such, translator device 13 is configured to manipulate the serial signal received from computer 14 into a signal capable of being delivered via a serial I²C connection or bus.

It may be appreciated by one skilled in the art that translator device 13 may convert various types of signal to various other forms capable of being transmitted to various interfaces. For example, translator device 13 may use a SPI bus, a microwire bus, a microbus, a CAN protocol, a CSAFE 1 protocol, a home network protocol, TCP/IP communication protocol, an asynchronous transfer mode (ATM) technology, X.25 protocol, Frame Relay protocol, packet switching protocols, circuit switching protocols, dynamic packet switching protocols, 802.11RF protocol, serial, parallel, USB, or wireless connection, and the like. Additionally, the structure and function of translator device 13 may be completely or partially incorporated within treadmill 12, computer 14, or a combination thereof.

Generally, computer 14 and/or translator device 13, collectively and/or individually are examples of a communicating mechanism, communicating with the interface means (e.g., the input devices of console 22 that gather a signal from the user). In one embodiment, the communicating mechanism enables real-time transmission of a first signal to: a live trainer (e.g., on treadmill 20), a stored trainer (e.g., communication system 18), another user, or a third party 21, for example. The communicating mechanism may also receive a packetized second real-time signal from any of these sources.

The second real-time signal may be an audio or visual signal directed to the user and/or a control signal directed to a device, such as an exercise device 12, for example. The audio and/or visual signal and the control signal may come from the same source, such as a trainer 20. In one embodiment, however, the second real-time signal comprises an audio and/or visual signal from one source and a control signal from another source. For example, the audio and/or visual signal may come from a live trainer, while the control signal may come from a website or vice versa. Optionally, the audio, visual, and control signals are each directed both to the user and to the exercise device, such as when the control signal is an audible signal directed to a microphone connected to the device.

Computers 14 and/or translator device 13 portions are collectively or individually examples of a communicating mechanism. Additionally, when portions of one more computers 14 and/or translator devices 13 are incorporated within treadmill 12, such portions are collectively or individually examples of a communicating mechanism. Examples of such a communicating mechanism of the present invention may comprise (i) a single structure that enables transmission of the first signal and/or receives the packetized second signal or (ii) a first structure that enables transmission of the first signal and a separate second structure that receives the packetized second signal. Any of these communicating mechanisms are examples of structures capable of performing the function of communicating means, communicating with the interface means, for receiving a packetized second signal (such as a real-time signal), and optionally, for enabling transmission of the first signal (such as a real-time signal).

In one embodiment, the communicating means only receives the second signal. For example, upon merely activating a user input device, such as by turning the power of the exercise device or other device on, a first signal is "gathered from the user," but is not transmitted. Instead, the first signal merely activates the power and enables the communicating mechanism to receive any second packetized signal that may be broadcast to the exercise device. Such a broadcast may be from a communication system 18, such as by wireless transmission, RF transmission, or other means known to those skilled in the art. In another embodiment, the communicating mechanism transmits the first signal and receives the second signal.

Additionally, computer 14 and/or translator device 13, collectively and/or individually are examples of structures capable of performing the function of control means, communicating with the exercise mechanism, for receiving one or more packetized control signals from the communication system indicative of the selected exercise program and for changing one or more operating parameters of the exercise mechanism based upon the selected exercise program and the one or more packetized control signals.

Figure 8:
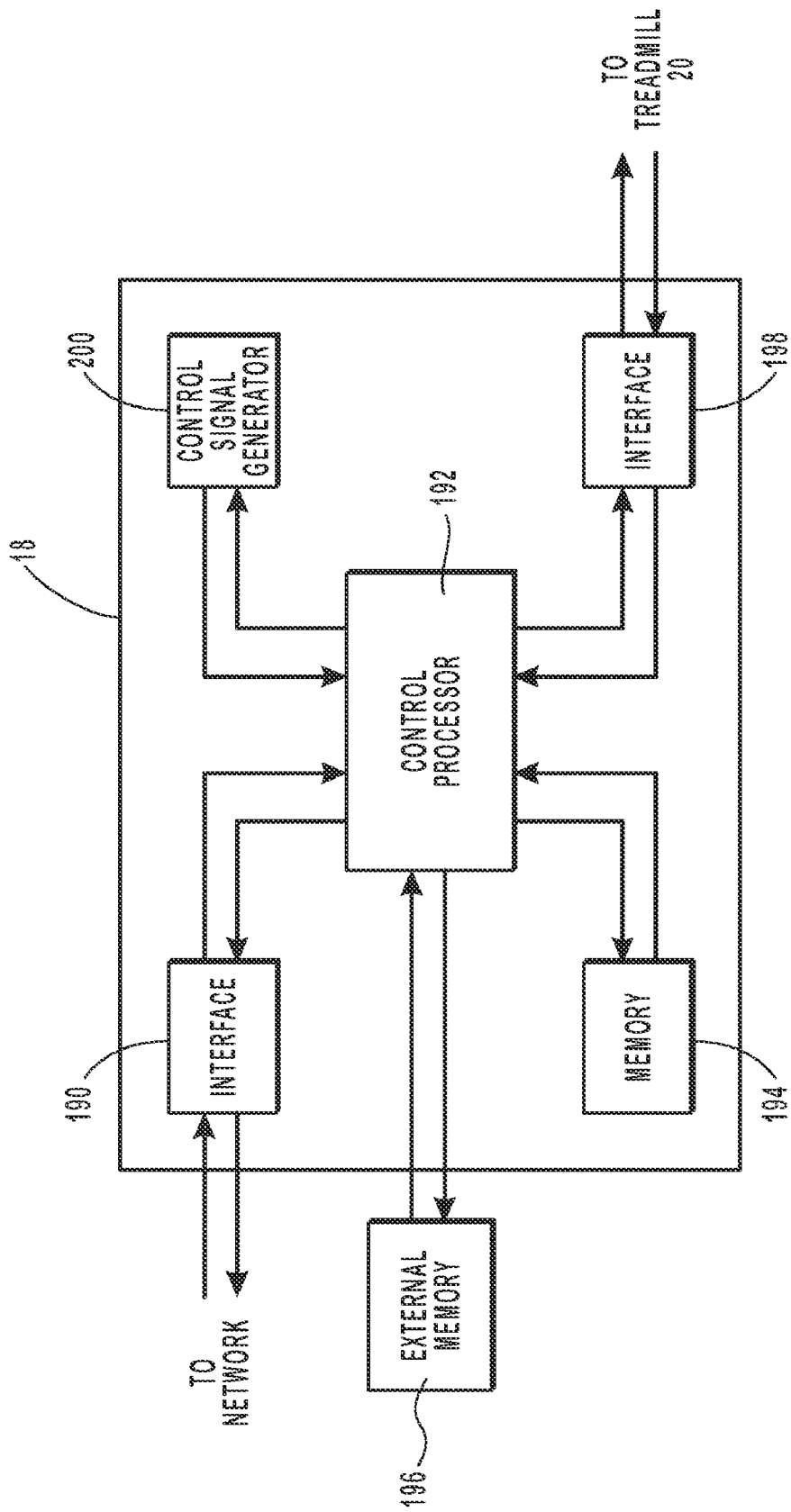
FIG. 8 is a functional block diagram of a communication system of the exercise system of FIG. 1.

As discussed above with respect to FIG. 1, computer 14 may transceive one or more signals to and from communication system 18 through network 16. Referring now to FIG. 8, a schematic block diagram of communication system 18 is illustrated. For simplicity, only the most relevant hardware components are illustrated in FIG. 8. It may be appreciated by one skilled in the art that various other components may be included within communication system 18 depending on the particular use and function of communication system 18.

As depicted, communication system 18 includes an interface 190 that communicates with a control processor 192 and an interface 198. Interface 190 is configured to transceive one or more signals to and from computer 14 and treadmill 12 via network 16. Such signals may include audio and visual signals of the user exercising, the status of the exercise device, such as active status, deactivated status, standby status, data and information about the user, such as heart rate, blood pressure, and the like that has been gathered by one or more health monitoring devices. Such devices may include but are not limited to electrodes, transducers, other ECG monitoring devices, a pulse watch, a heart rate monitor, an EKG electronic detection device, an ECG electronic detection device, and the like. Similarly, interface 198 enables communication system 18 to transmit the above signals to and receive various signals from a trainer at treadmill 20 via network 16 (FIG. 1). Such received signals may include audio, visual, and/or control signals. Alternatively, the trainer at treadmill 20 may receive no signals, in the case where communication system 18 controls treadmill 12 without a trainer at treadmill 20.

Each interface 190, 198 therefore, may be of a variety of types depending on the particular communication line connection used in system 10 and the particular transmission protocols used by computer 14, treadmill 12, translator device 13, or treadmill 20. For example, interfaces 190, 198 may be a wireless interface, may use infrared (IR), radio frequency (RF), microwave technology, satellite, blue tooth transmission, home network protocols, or various other protocols and technology as known by one skilled in the art. Alternatively, interfaces 190, 198 may be a modem, cable modem, ADSL connection, ISDN, Ethernet, or similar other connections. Interfaces 190, 198 either solely or in combination with the other elements of communication system 18, may use various transmission protocols to transceive data between treadmill 12 and treadmill 20 via communication system 18. It may be appreciated by one skilled in the art that interfaces 190, 198 need not be the same, so long as they may communicate with control processor 192, and the other appropriate elements of system 10.

Communicating with interface 190 and interface 198 is a control processor 192. Control processor 192 is configured to transceive signals through interface 190 and manipulates the same based on selected programming selected by: (i) the user; (ii) a trainer located at treadmill 20; (iii) a third party 21; or (iv) a combination thereof. Subsequently, control processor 192, optionally in combination within interface 190 or 198, prepares the selected programming (i.e., audio and video signals with associated control signals, if any) for transmission to treadmill 12 and 20. Control processor 192 also preferably "packetizes" the programming so that packets of information may be "streamed" or downloaded through respective interfaces 190, 198 to computer 14, and subsequently treadmill 12, or to treadmill 20. Each packet of data may be sent individually, and may follow a different path across network 16 to reach computer 14 (or treadmill 12). Upon reaching computer 14 (or treadmill 12 or 20), the data may be "buffered" so that the data may be delivered to the user or trainer in real-time.

Generally, control processor 192 may include one or more micro-controllers, central processing units, state machines, programmable logic arrays, network logical arrays, or gates, ASIC processors, software-based controllers, combination logic, combinations thereof, and a variety of other controllers known by one skilled in the art to manipulate data transceived between treadmill 12, communication system 18, and/or treadmill 20.

Control processor is one example of a structure capable of performing the function of means for synchronizing and packetizing the control signals with the programming and delivering the packetized control signal to the user device. It may be appreciated that various other control processors and means are appropriate and known to those skilled in the art.

Communicating with control process 192 is memory 194 and external memory 196. As shown, external memory 196 is optionally included, depending on the particular data storage needs of communication system 18. For example, memory 194 and/or external memory 196 may include physical information regarding the operation of treadmill 12. Additionally, memory 194 and/or external memory 196 may be one structure capable of performing the function of storage means for storing programming. Memory 194 and/or external memory 196 may, therefore, include or be configured to access one or more audiocassette tapes, compact disks (CDs), mini disks (MDs), computer diskettes, videotapes, laser disks (LDs), digital videodisks (DVDs), computer diskettes, or such other media capable of storing audio and/or video programming, with associated control signals. Additionally, memory 194 and/or external memory 196 may store a particular set of control signals in synchronization with the above-recited audio and video media programming. In light of the teaching contained herein, it may be appreciated by one skilled in the art, that either memory 194 and/or external memory 196 may take the form of or include a database structure that enables access to the various programming stored therein.

Also communicating with control processor 192 is control signal generator 200. Control signal generator 200 includes circuitry and/or software to generate the control signals that are synchronized with the audio and video programming retrieved from memory 194 and/or external memory 196 or alternatively transmitted from treadmill 20 through interface 198. Therefore, control signal generator 200 may include one or more micro-controllers, central processing units, state machines, programmable logic arrays, network logical arrays, or gates, ASIC processors, software-based controllers, combination logic, combinations thereof, and a variety of other controllers known by one skilled in the art to generate one or more control signals.

Control signal generator 200 is one structure capable of performing the function of means for generating one or more control signals. One skilled in the art may identify various other configurations of means for generating one or more control signals.

Various configurations are applicable for encoding a control signal on a carrier signal included with the audio and video programming. Following hereinafter is a discussion of one format for encoding the control signals. It should be understood that the method of encoding set forth herein is representative only and is not intended to limit the scope of this invention or to limit the various other alternative means or methods by which a control signal may be transmitted to treadmill 12 and/or optionally treadmill 20. Additionally, any number of encoding schemes, which are known to those skilled in the art, may be used to carry out the desired function and are encompassed within, the scope of the present invention.

In one embodiment, the control signals generated by control signal generator 200 are carried on a two (2) kHz carrier signal, with each control signal consisting of two transmission bursts, each burst having three bytes of data. The second burst is intended to exactly duplicate the first burst for error checking purposes. The first byte of data of each burst, generated by control signal generator 200, in this illustrative embodiment, indicates the desired speed of the treadmill, while the second byte of data indicates the desired incline of the tread base 26, and the third byte is a check sum of the first and second bytes. For other exercise devices the first and second bytes may represent other operating parameters, like resistance of an elliptical device or cycle device. It may be appreciated that each burst may include less or more than 3 bytes of data, depending on the different type of device that communicates with communication system 18. As configured, the control signal uses a standard RS-232 protocol. Alternatively, control signals may also use other serial or parallel protocols, such as RS-422, RS-423, universal serial bus (USB) and various other communication protocols known by one skilled in the art in light of the teaching contained herein.

In one embodiment, each control signal includes both the first burst and the second burst. Generally, the control signal is typically left in one quarter second in duration. Each byte consists of eight bits of data, giving a high degree of resolution for controlling the exercise device operating parameters, such as treadmill speed and the degree of incline. In one embodiment, each time a control signal is inserted into the programming, the control signal entirely suppresses the audio portion of the programming for the duration of the control signal. Alternatively, and more preferably, the control signal does not entirely suppress the audio portion of the programming. Rather the control signal overlays the programming so that the programming is uninterrupted. As a result, the control signals are audible to the user which also provides an audible cue or warning to the user that one or more operating parameters of treadmill 12 is about to change. Alternatively, the control signals are inaudible to the user, but may be analyzed by computer 14 and/or treadmill 12. The inaudible signals may, therefore, dictate an additional or alternate manner by which the user is signaled of an impending change in one or more operating parameters of treadmill 12. For example, in addition to an audio signal, the control signal may include a video signal, such as a flashing red border that may appear around the exterior perimeter of the video output device 94 and overlap the video display to inform the user of a change in operating parameters of treadmill 12. It may be appreciated by one skilled in the art that a combination of both audio and video indicators, whether or not the programming is modified, such as the audio being eliminated, or the video being eliminated, may be used to inform the user of an impending change in operating parameters.

As alluded to above, the control signals are detectable by computer 14 or treadmill 12, that verifies the control signal has the proper 2 kHz carrier frequency, checks to make sure that the control signals otherwise properly formatted, and check for errors. If the signal is approved, the signal is delivered to the appropriate controllers for varying the operating parameters of treadmill 12.

Generally, the operation of communication system 18 varies depending on the particular manner by which the programming is to be delivered to user on treadmill 12. In one configuration, treadmill 20 is similarly configured to treadmill 12, previously described. In such a case, when an individual wishes to perform an exercise program in real-time with a distantly located trainer training on treadmill 20, the trainer, preceding the scheduled exercise time, accesses or "logs on" to communication system 18. Upon logging onto communication system 18, the trainer prepares the desired exercise program or alternatively selects a stored control signal profile that is synchronized to the desired program from memory 194 and/or external memory 196. At the scheduled time for a live-on-live treadmill exercise program, both the user of treadmill 12 and the trainer located at treadmill 20 access communication system 18. The trainer activates the control signal profile, which is delivered to control processor 192. Control processor 192 delivers to both treadmill 12 and treadmill 20 both the audio and/or video programming and the desired control signals to vary the operating parameters of each treadmill 12, 20 in synchronization with the audio and/or video programming. Control processor 192, optionally in combination with interfaces 190, 198 prepares, the control signals with the audio and video signals in accordance with the communication protocol that computer 14, translator device 13, treadmill 12 and/or treadmill 20 uses. Alternatively, control processor 192 may deliver control signals to treadmill 12 to vary the operating parameters thereof, while sending an audio and/or video representation of the exercise profile (i.e., speed, distance, time, inclination of the exercise device) of the exercise program delivered to the user, so that the trainer may then manually vary the operating parameters of treadmill 20 as desired. The delivery of the programming including the control signal may be termed a packetized second signal (preferably a packetized second real-time signal).

In one embodiment, changes made by the trainer on treadmill 20 are translated into control signals that are delivered to treadmill 12 to vary the operating parameters therein. As such, treadmill 20 includes one or more sensors that identify changes made to the operating parameters of treadmill 20 and deliver signals representative of such changes to control processor 192. Upon receiving the sensed information, control processor 192 delivers a request to control signal generator 200. Control signals generator 200 subsequently generates a control signal associated with the actions taken by the trainer on treadmill 20 and passes those signals through control processor 192, interface 190, and optionally computer 14 to treadmill 12. The delivery of the programming including the control signal may be termed a packetized second signal or a packetized second real-time signal.

In still yet another configuration, treadmill 20 is configured to include control signal generator 200. In this particular configuration, as a trainer performs a programming workout, whether such programming is stored on treadmill 20 or alternatively accessed through communication system 18, control signal generator 200 creates the bursts of bytes in accordance with changes made by trainer made on treadmill 20. As such, the control signals are sent from treadmill 20 through interface 198 to control processor 192. Control processor 192 then passes the control signals along with the audio and video programming, through interface 190 to treadmill 12. The delivery of the programming including the control signal may be termed a packetized second signal (preferably real-time).

It may be appreciated by one skilled in the art, that the various above-described configurations are only illustrative of the manner by which treadmill 20 may control the operation of treadmill 12 either directly or alternatively indirectly through the use of control signal generator 200 and the other components and modules of communication system 18.

Figure 9:
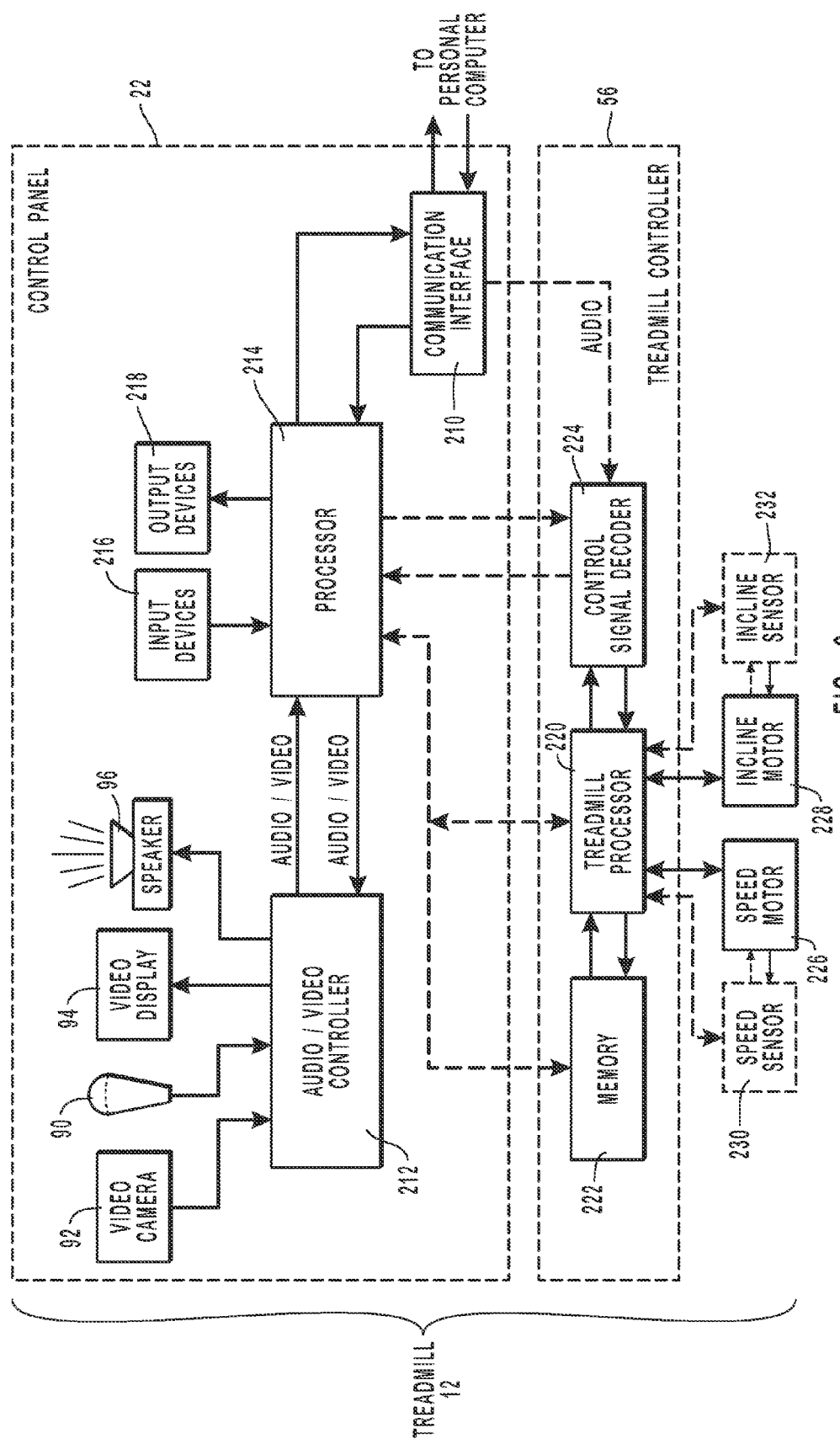
FIG. 9 is a functional block diagram of the treadmill and computer with associated translator box of FIG. 1.

Following hereinafter, and depicted in FIG. 9, is a function of block diagram of one embodiment of treadmill 12. In this particular configuration, the functionality of personal computer 14 is not incorporated within treadmill 12; however, as may be appreciated by one skilled in the art, computer 14 may be incorporated within control panel 22 or other portions of treadmill 12. This embodiment enables true interactive communication between a user operating treadmill 12 in his/her own home, and a personal trainer located at a remote location, such as where treadmill 20 is located. Additionally, the trainer may observe the user in real-time and control the user's treadmill 12 remotely and in real-time via communication system 18 without interrupting the real-time audio and video programming.

As shown, treadmill 12 includes control panel 22 and treadmill controller 56. Although shown separated, it may be appreciated that portions of each may be combined together, thereby simplifying the modules and components of the present invention. Control panel 22, in this embodiment, incorporates audio input device 90 in the form of a microphone and a video input device 92 in the form of a video camera for gathering audio and video signals to be transmitted to communication system 18. As mentioned previously, the audio and video receivers need not be incorporated within control panel 22 or other portion of treadmill 12. Rather, audio input device 90 and video input device 92 may be located distant from treadmill 12, while having sufficient detection controls to receive the requisite audio and video signals.

Signals from audio input device 90 and video input device 92 are delivered to an audio/video controller 212. Audio/video controller 212 is configured to manipulate the audio and video signals received from input devices 90, 92 in preparation for transmission to a processor 214. Audio/video controller 212, therefore, includes one or more amplifiers, microcontrollers, central processing units, state machines, programmable logic arrays, network local logical arrays, or gates, ASIC processors, software based controllers, combination logic, or combinations thereof to both manipulate audio and video signals that are to be transmitted or received by input devices 90, 92 and associated output devices 94, 96. Additionally, audio/video controller 212 may include memory, such as a buffer, to store and aid with real-time transmission and delivery of the audio and video signals. It may be appreciated by one skilled in the art that various audio/video controllers 212 are applicable and known in the art in light of the teaching contained herein.

Communicating with audio/video controller 212 is processor 214. Processor 214 converts the audio and video data received through audio/video controller 212 into the desired form that is capable of being transmitted to communication system 18 via communication interface 210. As such, processor 214 may perform various operations on the data to be delivered to communication system 18, such as, but not limited to, packing, encrypting, splitting, and the like. Additionally, processor 214 may be configured to perform various operations to data received from communication system 18, such as, but not limited to, the reverse of the above operations. Generally, processor 214 may have various configurations to perform the above-described function as known by one skilled in the art. For example, processor 214 may take the form of one or more micro-controllers, central processing unit (CPU), state machines, programmable logic arrays, or network of logical gates, ASIC processor, software-based controllers, a combination of these components, or a variety of other controllers.

According to another aspect of the present invention, processor 214 may receive various inputs from one or more manually operated input devices 216, such as manual override button 84, scaling controls 84, and other controls and buttons known to one skilled in the art in light of the teaching contained herein. In response to such inputs, processor 214 may vary the operating parameters of treadmill 12 and provide the user with notification of such change in the operating parameters of treadmill 12 via output devices 218 and/or video output device 94 and audio output device 96. Processor 214, therefore, is one structure capable of performing the function of means for controlling the operating parameters of the exercise mechanism in real-time and one structure capable of performing the function of control means for receiving one or more packetized control signals from a communication system indicative of a selected exercise program and changing one or more operating parameters of the exercise mechanism based upon the selected exercise program and the one or more packetized control signals.

Communicating with processor 214, in one embodiment, is communication interface 210 that enables treadmill 12 to transceive data, such as packetized data, via a communication line. Communication interface 210, in one embodiment, is a modem. Depending on the particular communication manner used to communicate with communication system 18, different communication interfaces 210 may be used at different communication line connections. For example, the communication line connection may include existing broadcast technology, including television broadcast over the airwaves, cable or cable modems, satellite, telephone lines, whether analog or digitally based, the internet, DSL, G-Lite, wireless technology, other high-speed data connections, or any other suitable transmission technology or medium. As such, communication interface 210 is compatible with existing conventional broadcast technologies and can interface with existing audio and/or video components commonly found in homes, thereby reducing the overall cost of the exercise device and reducing barriers to accessing communication system 18.

Communicating with processor 214 and optionally communicating with communication interface 210 is treadmill controller 56. As illustrated in FIG. 9, treadmill controller 56 communicates with control panel 22. Generally, treadmill controller 56 may communicate with control panel 22 by an I²C bus, a SPI bus, a microwire bus, a microbus, and the like.

In one embodiment, treadmill controller 56 includes a treadmill processor 220, memory 222, and a control signal decoder 224. Treadmill processor 220 is configured to control the operation of speed motor 226 and incline motor 228 that controls the speed and incline of treadmill 12. Treadmill processor 220, therefore, is one structure capable of performing the function of means for controlling the operating parameters of the exercise mechanism in real-time and one structure capable of performing the function of control means for receiving one or more packetized control signals from a communication system indicative of a selected exercise program and changing one or more operating parameters of the exercise mechanism based upon the selected exercise program and the one or more packetized control signals.

Treadmill processor 220 is optionally controlled by processor 214 or by control signal decoder 224 in response to the various signals received through communication interface 210 from communication system 18. Alternatively, treadmill processor 220 may be controlled by signals obtained from memory 222, via input devices 216, audio input device 90 and video input device 92. Treadmill processor 220 may include various components and modules to perform the desired function. For example, treadmill processor 220 may include one or more micro-controllers, central processing unit (CPU), state machines, programmable logic arrays, or network of logical gates, ASIC processor, software-based controllers, combination logic, a combination of these components, or a variety of other controllers.

Controller 212, processor 214, interface 210, and treadmill processor 220 are collectively and individually examples of structures capable of performing the function of communicating means, communicating with the interface means, for receiving a packetized second signal, and optionally, for enabling transmission of the first signal.

Both processor 214 and treadmill processor 220 are capable of receiving and transmitting feedback signals from the various elements of treadmill 12, for example, feed back from drive motor 226 and incline motor 228. Each processor 214, 220 is capable of converting the feedback signals into signals for the video output device 94 or monitor 166 communicating with computer 14. The particular feedback signals received from speed motor 226 and incline motor 228 may be stored in registers or memory modules.

Treadmill 12, as depicted, optionally includes one or more sensors, such as belt speed sensor 230 and incline sensor 232. Each sensor 230, 232 gathers a particular operating parameter of treadmill 12 (speed of belt 42 (FIG. 4) and incline of tread base 26), such that control panel 22 may present outputs via the output devices that are indicative of the present operating state of treadmill 12 at any given point in time. Treadmill 12 may include other sensors that gather various other operating parameters, such as, but not limited to, maximum pulse and heart rate, average pulse and heart rate, target heart rate, length of workout session, and the like. Additionally, sensors 230, 232, optionally in combination with one or more other sensors, may determine whether an individual is actually exercising on treadmill 12 and deliver a feedback signal to processor 214 that informs communication system 18 and/or the trainer. Furthermore, sensors 230, 232, optionally in combination with one or more other sensors, may calculate whether the individual is a juvenile and stop treadmill 12 in the event that the user is a juvenile.

As discussed earlier, system 10 enables a user of treadmill 20 to communicate with and control one or more operating characteristics or parameters of treadmill 12. There are various manners by which treadmill 12 may be controlled by communication system 18 solely or in combination with treadmill 20 or a third party 21. Following hereinafter is a continued discussion of the operation of the illustrated embodiment of treadmill 12 depicted in FIG. 9.

During operation of treadmill 12 a user initially inserts a dead-man key (not shown) within port 98 of control panel 22 (FIG. 6). Upon insertion of the dead-man key, treadmill 12 is capable of being operated, i.e., power is allowed to flow to the various internal and external components of treadmill 12 and treadmill 12 has an active status. Once activated, a user may optionally connect to communication system 18 or use a stored or manually defined exercise program or workout. In the event that the user wishes to connect to communication system 18, in one embodiment, a user activates iFit.com button 82 (FIG. 6), thereby initiating the hardware and/or software modules within either treadmill 12 or computer 14 to create a connection with communication system 18. Alternatively, upon placing treadmill 12 in active status, treadmill 12 may automatically connect to communication system 18.

Once a link is achieved and a user optionally has provided a password and user identification, a user may select either stored or live-on-live exercise programs. Following the user selection, programming, whether live or stored is delivered (optionally in real-time) to communication interface 210 via one or more of a variety of communication line connections, whether such connections are digital, analog, serial, parallel, or a combination thereof. The particular configuration of communication interface 210 may vary based upon the particular communication line connection used.

It may be appreciated by one skilled in the art that the exercise program may be displayed to the user in a variety of manners, depending on the particular signals received from communication system 18 or trainer device 20. For example, the programming may include an exercise profile that periodically or continually appears on video output device 94. Alternatively, the programming may solely include the above-described exercise profile, thereby enabling the user of treadmill 12 to view educational or entertainment programming via video output device 94 during their exercise program.

Upon receiving the programming, communication interface 210 may optionally deliver the audio signal to control signal decoder 224 that identifies the control signal. In another setting, communication interface 210 may deliver both the audio and video signals, with the control signal, to processor 214 for manipulation and distribution to the appropriate hardware components, and/or software modules. Such delivery of programming may be performed through use of a general-purpose bus or a variety of other buses and protocols, such as an I²C bus, SPI bus, Microwire bus, Microbus, CAN protocol, home network protocol, or the like. Additionally, the control signals, and the audio and the video signals may be delivered using the CSAFE 1 protocol or equivalent thereof for various other types of devices not within the field of exercise devices.

When communication interface 210 delivers all signals to processor 210, processor 214 separates the audio, video, and control signals and optionally delivers them to audio/video controller 212, control signal decoder 224, treadmill processor 220, or memory 224. For example, in one configuration processor 214 may optionally deliver portions of the audio and video signals to control signal decoder 224, either directly or through treadmill processor 220 such that the audio and video signals are "buffered" in accordance with "streaming" technology. If the available bandwidth does not allow real-time streaming of audio and video signals, video frames and the audio signals may be separated and transceived so that a segmented display is provided with real-time audio signals. Although segmenting of video frames is not preferred it is one possible alternative method of streaming audio and video signals. In another configuration, upon receiving the signals from processor 214, control signal decoder 224 may optionally store the complete audio and video signals for an entire program before treadmill 12 may access such signals. In yet another configuration, processor 214 may optionally deliver only the audio signal and the control signal to treadmill processor 220 that may include the functionality of control signal decoder 224 therein. The particular manner by which treadmill processor 220 retrieves either the encoded control signal or the decoded control signal may vary from configuration to configuration depending on the particular form of treadmill 12.

Generally, control signal decoder 224 either individually or collectively with processor 214 and/or treadmill processor 220 is one structure capable of performing the function of means for decoding the control signal having an input and an output. One skilled in the art may identify various other configurations of a means for decoding the control signal having and input and an output. For example, treadmill processor 220 and/or processor 214 may include a control signal decoder and hence be a means for decoding the control signal having an input and an output.

Following manipulation of the control signals to obtain the control instructions, treadmill processor 220 performs the control process on the various components of treadmill 12 as dictated by the control instructions. For example, treadmill processor 220 may cause motor 46 to speed up thereby accelerating belt 42 or alternatively cause motor 60 to rotate thereby raising or lowering tread base 26. Motors 46, 60 and 226, 228 are structures capable of performing the function of means, electrically coupled to the output of the decoding means for driving the moveable element in response to the decoded control signal. It may be appreciated by one skilled in the art that the control instructions may cause various other changes to the operating parameters of treadmill 12, and other devices. Similarly, various means for driving the moveable element in response to the decoded control signal. For example, the means may vary depending on the particular type of exercise device used.

While treadmill processor 220 is either decoding the control signal from the audio signal received from communication system 18 or merely activating speed motor 226 and/or incline motor 228, processor 214 delivers the audio and video signals received through communication interface 210 to audio/video controller 212. Audio/video controller 212 manipulates the signals received and passes the audio signal to audio output device 96 and the video signal to video output device 94. Optionally, processor 214 may send portions of the audio or video signals to the output devices 218 to provide the user with multiple sources of representations of the current operating parameters of treadmill 12, or exercise device.

In another alternative configuration of the present invention, the audio, video, and control signals received by communication interface 210 are delivered to processor 214 for manipulation and delivery to audio/video controller 212. In such a case, the video data is displayed on video output device 94 while the audio signal including the control signal is transmitted to audio output device 96. In this configuration, audio input device 90 or a second audio input device (not shown) is configured to receive various control signals that are delivered by audio output device 96 and pass those back to processor 214. The control signals are subsequently decoded and treadmill processor 220 may activate speed motor 226 and/or incline motor 228 in accordance with the delivered control signals.

Generally, communication interface 210, processor 214, audio/video controller 212, treadmill processor 220, and/or control signal decoder 224 are collectively and individually examples of a controller, responsive to the packetized second signal, configured to control the operating parameters of the exercise mechanism (preferably in real-time). Additionally, such controller is a structure capable of performing the function of control means, communicating with the exercise mechanism, for receiving one or more packetized control signals from the communication system indicative of the selected exercise program and for changing one or more operating parameters of the exercise mechanism based upon the selected exercise program and the one or more packetized control signals. It may be appreciated by one skilled in the art that the control means may have various other configurations.

Following hereinafter is a generalized discussion of a number of features of an exercise system, exercise devices, methods, computer products, and computer readable media associated with the teaching and disclosure of the present invention. Referring now to FIGS. 10-19, a system 250 is illustrated. The majority of the features described with respect to system 10, also apply to system 250.

Generally, this embodiment of the present invention may comprise one or more hardware components, such as those described above and illustrated in FIGS. 1, 7, and 10, and various special-purpose or general-purpose computers. Embodiments within the scope of the present invention also include computer-readable media for carrying or having computer-executable instructions or data structures stored thereon. Such computer-readable media can be any available media that can be accessed by a general-purpose or special-purpose computer and the hardware and/or software modules associated with system 10 (FIG. 1). By way of example, and not limitation, such computer-readable media can comprise RAM, ROM, EEPROM, CD-ROM, or other optical disk storage, magnetic disk storage, or other magnetic storage devices, or any other medium which may be used to carry or store desired program code means in the form of computer-executable instructions or data structures and which may be accessed by a general-purpose or special-purpose computer. When information, such as one or more signals or programming is transferred or provided over network 16 or another communications connection (either hardwired, wireless, or a combination of hardwired or wireless) to treadmill 12, translator device 13, computer 14, communication system 18, and/or treadmill 20, such devices properly view the connection as a computer-readable medium. Thus, any such a connection is properly termed a computer-readable medium. Combinations of the above should also be included within the scope of computer-readable media. Computer-executable instructions may include, for example, instructions and data which cause a general-purpose computer, special-purpose computer, or special-purpose processing device to perform a certain function or group of functions.

Although not required, the present invention will be described in the general context of computer-executable instructions, such as program modules, that may be executed by one or more computers in various network environments, such as within the environments illustrated in FIGS. 1, 7, and 10. Generally, program modules include routines, programs, objects, components, data structures, etc. that perform particular tasks or implement particular abstract data types. Computer-executable instructions, associated data structures, and program modules represent examples of program code means for executing steps of the methods disclosed herein. The particular sequence of such executable instructions or associated data structures represents examples of corresponding acts for implementing the functions described in such steps.

According to this illustrative embodiment of the present invention, a distantly located personal trainer performing an exercise on one treadmill in real-time may control one or more operating parameters of an exercise device used by a user performing an exercise program. However, it may be appreciated that the systems, methods, and devices of the present invention may be implemented and utilized in various other situations and with various other exercise devices or other devices unrelated to exercise devices. The systems and methods of the present invention may be implemented using a variety of hardware and/or software modules and include a variety of computer network configurations, including but not limited to multiple computers and/or exercise devices that are connected via the Internet, LANs, WANs, and the like.

To more easily explain the function and structures of system 250, reference will now be made to FIG. 10 that is a block diagram illustrating one embodiment of the present invention. As shown, system 250, that is similar to system 10, includes a number of user modules 252a-252n that represent, in this embodiment, multiple exercise devices, translator devices 13, and/or computers 14, whether such exercise devices, translator devices 13, and/or computers 14 are located in the same area, or distantly located one with another, such as at a number of user's homes. Alternatively, as discussed earlier, user modules 252a-252n may take the form of various other devices known by one skilled in the art. For example, the exercise devices may include treadmill 12, ellipticals, cycles, steppers, hikers, climbers, Nordic type exercise devices, and other various types of exercise devices as known by one skilled in art.

Generally, user modules 252a-252n include one or more exercise mechanisms with one or more moveable elements that enable a user to exercise during an exercise program, whether such exercise program requires anaerobic exercise, aerobic exercise, or a combination thereof. Therefore, the modules of each user module 252a-252n may be structures capable of performing the functions of: (1) control means for receiving one or more packetized controls signals from the communication system (communication module) indicative of a selected exercise program and changing one or more operating parameters of the exercise mechanism based upon the selected exercise program and the packetized controls signals; (2) interface means, communicating with the exercise mechanism, for gathering a first real-time signal from the user; (3) communicating means, communicating with the interface means, for receiving a packetized second signal, and optionally, for enabling transmission of the first signal; (4) means for reproducing the second signal; (5) means for controlling the operating parameters of the exercise mechanism; (6) means for decoding the control signals; and (7) means for driving the moveable element in response to the decoded control signals.

In one embodiment, user modules 252a-252n communicate with a communication module 254, via network 16. In one embodiment, communication module 254 has a similar configuration to that of communication system 18 and is capable of transmitting and receiving data from user modules 252a-252n. As such, communication module 254 is able to "transceive" information and data to and from the various modules, components, and other hardware and/or software modules of system 250.

Generally, in one illustrative embodiment, communication module 254 is configured to act as an intermediary module between user modules 252a-252n and the various other modules of system 250. Communication module 254, therefore, enables user modules 252a-252n to communicate with and select one or more exercise programs, whether based on a live-on-live request or recorded exercise programs. The structures and functions related to communication module 254 will be discussed in greater detail hereinafter.

Optionally communicating with communication module 254 is one or more trainer modules 256a-256n. As illustrated, communication module 254 is directly communicating with trainer modules 256a-256n. Alternatively, trainer modules 256a-256n may communicate with user modules 252a-252n through network 16, therefore enabling user modules 252a-252n to communicate with trainer modules 256a-256n through network 16 without interacting with communication module 254, such as illustrated in FIG. 1, where a user treadmill 12 may communicate directly with a trainer treadmill 20.

Trainer modules 256a-256n, in one illustrative embodiment, include the structures and functions of treadmill 20. Generally, trainer modules 256a-256n include one or more exercise mechanisms with one or more moveable elements that enable an individual to exercise during and exercise program, whether such exercise program requires anaerobic exercise, aerobic exercise, or a combination thereof. Additionally, trainer modules 256a-256n are configured to enable a trainer, whether a physical therapist, personal trainer, or the like to perform an exercise program substantially simultaneously with or without substantial delay with users exercising through user modules 252a-252n. Furthermore, trainer modules 256a-256n may include hardware and/or software modules and components that enable trainer modules 256a-256n to control the exercise devices incorporated within user module 252a-252n, such as treadmill 12. As such, trainer module 256a-256n may include various exercise devices commonly known by one skilled in the art, and various hardware and/or software modules that enable the trainer to vary each user module 252a-252n, whether individually, collectively, or subsets of the entire group of user modules 252a-252n.

It may be appreciated by one skilled in the art that trainer modules 256a-256n may take various other configurations as known by one skilled in the art, in view of the teaching contained herein. For example, although trainer modules 256a-256n are depicted herein, trainer modules 256a-256n may be substituted for one or more additional user modules 252a-252n. Therefore, system 250 may enable multiple users to interact one with another through network 16, without the capability to control one another. As referenced previously, it may be understood that system 10 may also enable multiple users to interact one with another through network 16, without the capability to control one another.

Optionally communicating with communication module 254 is a third party control module 258. Third party control module 258, in one embodiment, enables some third party such as an additional personal trainer, medical provider, development team, and the like to view the current exercise program, while having the ability to control various operating properties of user modules 252a-252n and/or trainer modules 256a-256n. For example, in a health club setting, third party control module 258 may take the form of a console operated by an individual who is able to control the operating parameters of one or more exercise devices (e.g., during a spinning class), whether operated by a trainer or user, during an exercise program. It may be appreciated by one skilled in the art that various other configurations of third party control module 258 are applicable and known to one skilled in the art, in view of the teachings contained herein.

Figure 10:
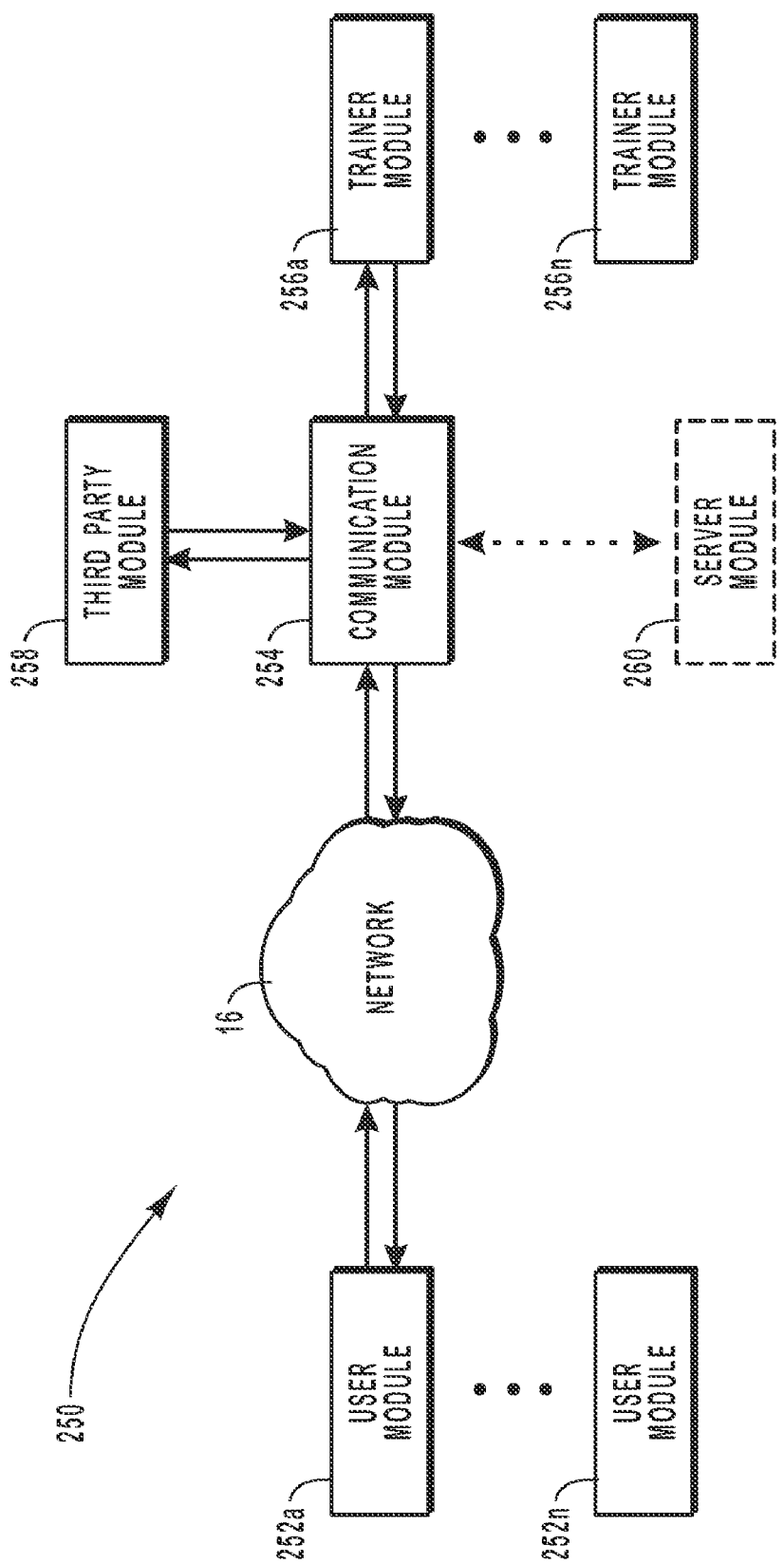
FIG. 10 is a functional block diagram of the exercise system of FIG. 1.

Through the illustrative configuration of control system 250 depicted in FIG. 10, a user performing various exercise activities through user modules 252a-252n may communicate with trainers using trainer modules 256a-256n in real-time communication. Additionally, one user module 252a-252n may communicate with another user module 252a-252n without communicating with one of trainer modules 256a-256n.

Generally, communication module 254 may act as and take the form of a server, with associated hardware and/or software modules to enable communication between the various modules of the illustrated system 250. As such, user modules 252a-252n, trainer modules 256a-256n, and third party control modules 210 may be considered clients of communication module 254. Alternatively, a separate server or a server network, illustrated in dotted lines and referenced by numeral 260 may communicate with communication module 254. In such a case, communication module 254 acts as a client. Generally, user modules 252a-252n, communication module 254, trainer modules 256a-256n, and third party control 210 may communicate one with another, via various communication line connections as discussed herein and known to one skilled in the art in light of the teaching contained herein.

Figure 11:
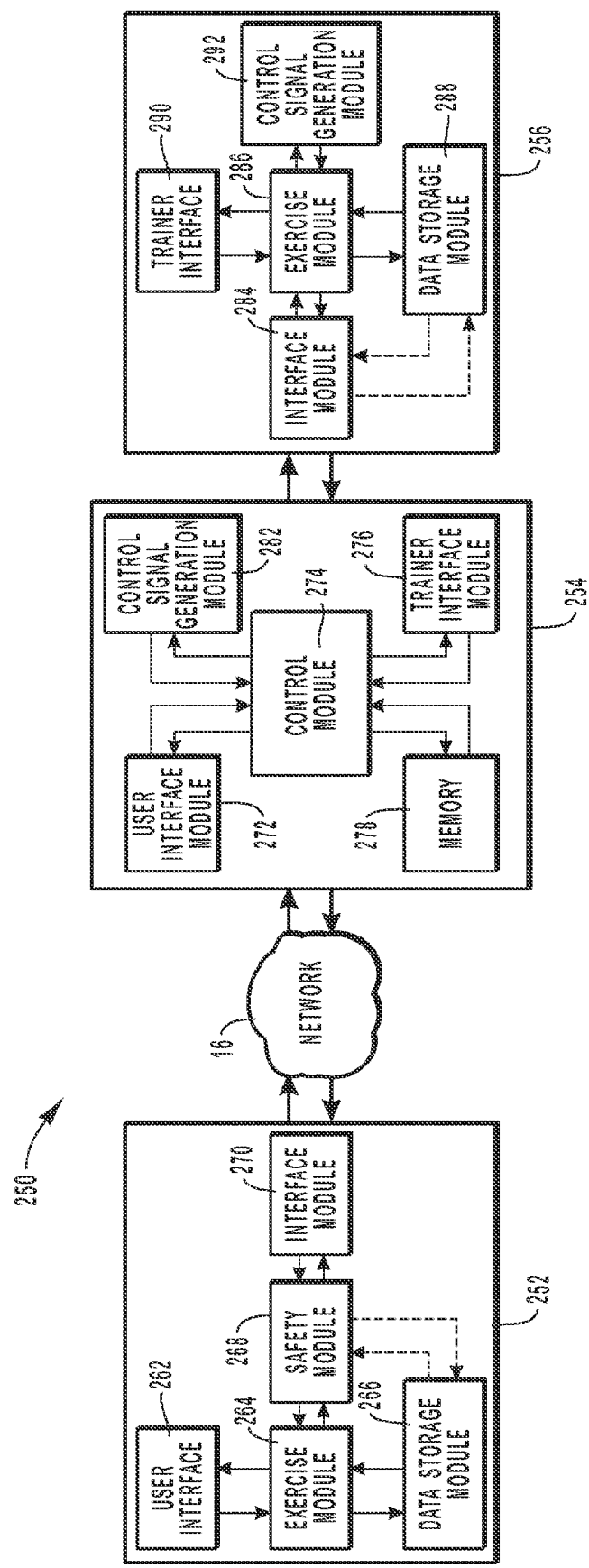
FIG. 11 is a more detailed functional block diagram of the exercise system of FIG. 10.

Reference is now made to FIG. 11, which is a more detailed schematic diagram of system 250. For ease of explanation, FIG. 11 only shows one user module 252 and one trainer module 256; however it may be appreciated by one skilled in the art that a similar discussion may be made for multiple users and trainer modules 252, 256 respectively.

As shown, in one embodiment, user module 252 includes a user interface 262. User interface 262 enables a user utilizing the beneficial characteristics of user module 252 to engage and give commands thereto with respect to various operating parameters of user module 252. For example, user interface 262 may include one or more interface devices as discussed previously, such as one or more audio and video input devices 90, 92 and one or more audio and video output devices 94, 96 as described earlier herein. Therefore, user interface 262 enables the user to visually and/or audibly communicate with the trainer manipulating personal trainer module 256, various other stored programming, or other users. Consequently, user interface 262 may incorporate various structures and functions of treadmill 12, and more specifically control panel 22. Furthermore, user interface 262 may incorporate various portions of translator device 13 and computer 14, such as, but not limited to, monitor 166, keyboard 160, mouse 162, and the like. User interface 262 is one structure capable of performing the function of interface means for gathering a first real-time signal from the user and also means for reproducing the second signal from the trainer.

It may be appreciated by one skilled in the art that user interface 262 and hence the interface means may take various forms or configurations to perform the desired function thereof. For example, user interface 262 and interface means may be a voice activated interface, a touch sensitive interface, an automatic monitoring system, such as a system that monitors heart rate, blood pressure, and the like and various other measurable parameters of user module 252 and a user exercising through user module 252.

User interface 262, in one embodiment, communicates with exercise module 264, such as treadmill 12 or other mechanisms having a movable element. Exercise module 264 includes various hardware and software components that enable an individual to obtain aerobic exercise, anaerobic exercise, combinations thereof, or the like exercise program. For example, in one embodiment exercise module 264 is treadmill 12 with computer 14 and translator device 13. Alternatively, exercise module 264 is treadmill 12 with components of computer 14 and translator device 13 therein.

It may be appreciated that the various modules related to user module 252 may be incorporated within exercise module 264, or more specifically within treadmill 12 or some other device. In another configuration, exercise module 264 includes a movable element, such as belt 42, that allows the user to exercise. In yet another configuration, exercise module 264 may incorporate the structure and functionality associated with user interface 262 therein.

Communicating with exercise module 264 is a data storage module 266. Data storage module 266, in one embodiment is a database of operating parameters for exercise module 264 with respect to one or more exercise programs. As such, data storage module 266 may be a ASIC chip, programmable ROM, CD-ROM, EEPROM, PCMCIA card, compact flash card, flash bios, dynamic memory, magnetic storage disk, optical storage media, or the like. Additionally, data storage module 266 may be a hierarchal, relational, or other typical database, including related database management systems (not shown). Generally, data storage module 266 contains the necessary data and information to operate exercise module 264 in accordance with a selected program by a user operating user module 252 or alternatively to perform the necessary exercise program designated by the operator of training module 256. Furthermore, data storage module 266 may store programming retrieved from communication module 254 in preparation for activation of exercise module 264 upon a request from a user, communication module 254, or trainer module 256. Data storage module 266 may be incorporated within exercise module 264 such as when user interface 262, exercise module 264, and data storage module 266 are part of treadmill 12, whether or not translator device 13 and/or computer 14 is integrally formed therewith.

Communicating with exercise module 264 is a safety module 268. Safety module 268 optionally communicates with storage module 224. Safety module 268 is intermediate between an interface module 270 and exercise module 264 and controls the data transferred through network 16 from communication module 254. As such, safety module 268 tracks the information delivered from communication module 254 and automatically engages a program stored within data storage module 266 upon disengagement of the connection with communication module 254 through interface module 270, thereby delivering one or more safety signals to exercise module 264. Alternatively, safety module 268 may maintain the operating parameters of exercise module 264 at the same level as before disengagement of user module 252 from communication module 254, thereby sending safety signals that maintain the operating parameters of exercise module 264 at the same level as before interruption of the programming. In yet another configuration, safety module 268 sends one or more safety signals that slowly decrease all the operating parameters of exercise module 264 to either a user defined or communication module 254 defined base level or to zero upon disengagement of user module 252 from communication module 254. As such, safety module 268 may include various hardware and/or software components and modules necessary to perform the desired function, such as, but not limited to, a buffer to store programming received from communication module 254. Therefore, safety module 268 is one example of a safety mechanism that is capable of manipulating the operating parameters of the exercise mechanism in the event that a packetized second control signal is interrupted. As such, safety mechanism may generate one or more safety signals to operate the exercise mechanism, as discussed herein. Safety module 268 is another example of communicating mechanism of the present invention.

Interface module 270, connected to safety module 268, manipulates the information and data transceived through user interface 262, whether such data is to be delivered to exercise module 264 or for delivery to communication module 254 through network 16. As such, interface module 228 performs various operations on the data, such as, but not limited to, encrypting data, decrypting data, buffering data, packetizing data, depacketizing data, and the like. Interface module 270 is one example of a communicating mechanism, communicating with the interface, the communicating mechanism enabling real-time transmission of the first signal to a trainer, the communicating mechanism receiving a packetized second real-time signal. In addition, interface module 270 is an example of a structure capable of performing the function of a communicating means, communicating with the interface means, for receiving a packetized second signal, and optionally, for enabling transmission of the first signal.

It may be appreciated by one skilled in the art that there are various other configurations of interface module 270 and hence communicating means. For example, interface module 270 may facilitate communication of data between one or more users rather than between user module 252 and trainer module 256.

Generally, each of the modules referenced as being included within user module 252 may be integrally formed with treadmill 12 or exercise module 264. Those modules may, alternatively, be added to or installed within an existing exercise device to allow the same to communicate with communication module 254. Therefore, the particular functions of each of the modules referenced within user module 252 may vary depending on the particular characteristics and properties of the exercise device. Similarly, user module 252 may include various other modules that may be appropriate, as understood and may be identified by one skilled in the art.

User interface 262, safety module 268, data storage module 266, and/or interface module 270 are examples of a controller, responsive to the packetized second real-time signal, configured to control the operating parameters of the exercise mechanism (or exercise module) in real-time. Additionally, such a controller is a structure capable of performing the function of control means, communicating with the exercise mechanism (or exercise module), for receiving one or more packetized control signals from the communication system (or communication module) indicative of the selected exercise program and for changing one or more operating parameters of the exercise mechanism (or exercise module) based upon the selected exercise program and the one or more packetized control signals. It may be appreciated by one skilled in the art that the control means may have various other configurations.

Communicating with user module 252 via network 16 is communication module 254. As shown, communication module 254 includes a communication user interface module 272 that transceives data, such as audio, video, and control signals between user module 252 and communication module 254. Communication user interface module 272 may have various forms, such as, but not limited to, those described herein with respect to interface 190. Additionally, communication user interface module 272 may include various hardware and/or software modules and components to encrypt data, decrypt data, buffer data, packetize data, and depacketize data, and the like.

Communicating with communication user interface module 272 is control module 274 that may have a similar configuration and function to control processor 192 in FIG. 8.

Control module 274 performs many of the functions recited with respect to control processor 192, in that control module 274: (1) manipulates the data to be transmitted to user module 252, (2) enables the user to select one of a plurality of different programs, whether such programs are stored or live, such as those stored in memory 278, (3) requests the creation of control signals by control signal generation module 282 which may be synchronized with the exercise programs, (4) transmits data between one or more user modules 252, between a one or more user modules 252 and trainer modules 256 via communication trainer interface module 276, between one or more user modules 252 and/or third party module 258, and the like. Additionally, control module 274 may access data that is stored in one or more memory modules: memory 194 and external memory 196.

Furthermore, control module 274, may automatically disconnect data communication between user module 252 and communication module 254 when the movable element of exercise module 264 is stopped by the user. For example, in a gym type setting, once an individual connects to communication module 254, and/or communication system 18, control module 274 provides access to communication module 254 with associated programming. As a user exercises, control module 274 tracks the active status of the movable element of exercise module 264 to determine whether the user is continually exercising. When the user activates, through user interface 262, stop/pause button 78 (FIG. 6), control module 274 disconnects the user from communication module 254. Furthermore, control module 274 clears the temporary data file stored in storage module 224 of user module 252 and may also clear the temporary data files stored in communication module 254 that relate to the particular user. In this way, control module 274 prepares user module 252 and communication module 254 for use by subsequent users. Although the above discussion is directed to control module 274, it may be appreciated by one skilled in the art that control processor 192 may perform the same function with control processor's hardware and/or software modules and components.

Control signal generation module 282 may have a similar configuration to that of control signal generator 200 (FIG. 8), so long as control signal generation module 282 is capable of creating one or more control signals that may be synchronized with the audio and video signals retrieved from memory 194, 196 or received through communication trainer interface 276 from trainer module 256.

Trainer module 256 has substantially the same configuration as that of user module 252. Therefore, trainer module 256 includes an interface module 284 for transceiving data between trainer module 256 and communication module 254. Communicating with interface module 284 is an exercise module 286 and optionally a data storage module 288. Furthermore, trainer module 256 includes a trainer interface 290 that enables a trainer to input various exercise parameters to change the operating parameters of user module 252. Trainer interface 290, therefore, may include the various input devices recited previously with respect to user module 252 and/or treadmill 12.

Trainer module 256 optionally includes a control signal generation module 292. Control signal generation module 292 enables trainer module 256 to generate control signals that are synchronized with the audio and/or video signals that are transmitted from trainer module 256 to user module 252. Control signal generation module 292, therefore, is substantially the same as control signal generation module 282.

The synchronization of the audio and/or video signals with the control signals may be achieved in a variety of different manners. For example, in one embodiment of such synchronization, the audio and/or video signals indicate that the treadmill speed will move from 1 mile per hour to 5 miles per hour. The control signal may not automatically move the speed to 5 miles per hour, but may instead ramp gradually from 1 mile per hour to 5 miles per hour. Optionally, the control signal and video/audio signals are synchronized such that a message increasing to a given speed is instantaneously matched by the exercise device.

Following hereinafter is a discussion of the various optional modules that may be incorporated within communication module 254, in addition to those discussed earlier. It may be appreciated by one skilled in the art, that communication module 254 includes the typical user interfaces and communication interfaces for enabling user module 252a-252n to communicate with training module 256a-256n and optionally another user module 252a-252n. Generally, therefore, communication module 254 includes various other functional modules. Additionally, the following discussion describes various functions of communication system 18 and its interaction with a user at treadmill 12, computer 14, translator 13, third party 21, and/or a trainer at treadmill 20

Figure 12:
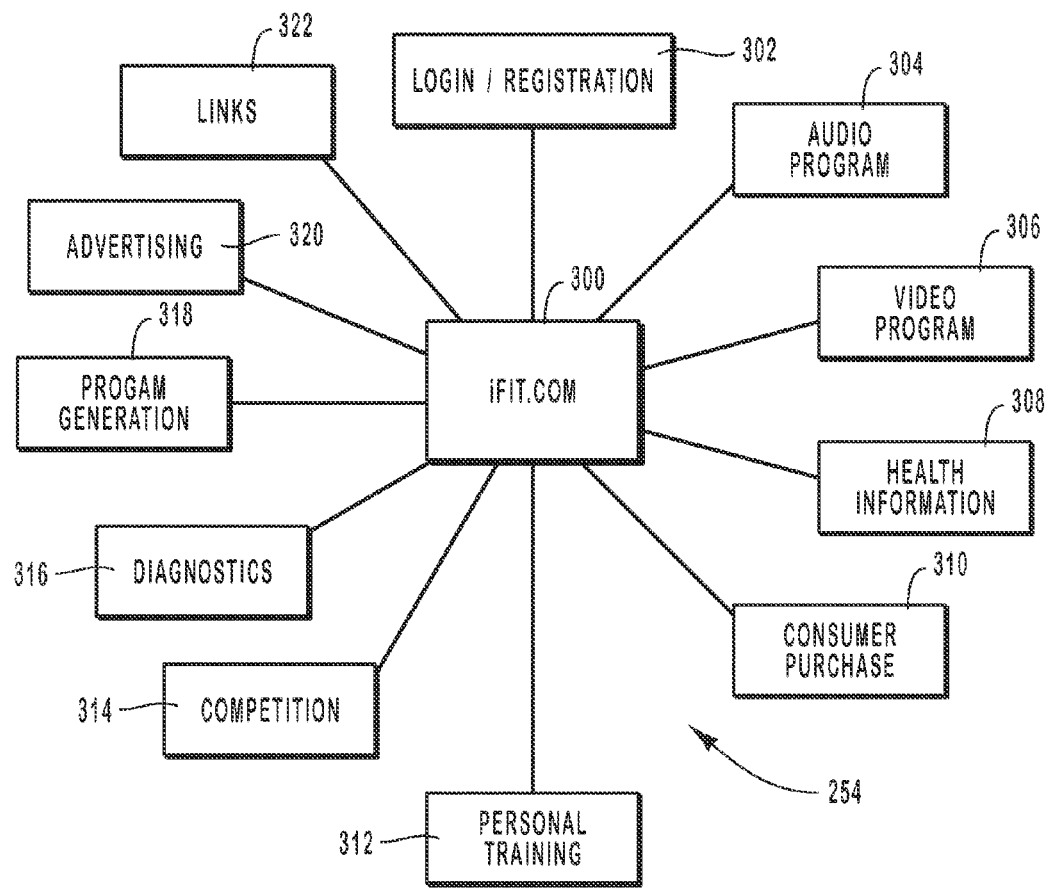
FIG. 12 is a functional block diagram of the illustrative modules of the communication module.

As shown in FIG. 12, communication module 254 (FIG. 11) includes, in one embodiment, an iFit.com website 300 that acts as both an interface with the user, while also controlling the operation of user module 252a-252n and/or trainer module 256a-256n. As such, iFit.com website 300 is in communication with a number of various other modules forming one embodiment of communication module 254. Each module depicted may represent functionality included within communication module 254, while representing structural hardware and/or software modules that may either be incorporated within the hardware and software modules of iFit.com website 300, or alternatively, accessible by the hardware and software modules forming iFit.com website 300.

Generally, the iFit.com website 300 is hosted on one or more computers, whether a general-purpose or special-purpose computer, that may have the form of computer 14, or any variation thereof known by one skilled in the art in view of the teaching contained herein. As such, the hardware and software modules forming iFit.com website 300 may include those listed herein with reference to computer 14. As depicted in the illustrative configuration of FIG. 12, iFit.com website 300 may include login-registration module 302, audio program module 304, video program module 306, health information module 308, consumer purchase module 310, personal training module 312, competition module 314, diagnostic module 318, program generation module 318, advertising module 320, and links module 322.

According to one aspect of the present invention, communication module 254 includes a login-registration module 302 that is accessible via iFit.com website 300. Login-registration module 302 is configured to obtain the necessary registration and login information from a user wishing to use communication module 254 and the various audio/video and literary information contained therein, with their exercise device.

Figure 13:
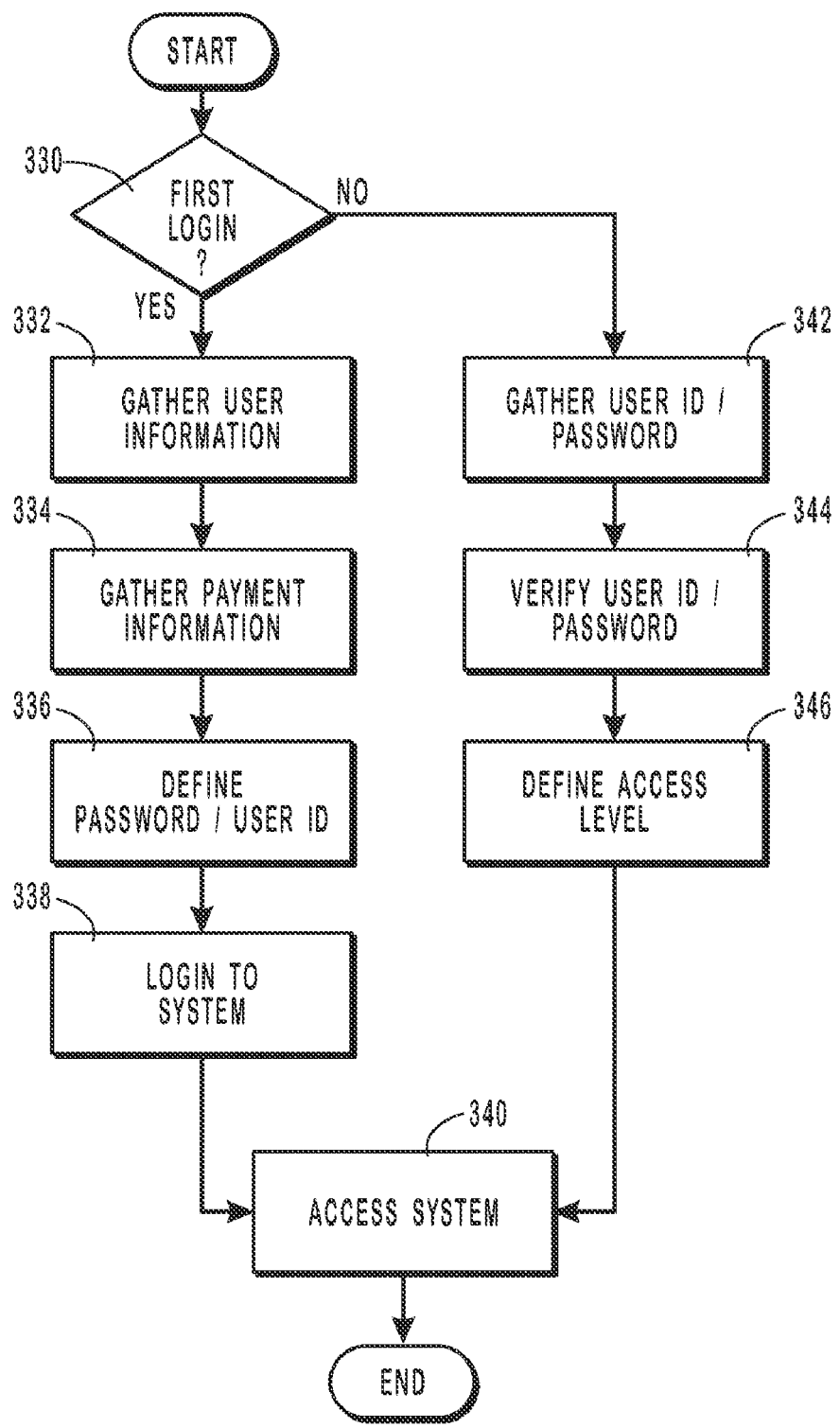
FIG. 13 is a flow diagram illustrative of the process of gathering information through the login/registration module of FIG. 12.

Referring now to FIG. 13, a flow diagram illustrating the operation of login-registration module 302 is depicted. Initially, login-registration module 302 identifies whether the user has logged into the communication module 254 before, as represented by decision block 330. In the event that the user is accessing or "logging in" to iFit.com website 300 for the first time, login-registration module 302 gathers the user information, as shown by block 332. Specifically, login-registration module 302 may gather the user's name, age, sex, type of exercise equipment being used, and various other data unique to the user. Additionally, login-registration module 302 may present the user with multiple questions to obtain statistical information regarding the user's background, education, work experience, income, hobbies, and other related information to aid operators of communication module 254 and system 250 in providing greater instructional information to the user. Furthermore, such statistical information may also be used in targeting specific advertisement to the individual during an exercise program.

As information is gathered from the user, payment information, such as credit card numbers, accounts, and the like may further be obtained from the user. Alternatively, as depicted in FIG. 12, the step of obtaining payment information may follow the gathering of the user information, as shown by block 334. Once all the necessary information is gathered, login-registration module 302 assists the user in defining a login user identification number (user ID) and password that are unique to the particular user, as depicted by block 336. Upon defining the user password and user ID communication module 254 stores the information within a memory of communication module 254 and optionally user module 252. The user is subsequently asked to login to communication module 254.

Following the logging in procedure, the user is given access, as depicted by block 340, to communication module 254 to the specific level that they are allowed, based upon their responses to the various questions asked during the login procedure. For example, if a user defines the exercise device as a treadmill located at home, the user may be limited to only the treadmill related web pages of iFit.com website 300. Similarly, if a user does not define any account information the user may be limited to only the free web pages and information available thereon, while being restricted to access the fee-based web pages, such as to purchase exercise profiles, exercise equipment, and the like.

Referring again to decision block 330, if a user accesses communication module 254 for a second or any other subsequent times, decision block 330 is in the negative, and login-registration module 302 gathers the user ID and password from the user, as depicted by block 342. Upon gathering the user ID and password, login-registration module 302 verifies the user ID and password with the stored user ID and password, as represented by block 344. Subsequently, login-registration module 302 either rejects access to communication module 254 or alternatively allows access thereto with the specific level of access, as shown by blocks 346 and 340.

It may be appreciated by one skilled in the art, that various other functionality and structures might form login module 302. For example, login-registration module 302 may incorporate various processors, micro-controllers, logic circuits, and the like to analyze and store the information input during a login process. In one configuration, login-registration module 302 may communicate with user module 252 during the login process to verify that the exercise device used by the user is the same as previously indicated by the user during previous logins. In the event that the exercise device differs, whether by type, model or the like, login-registration module 302 may cause communication module 254 to either prompt the user to change the stored login information, thereby varying the access to the various programs, or automatically change the login information and associated access in light of the changed exercise device.

In another configuration, login-registration module 302 may be a separate hardware and/or software module or component that is located distantly from the hardware and/or software components or modules of communication module 254. In still other configurations, login-registration module 302 may be further adapted to store information regarding the use of exercise equipment. For example, login-registration module 302 or some other module of communication module 254 may track the amount of time that a user spends exercising on a particular type of exercise device, thereby determining a user's exercising preferences.

Furthermore, login-registration module 302 may track the particular locations where the user trains to identify a user profile of the user's exercise activities throughout the United States of America or the World. Such information may then be used to provide the user with specific information related to those locations where the user exercises most. For example, the user may receive targeted advertising to exercise and non-exercise related businesses or services within the city or state of the place where the individual commonly visits or exercises.

Referring back to FIG. 12 communication module 254 includes an audio program module 304. Generally, audio program module 304 is configured to provide the user with multiple selections of audio programs that are available for particular types of exercise devices. Additionally, audio program module 304 allows the user to purchase copies of the audio programs that may be performed on line.

Figure 14:
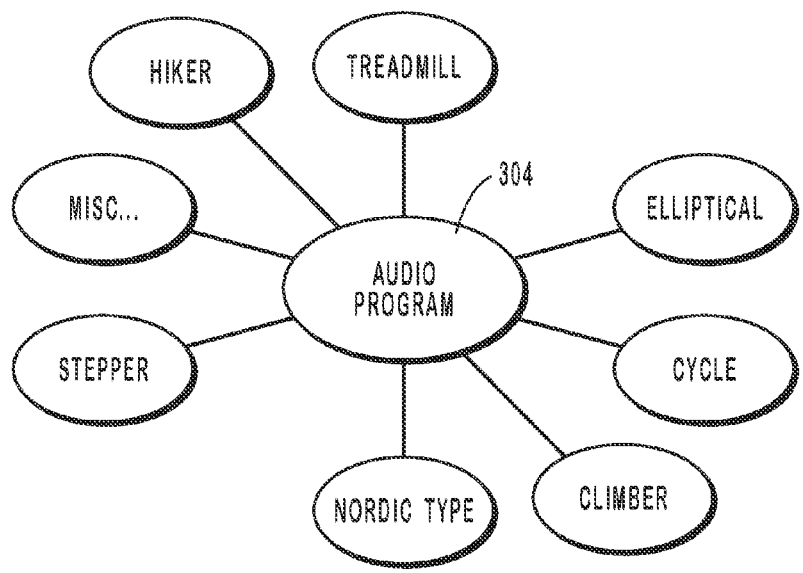
FIG. 14 is a functional block diagram of illustrative modules of the audio program module of FIG. 12.
Figure 15:
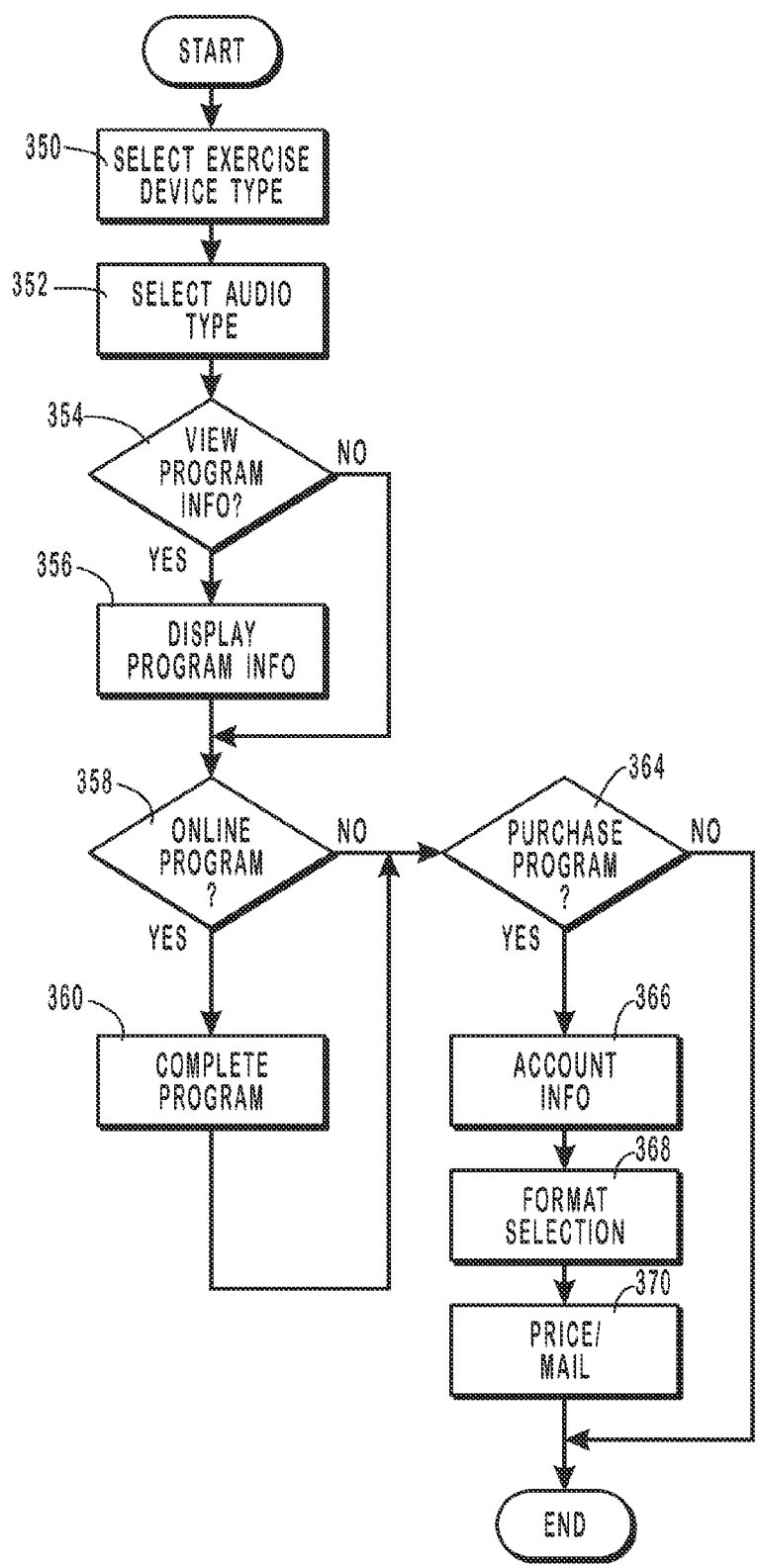
FIG. 15 a flow diagram illustrative of the process of selecting an audio program for a particular exercise device selected from those illustrated in FIG. 14.

As depicted in FIG. 14, audio program module 304 allows the user to select from various types of exercise devices with associated audio programs. As illustrated, audio programs may have separate information for treadmills, ellipticals, cycles, steppers, hikers, climbers, Nordic type exercise devices, and various other types of exercise devices known by one skilled in the art. As such, a user may manually select the particular exercise device to be used. Alternatively, audio program module 304 may dynamically select the particular exercise device and the various audio programs applicable to the user's exercise device by analyzing the user information gathered by login-registration module 302. No matter the manner by which the particular exercise device is selected, FIG. 15 depicts an illustrative flow diagram that depicts possible user selections and data flow related to accessing the one or more audio programs available through communication system 18, and more specifically iFit.com website 300.

As shown, upon selecting a particular exercise device (whether manually or dynamically as discussed above), as depicted by block 350, the user is allowed to select the type of music to be played during the program session, as depicted by block 352. Once the user has selected the particular music type, the user is given the option to view the program information to determine if the difficulty level is too great, as depicted by decision block 354. For example, if the individual wishes to view the exercise program profile, communication module 254 packetizes an audio and/or graphical representation of the exercise program selected (i.e., the maximum speed, maximum incline, time to perform the exercise program, amount of time at each maximum speed and incline, and various other operating parameters known to one skilled in the art) and transmits the data to either the integrally formed video output device 92 (FIGS. 1 and 6) mounted on treadmill 12, or alternatively, to monitor 166 (FIG. 7) associated with computer 14 for review by the user, as depicted by block 356.

Alternatively, the user may decide not to view the user profile, such that the response to decision block 354 is in the negative. Whether or not the user views the exercise profile, the user may select to begin the online exercise program, as depicted by decision block 358. If the user selects in the affirmative, communication module 254 delivers the audio signals, with control signals, to user module 252 in accordance with the selection. Consequently, communication module 254 may download the entire audio program to user module 252, or alternatively "stream" the audio signals thereto by a manner known by one skilled in the art. Upon completion of the program, as depicted by block 360, the user is given the opportunity to purchase their own copy of the audio program just performed, as represented by decision block 364. In the event they decline to purchase the program session, the particular audio program session is completed and the user is optionally returned to the homepage of iFit.com website 300.

Referring again to decision block 358, if the user selects not to perform the online program, the user may optionally select to purchase the program, as depicted by decision block 364. If this selection is in the negative, the user is returned to the homepage of iFit.com website 300. Otherwise, if the user wishes to purchase the program, audio program module 302 gathers account information, as depicted by block 366 and media format, such as CD, tape, MP3 file, or the like, as depicted by block 368. Furthermore, audio program module 304, through video output device 90 or monitor 166 displays the pricing guides for various types of media and/or associated mailing costs, as depicted by block 370. Alternatively, audio program module 304 may interface with an accounting module that performs the function of storing and collecting account information and purchase information from any of the various modules associated with communication module 254. As such, communication module 254 may have a centralized accounting module that is accessible by one or more of the various modules forming communication module 254. Furthermore, in another alternate configuration, audio program module 304 may communicate with login-registration module 304 and obtain account information therefrom.

Referring again to FIG. 12, communication module 254 further includes video program module 306. Video program module 306 uses a similar flow of information and related functional operations as audio program module 302; however, video program module 306 merely gives video options to the user, whether such video options include or exclude audio programs transposed or incorporated therein. Therefore, instead of selecting a music type, video program module 306 enables a user to select a video program session and receive real-time or streamed video and/or audio signals. Similarly, in the event the user wishes to purchase the video program, video program module 306 enables the user to select a particular type of video format such as CD ROM, DVD, video tape, MP3 file, and the like.

According to another aspect of the present invention, communication module 254 includes a health information module 308. Health information module 308, in one embodiment, includes a searchable database of information related to health issues for those exercising and/or those who wish to begin to exercise using communication module 254. As such, in one configuration, health information module 308 is a distantly located database, such as a relational, hierarchal, or some other database that is accessible by the iFit.com website 300. Alternatively, health information module 308 may be incorporated within the hardware and/or software components and modules hosting iFit.com website 300.

Communication module 254 may optionally include a consumer purchase module 310. Consumer purchase module 310 is configured to enable a user to purchase exercise equipment, materials such as books and instructional materials, nutritional supplements, and the like online. Consumer purchase module 310 may, therefore, link directly to one or more affiliates of communication module 254. Alternatively, consumer purchase module 310 may include a database, whether relational, hierarchal, or the like that has stored specifications, pricing guides, illustrative images of exercise devices and products, and the like, that a user may search through to find the necessary or desired exercise equipment. Additionally, consumer purchase module 310 may include the necessary hardware and/or software modules to gather and store billing and purchase information from the user or alternatively, consumer purchase module 310 may communicate with a centralized accounting module that performs the necessary functions typically known by one skilled in the art related to accounting, billing, purchasing, sales, and the like activities.

According to another aspect of the present invention, communication module 254 includes a personal training module 312. Personal training module 312 enables a user to interact with a personal trainer on a live-on-live exercise session whether in a one on one session or in a group setting. Additionally, personal trainer module 312 enables the user to ask questions and receive communications from one or more personal trainers related to exercise advice, techniques, and programs, whether or not in real-time.

Figure 16:
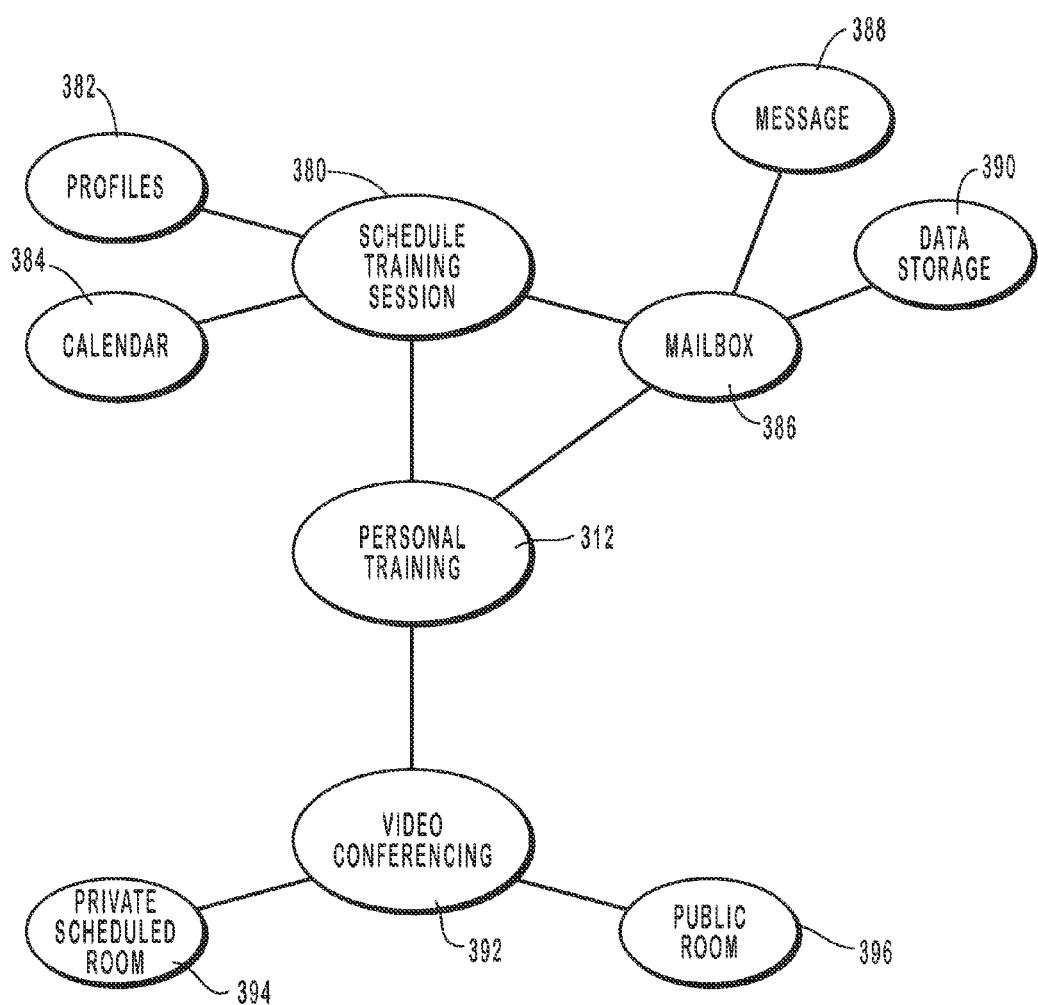
FIG. 16 a functional block diagram of the illustrative modules and functions of the personal training module of FIG. 12.

Referring now to FIG. 16, a schematic representation of the various illustrative functional modules of personal training module 312 are illustrated. As shown, personal training module 312 includes a scheduling module 380 that enables various individuals to schedule times to talk to and optionally perform a live workout program. Scheduling module 380 enables the user to access a profile module 382 that contains one or more trainer profiles. In this way, personal training module 312 enables a user to review the profiles of the various trainers to select the particular trainer that best suits the user's needs and/or time requirements. Profile module 382 may, therefore, include a database, whether relational, hierarchical, or the like, or some other data storage hardware and/or software that is capable of storing data in an accessible form.

Scheduling module 380, in one embodiment, communicates with a calendaring module 384 that lists the days of the month and the particular times available for one-on-one exercise programs with each trainer. Additionally, calendaring module 384 may list the times of group sessions and enable a user to select a particular session time reference within calendaring module 384 for the user to exercise with a personal trainer.

As shown, scheduling module 380 may communicate with a mailbox module 386 that includes multiple mailboxes, one for each user and trainer. Each mailbox may receive email from trainers and other users of communication module 254, or alternatively, only trainers or communication module 254 may deliver a message 388 to each user, such as electronic mail. Generally, each mailbox is configured to receive messages from the trainers regarding scheduled one-on-one exercise sessions or group sessions. Additionally, communication module 254 or iFit.com website 300 may deliver notifications of upcoming special group exercise sessions, or other information related to the user and/or exercising. Each user and/or trainer may save unique exercise programs created by the user and/or the trainer within data storage 390 accessible by mailbox module 386. Optionally, data storage 390 may correspond to memory 278 (FIG. 11) or other external memory that is accessible to mailbox module 386.

Communicating with personal training module 312 is a video conferencing module 392. Video conferencing module 392 provides the functional hardware and/or software to allow a user to videoconference with a personal trainer. For example, video conferencing module 392 may include various hardware and/or software modules that: (1) assist with data transmission of audio and/or video signals between user module 252a-252n and trainer module 256a-256n; (2) assist with image and voice capturing; (3) packetizing or depacketizing data, and the like, such as those discussed with respect to system 10, or otherwise known to those skilled in the art in light of the teaching contained herein. Additionally, video conferencing module 392 allows the user to videoconference with the personal trainer in either a private room, as represented by numeral 394 or in a public room, as represented by numeral 396. In either case, (i.e., in the private or public room) the user may exercise with the personal trainer in a one-on-one or group setting.

It may be appreciated by one skilled in the art, that the functionality described herein with respect to personal training module 312 may be varied and is only illustrative of one possible embodiment thereof. Other functionality and associated structures such as hardware and/or software modules may be included within personal trainer module 312. Furthermore, various other linkages may occur between the various functional modules of personal training module 312. For example, in one alternate embodiment, calendaring module 384 is linked with private room 394 such that upon scheduling a one-on-one exercise program, a private room is automatically scheduled for the user. Additionally, calendaring module 384 may automatically send a message to the user's mailbox, thereby providing the user with information regarding the particular private room scheduled and a reminder of the schedule time.

According to another aspect of the present invention, as illustrated in FIG. 12, iFit.com website 300 includes a competition module 314. Competition module 314 enables one or more individuals to engage in competitive exercise programming with one another or alternatively with the communication module 254 hosting iFit.com website 300. Such competitive exercise programming motivates the users to exercise on a more regular basis while also setting goals for the individual to reach. Competition module 314, therefore, provides various benefits to those seeking to exercise on a regular basis.

Referring now to FIGS. 17A-17D, a flow diagram representing one illustrative operation of competition module 314 is depicted. As shown, a user selects the particular race types that they wish to engage in, as depicted by block 400. Three types of races are depicted; race around the world 402, race against the computer 404, and personalized race 406; however various other race types are applicable and known to one skilled in the art, in view of the teaching contained herein.

One particular race type is a race around the world. In the race around the world type race, an individual races against various other individuals to determine who will run around the world in the shortest time. Communication module 254 tracks the exercising activities of competing users of user modules 252a-252b and computes the distance traveled per exercise session and per user. A running total of the distance traveled is maintained and updated. Each competitor may compare the total distance traveled against other competitors to see who runs a number of miles equivalent to running around the world in the shortest time.

With reference to FIG. 17A, when the race around the world race type is selected, competition module 314 retrieves the stored statistical information of the user, as depicted by block 410. The statistical information may include, but is not limited to, distance traveled by the user, average speed of the user, and the like. Once competition module 314 selects the stored statistical information, such information may be compared against other competitors in the race, as depicted by block 412. Competition module 314 may deliver comparison data to communication module 254. In turn, communication module 254 may deliver a graphical representation of the user's exercise distance, times, speed, and other information compared against other competitors to the user via user module 252a-252n. A user module 252a-252n or a user operating treadmill 12, for example, may view their distance and times with respect to other competing users of user modules 252a-252n, thereby being motivated to exercise more. Once such information is depicted, the user may modify their existing exercise programs to either increase or decrease exercise parameters of the programs. For example, if the user sees that they have not run as many miles as other competitors, they may increase the distance to be run in the future. Once the user is ready, the user may begin or continue the race, as represented by block 414. As the user exercises communication module 254 records new statistical information for the user, such as speed, distance traveled, calories used, and the like.

It may be appreciated by one skilled in the art that various other configurations of the race around the world type race are applicable and known to one skilled in the art. For example, in another configuration of the race around the world type race, a user may select a particular time period, say from January 1 to February 1, and race against others to see who travels the furthest distance within the given time period. Again, communication module 254 tracks the distance traveled of each competitor and may provide graphical representations of the position of one competitor against the other competitors. In still yet another configuration, the race around the world may include racing over various types of terrain ranging from deserts, mountains, and the like. As such, each competitor follows a similar overall exercise profile and communication module 254 tracks the time that a user takes to complete the race, for example, when a user slows down the treadmill based upon the terrain traversed.

Referring again to FIG. 17A, the user may optionally select to race against the computer, as referenced by block 404. As the name of the race type suggests, this option enables the user to select a particular type of race and a particular skill level of the computer against which to race. As shown in FIG. 17C, a user selects the difficulty level for the particular race, as represented by block 416, such as in the case of a treadmill, the speed, incline, distance, and the like. This may also enable the user to select a particular skill level of the computer, such as a beginner runner, intermediate runner, or advanced runner. Additionally, the user may select various other options, as represented by block 418, such as a head start for the computer or the user, scaling of the particular difficulty level, and the like. Upon completing the selections, the user may race against the computer, as represented by block 420.

With reference to FIG. 17A, another type of race is a personalized race, as depicted by block 406. In the personalized race, two or more individuals schedule a live on live session, such as in a private room of personal training module 312 where they may race one against the other, while viewing graphical representations of the distance, time, and speed of the other competitors. Alternatively, two or more individuals may schedule a race where the start time is adjusted based upon the particular location of the competitors.

Figure 17D:
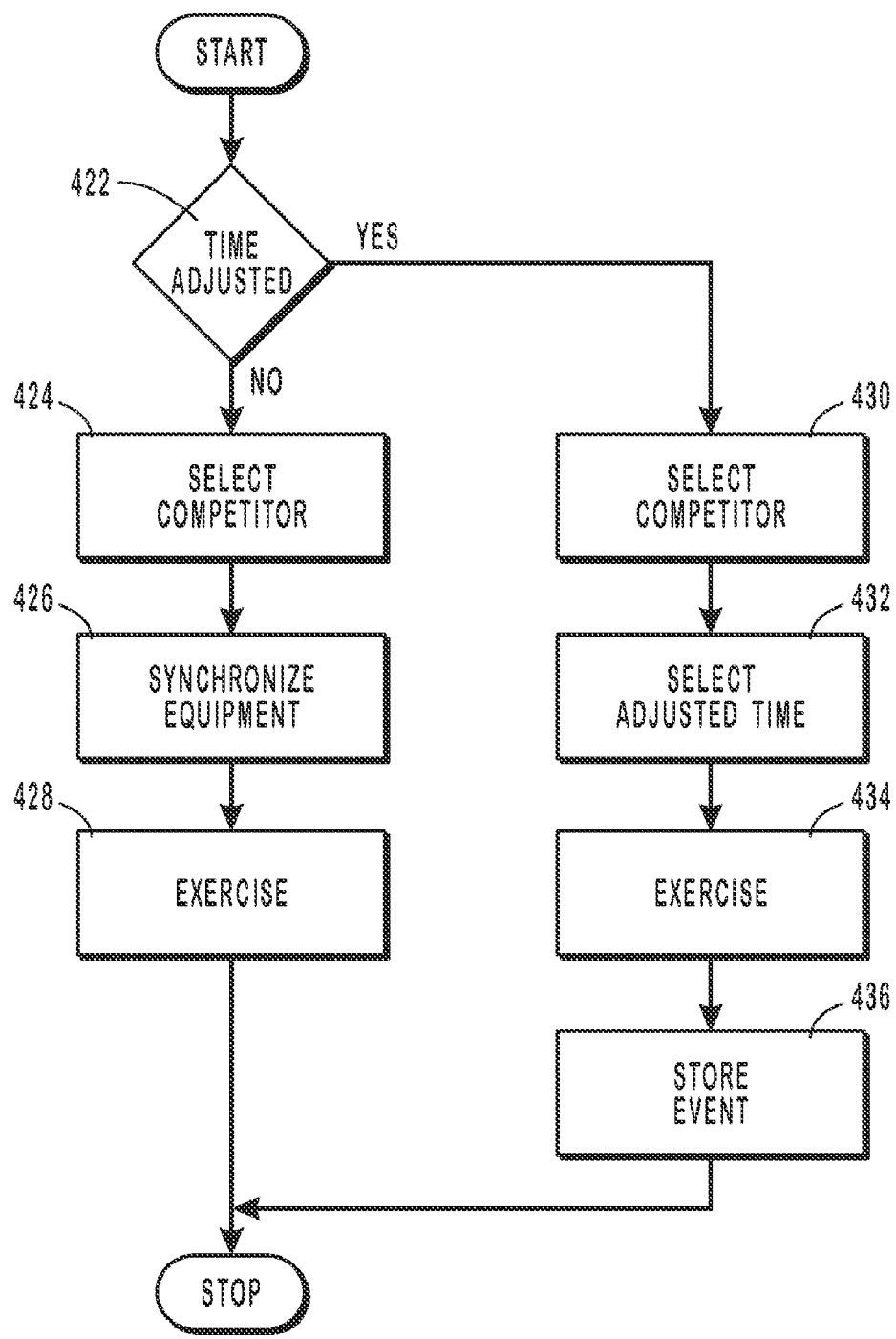

As shown in FIG. 17D, a user may select a time-adjusted race, as depicted by decision block 422. If the user rejects time adjustment, then the user will race against one or more competitors in a live-on-live competition. The user selects one or more competitors, as referenced by block 424. Following the selection, each competitor enters a private room to begin the race and to synchronize each competitor's exercise device with communication module 254 and each other, as depicted by block 426. Alternatively, each competitor may merely enter the private room that has been scheduled for the race, thereby automatically selecting each competitor for the race, while synchronizing each competitor's exercise device in block 426 in preparation for beginning the race as depicted by block 428.

Synchronization prepares the communication links between each competitor and generates the displays and data flow therebetween, such as, but not limited to, the audio and video data flows and displays that enable each competitor to view their progress against each other. For example, the display may include a racing track that shows a relative position of each competitor one with another, or a trail that each competitor races along. It may be appreciated that various other data flows and displays are appropriate and known to one skilled in the art in view of the teaching contained herein.

As suggested above, the user may select a time-adjusted race. The time-adjusted race allows two or more competitors to conveniently race against each other. For example, the time-adjusted race allows an individual on the east coast to race against individuals in the Mountain Time zone and the west coast at the same local time, for example 5:00 p.m. The time-adjusted race, therefore, stores the race of one individual, say the individual on the east coast who races at 5:00 p.m. and then rebroadcasts the stored exercise race to those other individuals in various other time zones upon reaching the designated time period, such as 5:00 p.m. Mountain Standard Time, pacific time, and the like.

With reference to FIG. 17D, for ease of explanation, let us assume that three individuals, one on the east coast, one in the Mountain Time zone, and one on the west coast wish to race against each other at 5:00 pm local time. Each competitor accesses communication module 254 and selects each other as competitors, block 430, in a time-adjusted race, as depicted in decision block 422. Each competitor defines the particular time period or adjusted time at which each individual is to race, as depicted by block 432. The selections and adjusted times for each competitor are stored in one or more databases or other storage modules associated with an identification number given to the time-adjusted race or directly to each competitor. Once the information is entered and stored, the competitor on the east coast may perform their race on their own or with the aid of a pace setter generated by the computer at the appointed time, as depicted by block 434. Once the east coast competitor finishes their race, the statistical information and a real-time representation of the race is stored, as represented by block 436. Upon the arrival of the adjusted time for the Mountain Time zone competitor to race, communication module 254 will rebroadcast the particular race performed by the east coast competitor to the Mountain Time zone competitor. Similarly, upon the time for the west coast competitor to race, communication module 254 will rebroadcast the particular race performed by the east coast competitor and optionally the Mountain Time zone competitor to the west coast competitor. It may be appreciated by one skilled in the art that the live on live and time-adjusted races may be performed in a variety of different manners. For example, the number of competitors is not limited to any specific number. Additionally, the time adjustments may allow for competitors throughout the world to race one against another.

It may be appreciated by one skilled in the art that competition module 314 may have various other configurations. For example, the functionality of competition module 314 may be incorporated within user modules 252a-252n. As such, two or more user modules 252a-252n may be in direct communication one with another, without the aid of communication module 254, and the internal modules of user modules 252a-252n enable competition data to be transceived between the user modules 252a-252n.

With reference again to FIG. 12, communication module 254 further includes a diagnostic module 316. Diagnostic module 316 enables the user to perform a diagnostic analysis of their particular exercise device or product in the case of disconnection or changes in the operation of their exercise device or product. Additionally, diagnostic module 316 enables the user to update and change operational parameters of the user's exercise device or product, either through manual activation of diagnostic control 88 (FIG. 6) or automatically through communication module 254. For example, in the event a new software update is available for the particular exercise device's software, communication module 254 may automatically recognize operation of the update and deliver the same to each individual having an exercise device or product that may benefit from updating of the software. Additionally, the diagnostic module 316 may identify problems with the exercise device and subsequently schedule arrival times for maintenance workers to resolve physical problems that are unable to be fixed by remote communication from communication module 254.

Figure 18:
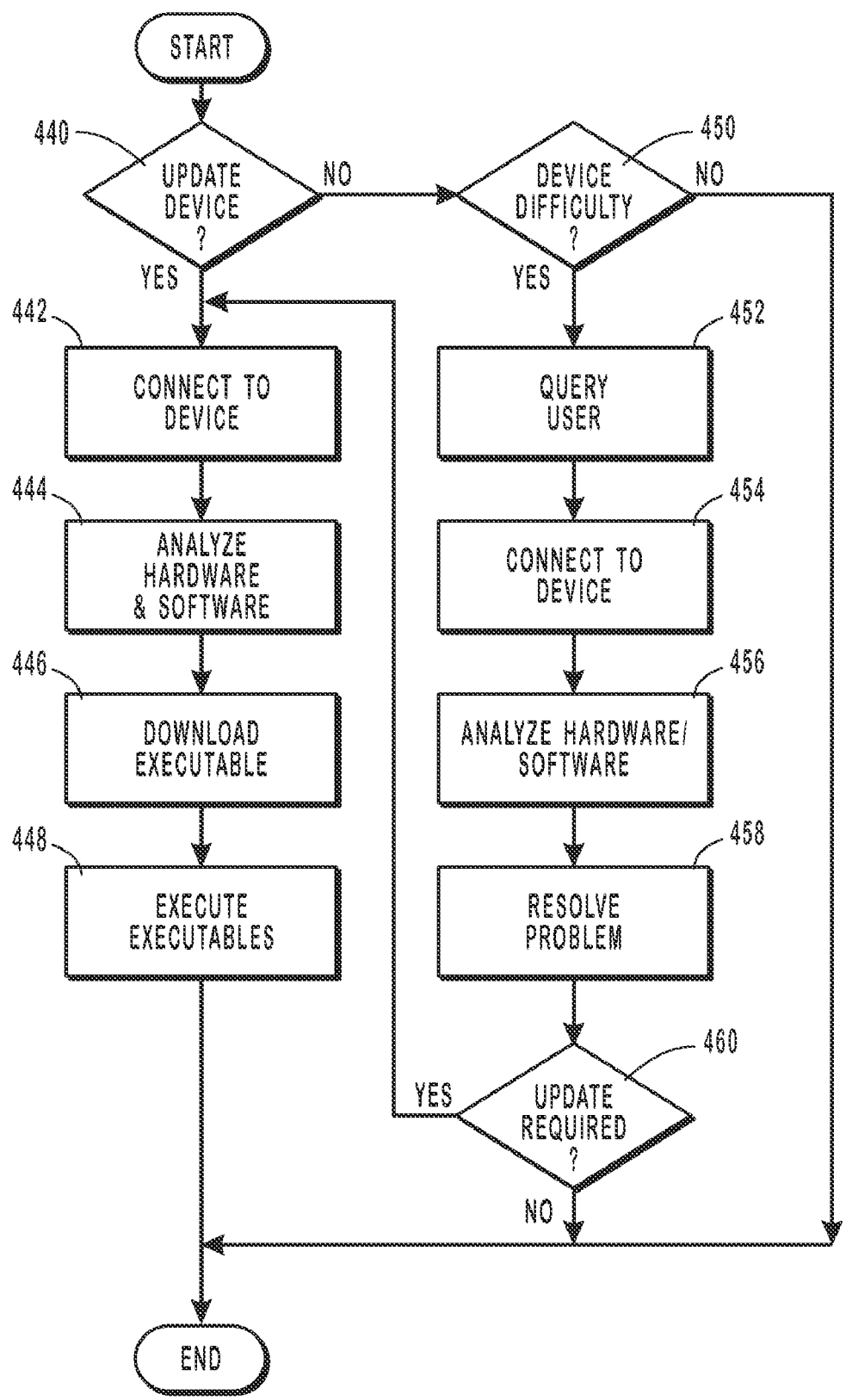
FIG. 18 is a flow diagram representing the process of performing diagnostic on the treadmill of FIG. 2 from a distant location.
Figure 19:
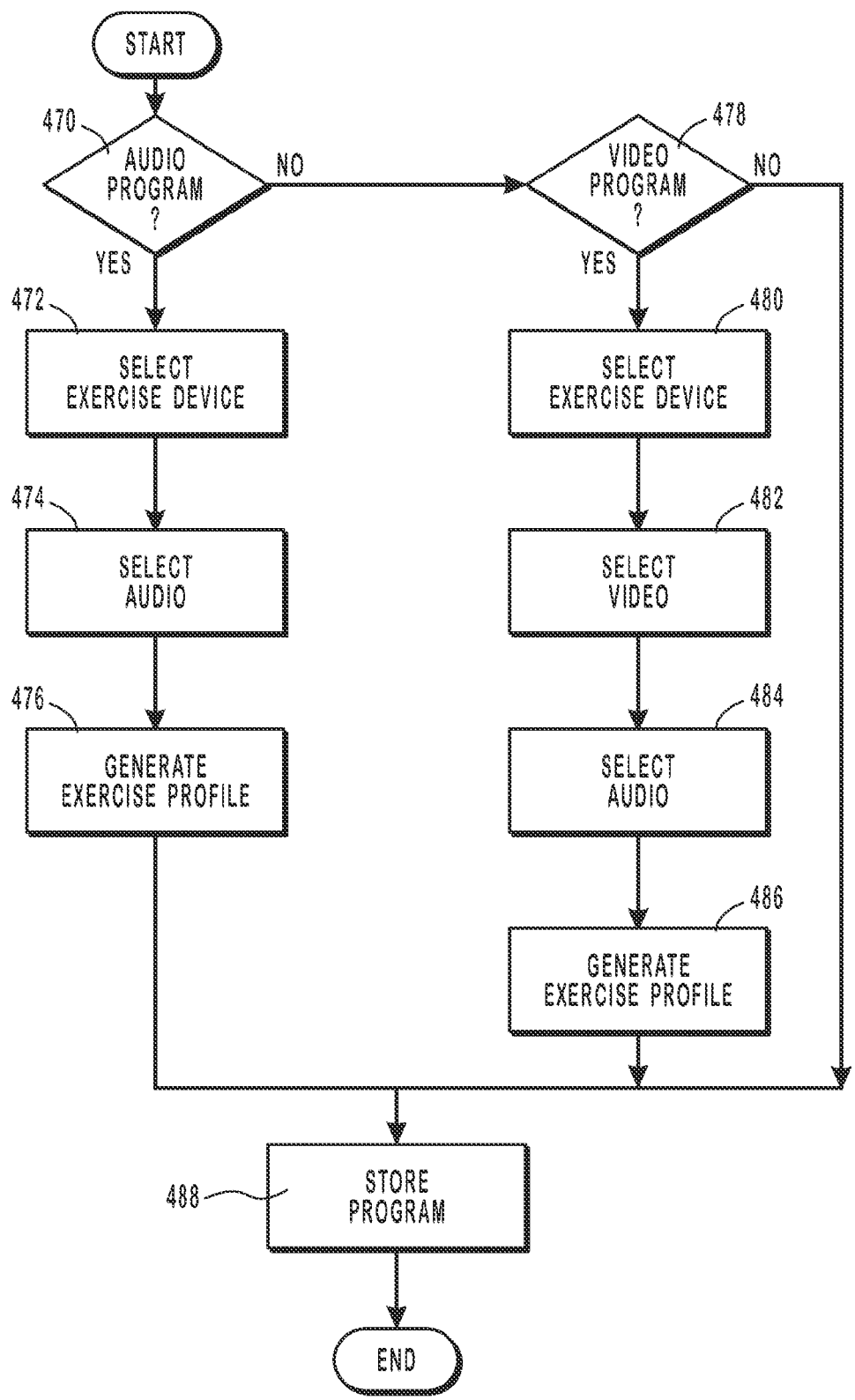
FIG. 19 is a flow diagram representing the actions performed by the user and communication module to create audio and video programs in accordance with the teaching of the present invention.

As such, referring now to FIG. 18, an illustrative flow diagram representing diagnostic module 316 is depicted. As shown, a user is asked to select whether they wish to update their product, as depicted by decision block 440. Alternatively, communication module 254 may automatically recognize that the exercise device or product is to be updated, therefore eliminating block 440 from the flow diagram. In the event that the user wishes to update the exercise device or product, communication module 254, and more specifically diagnostic module 316, connects directly to user module 252a-252n via network 16 (FIGS. 1 and 10), as depicted by block 442. Such connection may be achieved by a variety of manners, as known by one skilled in the art and also discussed herein. Upon connecting to user module 252a-252n or product, diagnostic module 316 verifies that particular hardware and/or software modules are contained therein, as shown by block 444. In the event that software or read/write hardware may be updated, the necessary executable file is either streamed or downloaded to user module 252a-252n, as referenced by block 446. Upon receiving the downloadable file, user module 252a-252n executes the executable file to update the hardware and/or software components therein, as referenced by block 448. Alternatively, such as in system 10 (FIG. 1), the downloadable file may be downloaded to computer 14 which may execute the program and update treadmill 12 remotely.

Referring again to decision block 440, when the user answers in the negative, the user is subsequently queried as to whether they are having difficulty with their exercise device or product, as identified by decision block 450. Upon answering in the affirmative, diagnostic module 316 queries the user, as depicted by block 452, as to the difficulties they are having and what attempts if any, they have made to resolve the problem. Upon gathering the necessary information, diagnostic module 316 connects to the exercise device or other device, as depicted by block 454, and thereafter analyzes the various hardware and software problems to resolve and identify whether it is possible to remotely fix the problem, as depicted by blocks 456 and 458. In the event that the exercise device or product may be remotely corrected, through an update, as depicted by decision block 460, diagnostic module 316 will then perform the steps of updating as previously described in block 442, 444, 446, and 448. Alternatively, if the problem may not be corrected through remote access, diagnostic module 316 may automatically schedule a time for physical maintenance of the device or product. It may be appreciated by one skilled in the art, that various other functionality may be performed by diagnostic module 316.

In an alternate configuration, when user module 252 (FIG. 10) is placed in the active status (e.g. turned on) user module 252 may optionally analyze its internal hardware and/or software modules to verify that such modules are operating correctly. In the event that one or more problems occur, diagnostic module 316 answers decision block 440 in the affirmative, thereby automatically obtaining an update from communication module 254 (FIG. 10) or alternatively manually requesting information from the user. Optionally, when a user of user module 252 accesses communication module 254 (FIG. 10), communication module 254 activates diagnostic module 316 (FIG. 12) to analyze user module 252.

Referring again to FIG. 12, according to another aspect of the present invention, communication module 254 enables a user to prepare a personalized audio and/or video exercise program. Communication module 254, therefore, includes program creation module 318. Program creation module 318, referring now to FIG. 19, enables a user to select an audio program session, as depicted by decision block 470 and/or a video program session, as depicted by decision block 478. In the event that only an audio program session is desired, the user initially selects the type of exercise device that the program is to be used, such as, but not limited to, treadmills, cycles, steppers, hikers, climbers, Nordic style devices, ellipticals, and the like, as represented by block 472. Upon selecting the type of device, the user may then select a specific type of music, such as rock, pop, country, jazz, classical, alternative, or the like, that is to be used with the exercise program, as represented by block 474. Once a particular music type is selected, the user may then generate an exercise profile that the exercise device will follow during the exercise program, as depicted by block 476. Generation of the exercise profile may include defining one or more operating parameters of the exercise device, such as the speed and inclination of the tread base for a given period of time. Upon finalizing the exercise program, the user may then store the program, as represented by block 488, such as in their mailbox, on their exercise device, on a computer readable media, or the like.

In the case of a video program, the user again selects the particular type of exercise device to be used in association with the exercise programming, as represented by block 480. Upon selecting the exercise device, the user may select a particular video presentation they desire, as represented by block 482. The video presentation includes any type of motivational programming known to those skilled in the art. For example, and not by way of limitation, the video presentation may include natural scenes, such as mountains, oceans, streams, and the like, exercising individuals, educational programming, abstract images, and the like. It is preferred that each video presentation includes a specific sound track; however, the user may modify a particular audio track that is synchronized with the video presentation or optionally generate a completely new audio track, according to block 484. Once the video program, and optional music program, is selected, the user may subsequently generate an exercise profile, as represented by block 486, in a similar manner to that described above. As with the audio program, the video program may be stored for use at subsequent times, as depicted by block 488.

The presently described invention may be used in a variety of situations to enable individuals who wish to exercise to obtain more beneficial results in a highly motivated setting. With this in mind, following hereinafter is an illustrative embodiment of an environment within which the exercise devices and modules of the presently described invention may be used.

Referring again to FIG. 12, communication module 254 includes an advertising module 320. Advertising module 320 is adapted to retrieve the information obtained by login-registration module 302 and retrieve from memory 194 or external memory 196 (FIG. 8) advertisements that may be appropriate for the user to view in light of the selections made during the login process. In one embodiment, an audio and video advertisement signal is delivered with the audio and video exercise programming to appear on user interface 262 (FIG. 11). For example, a banner may appear on user interface 262 (FIG. 11), and more specifically video display 94 (FIG. 6) for the user. Such advertising may, alternatively, take the form of an additional streaming, real-time audio and video output that is linked to one or more national advertising agencies. In such a case, the banner may optionally appear for a few seconds to present a micro-commercial targeted to the user of user module 252. Upon completing the commercial, the banner may disappear, to subsequently reappear with the same or alternatively different micro commercials at various periods along an exercise program.

Referring again to FIG. 12, communication module 254 includes a links module 322. Links module 322 is configured to provide the user with a list of various additional web sites where educational and exercise information, products, materials, and the like may be viewed and/or purchased.

Figure 20:
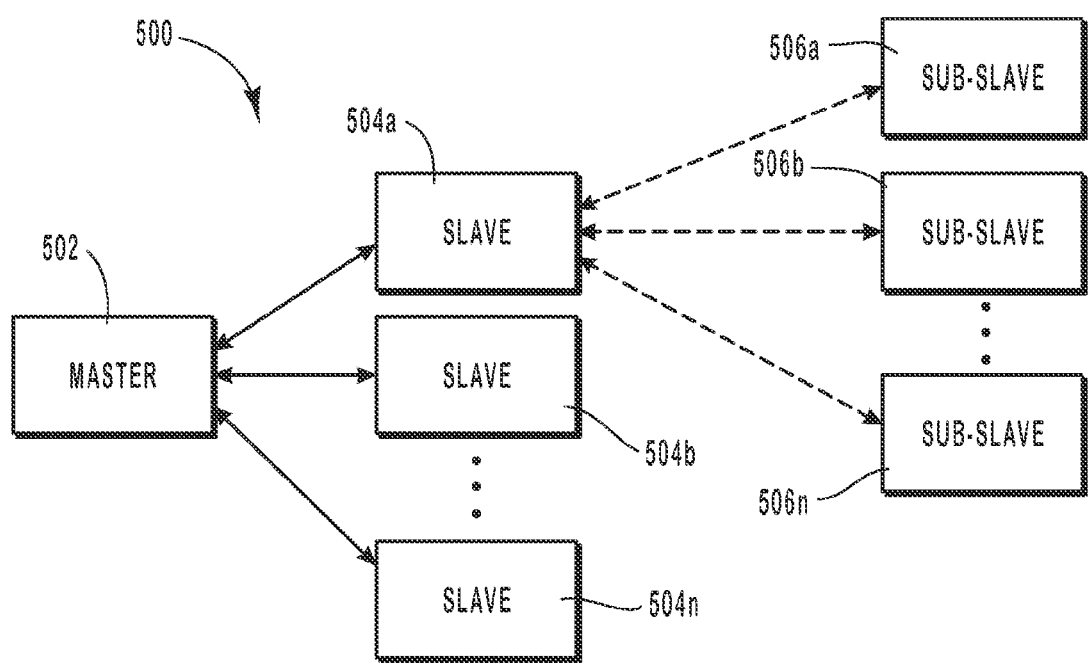
FIG. 20 is a functional block diagram of a master-slave system according to the teaching of the present invention.

With reference now to FIG. 20, a master-slave system 500 is depicted that may or may not use the systems described above to enable communication between the various components of the master-slave system as will be described in detail hereinafter. Master-slave system 500 may use various types of networks, such as the Internet to enable communication between the various portions of master-slave system 500. Master-slave system 500, in this embodiment, includes a master device 502 and one or more slave devices 504a-504n communicating with master device 502. In this embodiment, master device 502 may take the form of a treadmill with a computer integrally formed therein.

Alternatively, master device 502 may be a treadmill with one or more processors, controllers and memory storage devices that allow master device 502 to control one or more slave devices 504a-504n without entirely incorporating a computer therein. Master device 502, therefore, may or may not incorporate the structure and functionality of treadmill 20 (FIG. 1) or other exercise devices, communication module 254 (FIG. 10), and/or trainer modules 256a-256n (FIG. 10).

Generally, master device 502 enables an individual exercising thereupon to control one or more slave devices 504a-504n, in real-time, whether or not master device 502 receives input data from the one or more slave devices 504a-504n. As depicted, master device 502 is directly linked with each of the slave devices 504a-504n via a communication line connection, such as, but not limited to, existing broadcast technology, including short range wireless transmissions, television broadcast over the airwaves, cable or cable modems, satellite, telephone lines, whether analog or digitally based, wireless technology, other high-speed data connections, or any other suitable transmission technology or medium. Master device 502, therefore, includes the appropriate hardware and/or software applicable to enable master device 502 to communicate and control one or more slave devices 504a-504n.

In one case, the internal components of master device 502, alone, are sufficient to enable communication to and control of slave devices 504a-504n. Therefore, master device 502 need not incorporate computer 14 (FIG. 1), translator device 13 (FIG. 1), or hardware and/or software modules of communication system 18, or communication module 254 therein. In another configuration, master device 502 may communicate with slaves 504a-504n via a network and a communication system or module so that master-slave system 500 has a similar configuration to system 250 where one or more trainer modules 256a-256n control the operation of one or more user modules 252*a*-252*n* via network 16, whether or not communication module 254 is used to facilitate such communication and control.

Each slave device 504*a*-504*n* and sub-slave device 506*a*-506*n* linked to master device 502 may take the form of an exercise device, such as treadmill 12, translator device 13, and/or computer 14 of FIG. 1. Additionally, each slave device 504*a*-504*n* may incorporate the structure and functionality of user modules 252*a*-252*n*. Each slave device 504*a*-504*n*, therefore, may be controlled by master device 502 in real-time while enabling the user to manually override the operation of the exercise device in opposition to control signals received from master device 502.

As illustrated in FIG. 20, each slave 504*a*-504*n* may optionally be a master to subsequent sub-slave device 506*a*-506*n*, as shown in broken lines. In such a manner, various exercise devices may be separated into different groups. For example, slave 504*a* may receive a beginner level control signal from master 502. In turn, slave 504*a* may control the operation of one or more sub-slave devices 506*a*-506*n* that are operated by one or more beginners. Similarly, slave 504*b* may receive an intermediate level control signal from master 502 and subsequently control one or more sub-slaves (not shown), while slave 504*n* may receive an advanced level control signal from master 502 and subsequently control one or more sub-slaves (not shown).

According to another alternate configuration, master device 502 may receive information from each slave device 504*a*-504*n* representative of the user's heart rate, blood pressure, and the like. Master device 502 may, therefore, modify each slave device 504*a*-504*n* or sub-slave device 506*a*-506*n*, whether individually or collectively, based upon the data received from the user. For example, if the user's heart rate is too high, master device 502 may automatically reduce one or more operating parameters of the exercise device, such as speed, incline, resistance, and the like.

Although it is preferred that the communications performed according to the present invention (e.g., the first signal and the second signal) be in real-time, it is also possible to achieve many objects of the present invention by engaging in communication other than real-time.

According to one aspect of the present invention, an exercise device is disclosed that incorporates various audio/video features into the device or exercise device itself rather than having external audio/video features connected thereto. The exercise device may also include sensors that track the activity level of an individual on the exercise device, to determine whether a user is actually exercising or to determine whether the user is old enough to be using the exercise device.

According to another aspect of the present invention, one or more users are enabled to exercise in a group setting, while being distantly located one from another. Furthermore, the present invention enables home exercise equipment users to interact with trainers, other users, physical therapists, physicians, and the like in live-on-live workout sessions and, in some situations, allow a trainer, physical therapists, physicians, and the like to control at least one operating parameter of the exercise device upon which the user is training.

To enable the above-described communication, a user may access a communication system or module that facilitates communication between one or more users, trainers, or third parties. Such communication system or module may include at least one web site with associated web pages. As a user accesses the communication system or module, statistical information related to an individual's workout regime, such as how much time an individual spends on each various exercise device, the locations where they trained, when each user accesses the communication system or modules, and the like is gathered.

Generally, the communication system or module, and hence the web site, may enable a user to access information and programming contained therein, while, in one embodiment, the communication system or module has the ability to control at least one operating parameter of the device or exercise device via the web site and web pages. In one case, when a user activates one or more input devices, such as a touch sensitive screen having a visual representation of the web page thereon, the communication system or module, via the web site, changes the operational parameters of the device or exercise device.

Various programming is accessible through the communication system or module. For example, the user may select live or recorded programming. One type of programming or capability of the communication system or module relates to competitive motivational content. Such functionality allows an individual to compare the amount of miles traveled on an exercise device against individuals throughout the world engaging in similar activities. Therefore, competitors around the world may race against one another. Optionally, two or more users may link their exercise devices directly without the need to communicate through the communication system or module.

Another type of motivational content may include one or more electronic magazines or books that a user may download to view while exercising. Yet another type of motivational content or programming relates to the ability of the user to view an exercise profile representative of the exercise program currently being performed by the user. Such a profile may be displayed to the user continuously, periodically, or other under the control of the user and/or the communication system or module. In one configuration, the exercise profile may appear and overlay the visual image that the user is watching, whether the visual image is a television broadcast, webcast, or the like.

Another type of motivational content relates to various advertisements. During the exercise program a user may receive commercial advertising through an advertising banner that may continuously or periodically appear on the video display. Optionally, the advertisement may appear in a picture-in-picture advertisement that is delivered to the user as a micro-commercial that is displayed to the user and subsequently removed.

The programming received from the communication system or module may be live or recorded. In some situations the live programming received by the user may be too difficult or not difficult enough for the user of the exercise device. The present invention provides scaling controls that allow the user to scale the signals received from the communication system or module and/or the trainer. In this manner, the exercising user may increase or decrease the intensity of the exercise program. Such scaling may be achieved either at the user device, trainer device, the communication system or module, or at some other third party modules that may control the operation of the user's exercise device. By selecting a particular option on the web page, the user's appliance will be controlled according to the scaled choice. Optionally, the user may define a maximum limit for one or more of the operating parameters of the device, such that transmitted programming is limited in accordance with the maximum values defined for each operating parameter.

According to another aspect of the present invention, the systems, devices, and modules of the present invention enable bi-directional communication between one or more user devices and one or more trainer devices. The communication system or module of the present invention may retrieve information from the devices and/or exercise devices and evaluate the operating parameters of the device and/or exercise device. The communication system or module may analyze any measurable parameter of the device or exercise device and may optionally analyze any measurable parameter of a user exercising using the exercise device. In response to this analysis, the communication system or module prescribes a particular action for the device or exercise device to perform, such as changing the speed of a treadmill, inclination of a treadmill, and the like.

According to yet another aspect of the present invention, the exercise device is capable of being controlled by signals from the communication system or module and/or physical controls integrated onto the device or exercise device. The physically integrated controls and the controls from the communication system or module may be passed through a buffer that controls the exercise device or device. In this way, in the event that connectivity to the communication system or module is lost, a user of the device or exercise device would still be capable of controlling the device or exercise device.

According to another aspect of the present invention, communication system or modules may remotely update various portions of a device or exercise device according to the need or direction of the user of the device or as determined by the communication system or module. For example, communication system or module may change any and all parameters related to the device or exercise device, such as the BIOS, or some other software.

According to another aspect of the present invention, the exercise device or device includes a diagnostic button. Upon activation of the diagnostic button, the internal hardware and/or software components of the device or exercise device, solely, or in combination with the communication system or modules tests and checks the various hardware and/or software modules, components, or elements of the device or exercise device. If any problems are found the internal hardware and/or software components of the device or exercise device, solely, or in combination with the communication system or modules attempt to fix the problems. Additionally, the diagnostic button may activate a downloading sequence to update information on the appliance with new software from a central database, such as at communication system or module.

According to another aspect of the present invention, the present invention may includes one or more interfaces that may communicate with existing hardware and/or software components of various existing devices and exercise devices. As such, those devices or exercise devices not currently capable of communicating with communication system or module, may be retrofitted with various hardware and/or software modules as described herein to allow the exercise device or device to communicate with the communication system or module.

As mentioned, the presently described systems, methods, and devices may be used in a master-slave system. In such a system, changes to the operating parameters of the master are translated to the operating parameters of the slave, thereby controlling the operation of the device or exercise device. For example, in a spinner class, upon activation of a more intense riding experience by the master, the slave spinners also give their riders a similarly intense riding experience. The master may selectively choose groups of participants based on various criteria, such as participant's heart rates, and change those participants exercise program, while maintaining other participants at the original or different exercise level.

Embodiments of the present invention are also disclosed in copending United States patent applications entitled (i) Computer Systems and Methods for Interaction with Exercise Device, to Scott R. Watterson, William T. Dalebout and Darren C. Ashby, filed Aug. 18, 2000, which is incorporated herein in its entirety by reference; and (ii) Systems and Methods for Interaction with Exercise Device, to Scott R. Watterson, William T. Dalebout and Darren C. Ashby, filed Aug. 18, 2000, which is incorporated herein in its entirety by reference.

As used in this specification and the appended claims, the phrases "communicating with," and "in communication with" and similar phrases shall mean any type of applicable communication known to one skilled in the art in light of the disclosure herein, such as electrical communication, optical communication, physical communication, magnetic communication, software communication, hardware communication, data communication, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of operating one or more operating parameters of an exercise module of a user module, the method comprising the steps of:
   (a) preparing a first signal for delivery to a communication module;
   (b) in response to the first signal, producing and packetizing programming having one or more control signals for controlling the one or more operating parameters of the exercise module; and
   (c) reproducing and depacketizing the programming and adjusting the one or more operating parameters of the exercise module in response to the one or more control signals.

2. A method as recited in claim 1, wherein the preparing step comprises:
   (a) gathering one or more signals representative of a user exercising on the exercise module; and
   (b) manipulating the one or more signals into a form capable of being delivered via a network to the communication module.

3. A method as recited in claim 1, wherein the first and second signals are each real time signals and wherein the programming is reproduced and depacketized in real time.

4. A method as recited in claim 3, wherein the producing and packetizing step comprises:
   (a) transmitting the first real-time signal to a trainer module located at a distant location from the user module;
   (b) in response to the first real-time signal, creating the programming and the one or more control signals; and
   (c) synchronizing the programming and the one or more control signals before transmittal to the communication module.

5. A method as recited in claim 1, wherein the producing and packetizing step comprises:
   (a) selecting the programming from a data storage module of the communication module;
   (b) in response to the first signal, generating the one or more control signals; and
   (c) synchronizing the programming and the one or more control signals.

6. A method as recited in claim 1, further comprising the step of transmitting the programming and the one or more control signals from the communication module to the exercise module.

7. A method as recited in claim 1, wherein the reproducing step comprises delivering the programming to one or more output devices.

8. A method as recited in claim 7, wherein the one or more output devices comprises one or more video displays and one or more speakers.

* * * * *